United States Patent
Kim et al.

(10) Patent No.: US 11,806,350 B2
(45) Date of Patent: *Nov. 7, 2023

(54) PREVENTION AND/OR TREATMENT OF CNS DISORDERS

(71) Applicant: ILDONG PHARMACEUTICAL CO., LTD., Seoul (KR)

(72) Inventors: Kyung-Sun Kim, Hwaseong-si (KR); Jeong-Ah Kim, Hwaseong-si (KR); An-Na Moon, Hwaseong-si (KR); Dong-Keun Song, Hwaseong-si (KR); Yoon-Suk Lee, Hwaseong-si (KR); Ju-Young Jung, Hwaseong-si (KR)

(73) Assignee: ILDONG PHARMACEUTICAL CO., LTD., Seoul (KR)

( * ) Notice: Subject to any disclaimer, the term of this patent is extended or adjusted under 35 U.S.C. 154(b) by 7 days.

This patent is subject to a terminal disclaimer.

(21) Appl. No.: 17/528,342

(22) Filed: Nov. 17, 2021

(65) Prior Publication Data

US 2022/0152034 A1    May 19, 2022

Related U.S. Application Data

(60) Provisional application No. 63/115,972, filed on Nov. 19, 2020.

(51) Int. Cl.
*A61K 31/519*    (2006.01)

(52) U.S. Cl.
CPC .................... *A61K 31/519* (2013.01)

(58) Field of Classification Search
CPC .............................. A61K 31/519; A61P 35/00
See application file for complete search history.

(56) References Cited

U.S. PATENT DOCUMENTS

| | | |
|---|---|---|
| 6,124,300 A | 9/2000 | Rajagopalan et al. |
| 2006/0111373 A1 | 5/2006 | Gillespie et al. |

FOREIGN PATENT DOCUMENTS

| | | | |
|---|---|---|---|
| EP | 1 349 857 B1 | 6/2010 | |
| WO | 01/02400 A1 | 1/2001 | |
| WO | 02/055082 A1 | 7/2002 | |
| WO | WO-02055082 A1 * | 7/2002 | ............ A61K 31/00 |
| WO | 2011/050160 A1 | 4/2011 | |
| WO | WO-2011050160 A1 * | 4/2011 | ........... A61K 31/519 |
| WO | 2019/086074 A1 | 5/2019 | |
| WO | 2021/099837 A1 | 5/2021 | |

OTHER PUBLICATIONS

Adenosine A2A Receptor Antagonists and Parkinson's Disease (Brian C. Shook* and Paul F. Jackson, ACS Chem. Neurosci. 2011, 2, 10, 555-567 Publication Date: Jun. 21, 2011).*
Aryl Coupling Reactions of Pyrazolo[3,4-d ]pyrimidin-4-yl Radicals Press et al. J. Org. Chem., vol. 48, No. 24, 1983 (Year: 1983).*
Gillespie et al., "Antagonists of the human adenosine A2A receptor. Part 3: Design and synthesis of pyrazolo[3,4-d]pyrimidines, pyrrolo[2,3-d]pyrimidines and 6-arylpurines", Bioorganic& Medicinal Chemistry Letters, vol. 18, 2008, pp. 2924-2929 (6 pages total).
International Search Report dated Feb. 25, 2022 from the International Searching Authority in International Application No. PCT/IB2021/060709.
Written Opinion dated Feb. 25, 2022 from the International Searching Authority in International Application No. PCT/IB2021/060709.

* cited by examiner

*Primary Examiner* — Jeffrey S Lundgren
*Assistant Examiner* — Eric Tran
(74) *Attorney, Agent, or Firm* — Sughrue Mion, PLLC

(57) ABSTRACT

Adenosine receptor (e.g., A2A and/or A1 receptor) antagonist compounds and compositions including said compounds are disclosed. The present disclosure also provides methods of using said compounds and compositions for modulating (e.g., inhibiting or antagonizing) A2A and/or A1 receptor in a biological system. The compounds and compositions find use in various therapeutic applications including the treatment of central nervous system or neurodegenerative diseases, such as Parkinson's disease. The compounds and compositions may also find use in various therapeutic applications including the treatment of cancer and in immuno-oncology.

16 Claims, 3 Drawing Sheets

PREVENTION AND/OR TREATMENT OF CNS DISORDERS

CROSS REFERENCE TO RELATED APPLICATIONS

This application claims the benefit of U.S. Provisional Application No. 63/115,972, filed Nov. 19, 2020, the content of which is incorporated herein by reference in its entirety.

INTRODUCTION

Adenosine carries out many biological functions through particular cell receptors and is associated with a variety of biological activities including immune functions and inflammation.

There are four types of adenosine receptor (A1, A2A, A2B, and A3), and they are connected to the heteromeric G protein. Each of the A2A receptor and A2B receptor is connected to Gs subtype of Ga proteins. When these receptors are stimulated, the receptor format changes, and such a change induces the discharge of the Gs subunit activated by the Gβ ρ dimer, and then hydrolysis of the adenosine triphosphate (ATP) in the cell to produce cyclic adenosine monophosphate (cAMP). The cAMP synthesis activates protein kinase A (PKA) and phosphorylation of other proteins. In the T cell, mainly type I PKA isoform exists around the T cell receptor (TCR), and if activation of PKA increases due to the increased cAMP levels, the TCR signal transmission process is inhibited, thereby contributing to the occurrence of various illnesses.

Cancer cells produce significantly more adenosine than is produced by normal cells. In cancer cells, high-density adenosine induces activation of the A2A receptor to inhibit the immune system thereby and protect the cells. In the micro-environment of a tumor, the concentration of adenosine can be at 50 μM, an increase over normal cells, and lead to immunosuppression of T-cell function and activation. An A2A receptor antagonist can be used to adjust the cancer cell's inhibition of the immune system to induce anticancer effects.

A2A receptor antagonists are in development for immuno-oncology therapies. A2A receptor antagonists can enhance antitumor immunity. The A2A receptor is widely produced in white blood cells. When a T cell's A2A receptor becomes activated, TCR-mediated cytotoxicity and production of cytokines decreases, proliferation of T cells is inhibited, and expansion of Treg cells is induced. In immuno-oncology, the immunity checkpoint inhibitors of PD-1 or PD-L1 (e.g., antibody inhibitors) are widely used. However, statistically only 20% to 30% of patients produce PD-1/PD-L1, and thus there are many patients who do not benefit from the efficacy of such inhibitors. Treatments involving immunity checkpoint inhibitors in combination with A2A receptor antagonists are of interest.

Control of adenosine receptors is of interest for treatment of various indications. Modulating activity of the adenosine A1 receptor is of interest for treatment of nervous system disorders, asthma, heart failure, renal failure, and the like; antagonizing the adenosine A2A receptor is of interest for the treatment of Parkinson's disease, and the like; modulating activity of the adenosine A2B receptor is of interest for the treatment of chronic lung disorders such as asthma, cancer, in immuno-oncology and the like; and modulating the adenosine A3 receptor is of interest for treatment of asthma and chronic obstructive lung disorders, glaucoma, cancer, cerebral apoplexy, and the like.

SUMMARY

The present disclosure provides adenosine receptor (e.g., A2A and/or A1 receptor) antagonist compounds and compositions including said compounds. The present disclosure also provides methods of using said compounds and compositions for modulating (e.g., inhibiting or antagonizing) A2A and/or A1 receptor in a biological system. The compounds and compositions find use in various therapeutic applications including the treatment of central nervous system or neurodegenerative diseases, such as Parkinson's disease. In some embodiments, the compounds and compositions find use in various therapeutic applications including the treatment of cancer and in immuno-oncology.

In a first aspect, the present disclosure provides an A2A and/or A1 antagonist compound of formula (Ia):

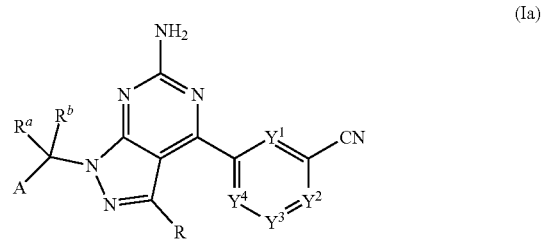

wherein:
R is H, $(C_1-C_3)$alkyl, or substituted $(C_1-C_3)$alkyl;
$Y^1$ to $Y^4$ are independently selected from $CR^{10}$ and N, wherein at least two of $Y^1$ to $Y^4$ are independently $CR^{10}$;
each $R^{10}$ is independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;
$R^a$ and $R^b$ are each independently selected from H, F, $(C_1-C_3)$alkyl, and substituted $(C_1-C_3)$alkyl, or $R^a$ and $R^b$ are cyclically linked and together with the carbon atom to which they are attached form a cyclopropyl or substituted cyclopropyl; and
A is phenyl, substituted phenyl, pyridyl or substituted pyridyl;
or a solvate, a hydrate, a prodrug, and/or a stereoisomer thereof, or a pharmaceutically acceptable salt thereof.

In a second aspect, the present disclosure provides a pharmaceutical composition comprising a compound, or a pharmaceutically acceptable salt thereof as described herein (e.g., a compound of formula (I)-(XVI)), and a pharmaceutically acceptable excipient.

In a third aspect, the present disclosure provides methods of modulating (e.g., inhibiting or antagonizing) an adenosine A2A and/or A1 receptor, comprising contacting a sample or cell or biological system with an effective amount of a compound as described herein (e.g., a compound of formula (I)-(XVI) or a pharmaceutically acceptable salt thereof).

Also provided are methods of treating a central nervous system or neurodegenerative disease that includes administering to a subject having or at risk from a central nervous system or neurodegenerative disease a therapeutically effective amount of an A2A and/or A1 receptor antagonist compound (e.g., a compound of formula (I)-(XVI) or a pharmaceutically acceptable salt thereof, as described herein). Also provided are methods of treating cancer that include administering to a subject having cancer a therapeutically effective amount of an A2A and/or A1 receptor antagonist compound (e.g., as described herein). In some embodiments, the method further includes co-administering to the subject an additional active agent, such as an immune checkpoint inhibitor.

In an additional aspect, the present disclosure provides a method selected from (i) a method of treating a central nerve system (CNS) disorder selected from the group consisting of Huntington's disease, Parkinson's disease, Alzheimer's disease, schizophrenia, mild-cognitive impairment, attention deficit hyperactivity disorder (ADHD), multiple sclerosis, vascular dementia, amyotrophic lateral sclerosis; (ii) a method of treating an injury or disease that results in neuronal degeneration selected from the group consisting of closed head injuries, blunt trauma, penetrating trauma, hemorrhagic stroke, ischemic stroke, glaucoma, cerebral ischemia, spinal cord injury, ageing, and neuronal damage caused by surgical procedures (wherein the injury may be a primary nervous system injury selected from the group comprising closed head injuries, blunt trauma, penetrating trauma, hemorrhagic stroke, ischemic stroke, glaucoma, cerebral ischemia, spinal cord injury, aging, and neuronal damage caused by surgical procedures); or (iii) a method of treating a movement disorder, wherein the method comprises administering to a subject in need thereof an effective amount of an adenosine receptor (e.g., A2A and/or A1) antagonist compound of the formula (Ia) described herein. In the above mentioned methods, the A2A and/or A1 antagonist compound may be a compound of formula (I)-(XVI). In the above mentioned methods, the CNS disorder, neurodegenerative diseases, or the movement disorder may be associated with an adenosine receptor (e.g., A2A and/or A1 receptor).

BRIEF DESCRIPTION OF DRAWINGS

In order to illustrate the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3A shows the percentage (%) of contralateral forelimb usage by animals administered per oral gavage (PO). Statistics: One-way ANOVA followed by Bonferroni's posttest of treatment, all groups vehicle MTC) group. FIG. 3B shows the percentage (%) of contralateral forelimb usage by animals administered internasal (IN). Statistics: Kruskal0Walls followed by Dunn's posttest of treatment, all groups vs. vehicle (DMSO) group. Data are presented as mean±SEM per group.

DETAILED DESCRIPTION

Adenosine Receptor Antagonist Compounds

Figure 1:
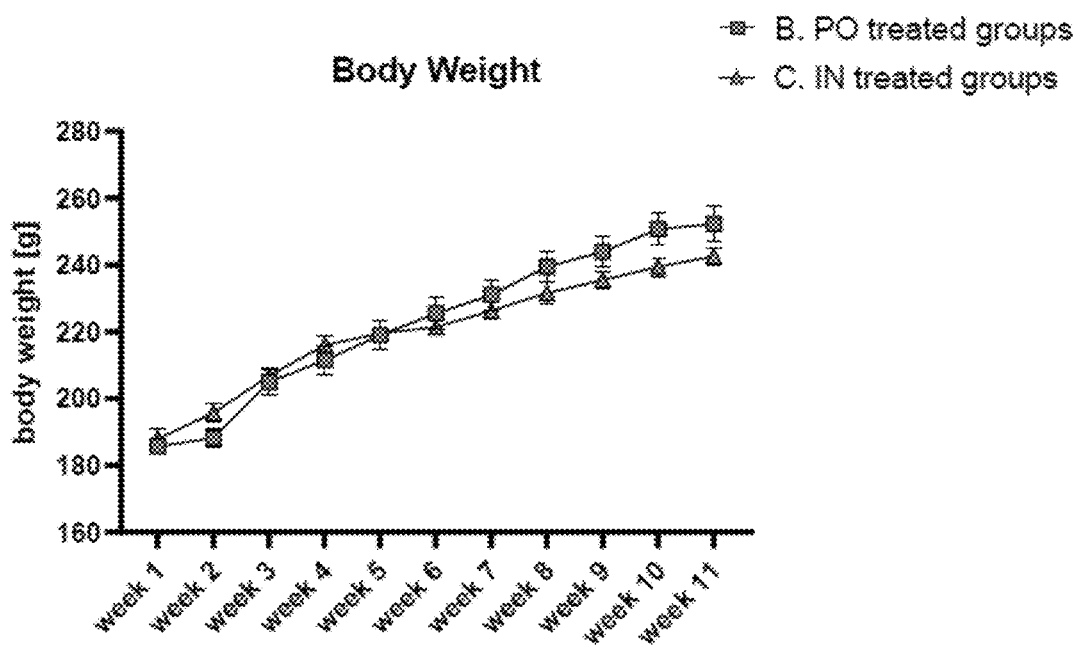
FIG. 1 is a graph showing the weekly bodyweight of each treatment group throughout the entire treatment period. Data is represented as mean±SEM. Statistics: two-way ANOVA followed by Bonferroni's posttest of treatment, Group B versus C.
Figure 2A:
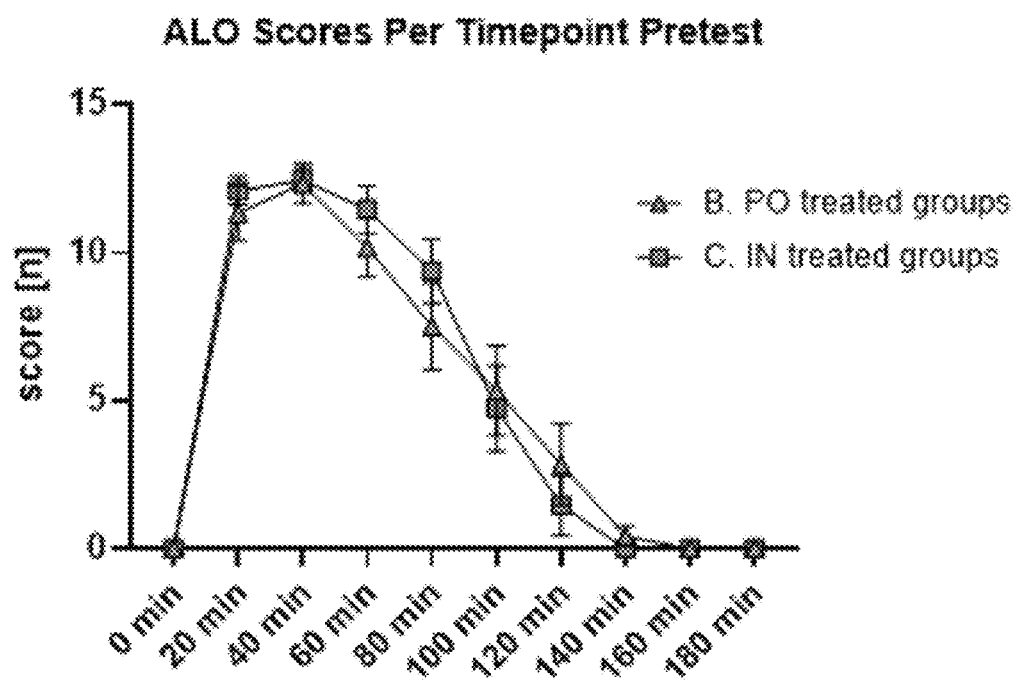
FIGS. 2A and 2B are graphs showing the ALO AIMS assessment over the time. The graphs represent the mean score of ALO AIMs per group. Data are displayed as a bar graph of mean±SEM. Statistics: two-way ANOVA followed by Bonferroni's posttest of treatment, Group B versus C.
Figure 2B:
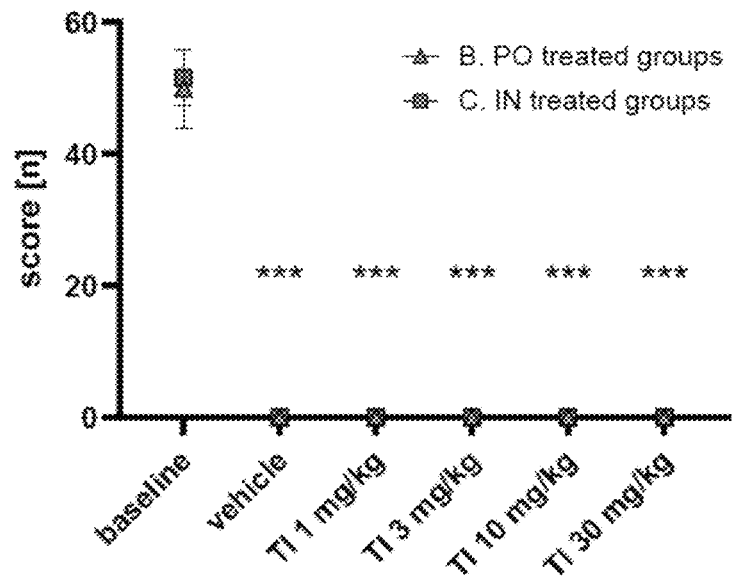
Figure 3A:
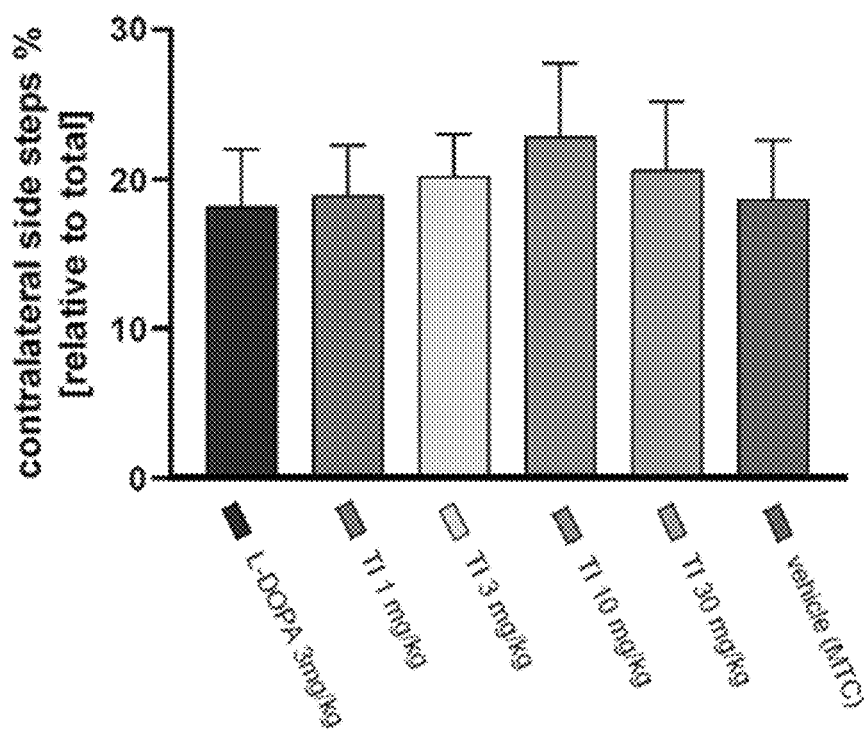
FIGS. 3A and 3B are graphs showing cylinder test results.
Figure 3B:
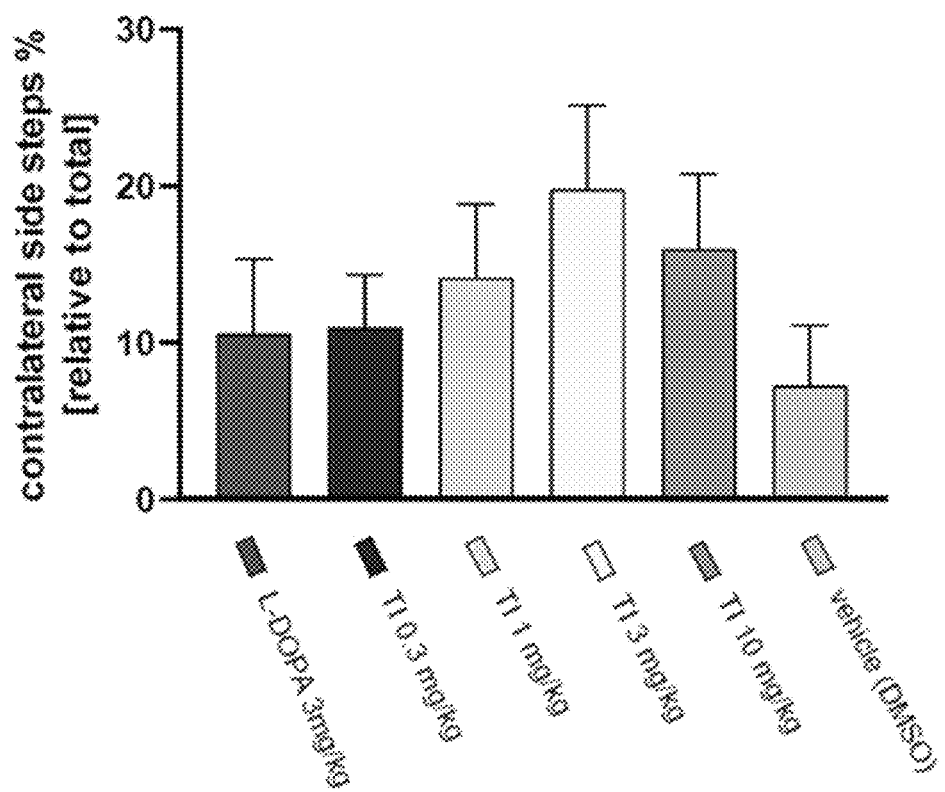

As summarized above, the present disclosure provides A2A and/or A1 receptor antagonist compounds and compositions and their uses. The compounds can modulate adenosine A2A and/or A1 receptor in cells and biological systems of interest. The compounds find use in a variety of therapeutic applications, including treatment of central nervous system or neurodegenerative diseases, such as Parkinson's Disease, and in the treatment of cancer and in immuno-oncology.

The compounds of this disclosure can be described as cyano-substituted fused pyrimidine compounds that include a core structure having a 2-amino-pyrimidine ring fused to a five-membered heterocycle ring. The core structure can itself be further substituted with a benzonitrile substituent (e.g., a 3-cyano-phenyl) or a derivative thereof (e.g., a cyano-pyridyl substituent). The fused five membered heterocycle ring can be further substituted with an optionally substituted benzyl group. In some cases, the compounds have a 1H-pyrazolo[3,4-d]pyrimidine-6-amine core structure that is further substituted as described herein. The A2A and/or A1 receptor antagonist compounds of Formula (I)-(XVI) and (Ia) are described in WO2021099837A, the disclosure of which is incorporated herein by reference in its entirety.

In some embodiments, the compound is a benzonitrile-substituted fused pyrimidine compound, e.g., of the formula:

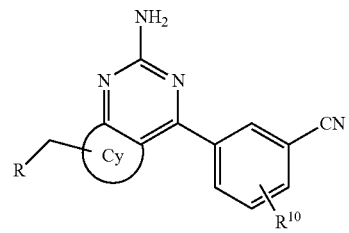

or a derivative thereof (e.g., a derivative compound where the 3-benzonitrile group is replaced with a cyano-pyridyl group), where Cy is a fused five membered heterocycle ring (e.g., heteroaryl or heterocycloalkyl ring) that contains at least one hetero atom selected from nitrogen, oxygen, and sulfur; R is an optionally substituted phenyl group; and $R^{10}$ is one or more optional substituents. In some embodiments, R is a phenyl substituted by $R^{11}$, $R^{12}$, and/or $R^{13}$ groups each independently selected from halogen, hydroxyl group, thiol group, carbonyl group, amide group, nitro group, amino group, substituted or unsubstituted $(C_1-C_5)$alkyl group, substituted or unsubstituted $(C_2-C_5)$alkenyl group, substituted or unsubstituted $(C_2-C_5)$alkynyl group, substituted or unsubstituted $(C_1-C_3)$haloalkyl group, and substituted or unsubstituted $(C_1-C_3)$aminoalkyl group or substituted or unsubstituted $(C_1-C_5)$alkoxy group, and $R^{10}$ is one or more groups independently selected from hydrogen, halogen, hydroxyl group, thiol group, substituted or unsubstituted $(C_1-C_5)$alkyl group, substituted or unsubstituted ($C_2$-$C_5$)alkenyl group, substituted or unsubstituted ($C_2$-$C_5$)alkynyl group, substituted or unsubstituted ($C_1$-$C_3$)haloalkyl group, substituted or unsubstituted ($C_1$-$C_5$)alkoxy group, or cyano group.

In some embodiments, the aforementioned $R^{11}$ and $R^{13}$ are each independently hydrogen, halogen, ($C_1$-$C_5$)alkyl group, or ($C_1$-$C_3$)haloalkyl group, the aforementioned $R^{12}$ is hydrogen or amino group, and each aforementioned $R^{10}$ is independently hydrogen, halogen, ($C_1$-$C_5$)alkyl group, or cyano group. Further embodiments of the formula above are described herein.

Aspects of the present disclosure include A2A and/or A1 receptor antagonist compounds of formula (I):

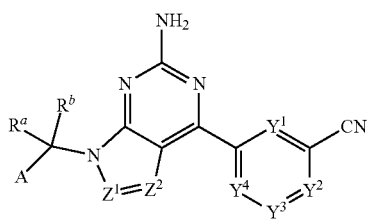

wherein:
- $Z^1$ and $Z^2$ are independently selected from CR and N, wherein at least one of $Z^1$ and $Z^2$ is N;
- R is H, ($C_1$-$C_3$)alkyl, or substituted ($C_1$-$C_3$)alkyl;
- $Y^1$ to $Y^4$ are independently selected from $CR^{10}$ and N, wherein at least two of $Y^1$ to $Y^4$ are independently $CR^{10}$;
- each $R^{10}$ is independently selected from H, ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$) alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;
- $R^a$ and $R^b$ are each independently selected from H, F, ($C_1$-$C_3$)alkyl, and substituted ($C_1$-$C_3$)alkyl, or $R^a$ and $R^b$ are cyclically linked and together with the carbon atom to which they are attached form a cyclopropyl or substituted cyclopropyl; and
- A is phenyl, substituted phenyl, pyridyl or substituted pyridyl;

or a solvate, a hydrate, a prodrug, and/or a stereoisomer thereof, or a pharmaceutically acceptable salt thereof.

In some embodiments of formula (I), $Y^1$ to $Y^4$ are independently selected from $CR^{10}$ and N, wherein at least three of $Y^1$ to $Y^4$ are independently $CR^{10}$.

In some embodiments of formula (I), $Z^1$ is N and $Z^2$ is CR such that the compound is of formula (Ia):

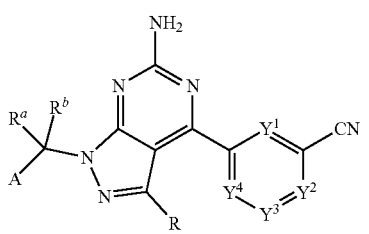

or a solvate, a hydrate, a prodrug, and/or a stereoisomer thereof, or a pharmaceutically acceptable salt thereof.

In some embodiments of formula (Ia), R is ($C_1$-$C_3$)alkyl. In some embodiments of formula (Ia), R is H.

In some embodiments of formula (I)-(Ia), A is phenyl. In some embodiments of formula (I)-(Ia), A is substituted phenyl. In some embodiments of formula (I)-(Ia), A is phenyl or phenyl substituted with one, two or three $R^{20}$ groups, each $R^{20}$ is independently selected from ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$)alkynyl, ($C_1$-$C_3$)haloalkyl, ($C_1$-$C_8$)alkoxy, substituted ($C_1$-$C_8$) alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

In some embodiments of formula (I)-(Ia), A is pyridyl. In some embodiments of formula (I)-(Ia), A is substituted pyridyl. A can be an optionally substituted pyridyl that is a 2-pyridyl, 3-pyridyl or 4-pyridyl. In some embodiments of formula (I)-(Ia), A is pyridyl or pyridyl substituted with one, two or three $R^{20}$ groups, each $R^{20}$ is independently selected from ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$)alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

In some embodiments of formula (I)-(Ia), $R^a$ and $R^b$ are each H.

In some embodiments of formula (Ia), $Y^1$ to $Y^4$ are independently selected from $CR^{10}$ and N, wherein at least three of $Y^1$ to $Y^4$ are independently $CR^{10}$.

In some embodiments of formula (Ia), the compound is of formula (II):

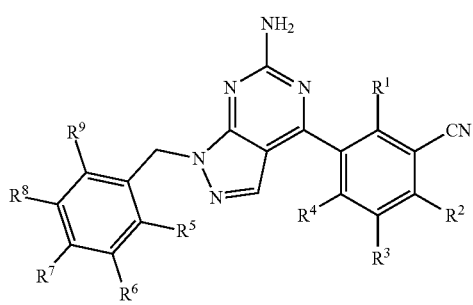

wherein:
- $R^1$ to $R^9$ are independently selected from H, ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$) alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

or a solvate, a hydrate, a prodrug, and/or a stereoisomer thereof, or a pharmaceutically acceptable salt thereof.

In some embodiments of formula (II), $R^1$ to $R^9$ are independently selected from H, ($C_1$-$C_5$)alkyl, substituted ($C_1$-$C_5$)alkyl, ($C_1$-$C_3$)haloalkyl, ($C_1$-$C_5$)alkoxy, substituted ($C_1$-$C_5$)alkoxy, —$NH_2$, substituted amino, halogen, and hydroxyl. In some embodiments of formula (II), $R^1$ to $R^9$ are independently selected from H, $NH_2$, F, $CH_3$, and $CF_3$.

In some embodiments of formula (II), the compound is of formula (III):

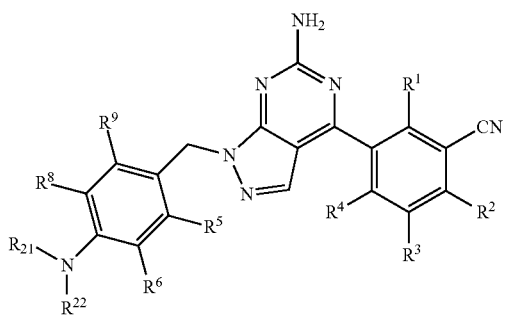

(III)

wherein:
$R^{21}$ and $R^{22}$ are independently selected from H, $(C_1-C_8)$alkyl, substituted $(C_1-C_8)$alkyl, $SO_2R^{30}$, and $COR^{30}$, wherein $R^{30}$ is $(C_1-C_8)$alkyl, or substituted $(C_1-C_8)$alkyl;

or a solvate, a hydrate, a prodrug, and/or a stereoisomer thereof, or a pharmaceutically acceptable salt thereof.

In some embodiments of formula (III), $R^{21}$ and $R^{22}$ are each H.

In some embodiments of formula (III), $R^5$, $R^6$, $R^8$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (III), $R^5$, $R^6$, $R^8$ and $R^9$ are independently selected from H, F, $CH_3$, and $CF_3$. In some embodiments of formula (III), $R^5$ and $R^9$ are each H.

In some embodiments of formula (III), $R^2$ to $R^4$ are each H, and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (III), $R^1$ is selected from H, F, $CH_3$, and $CF_3$.

In some embodiments of formula (III), the compound is selected from:

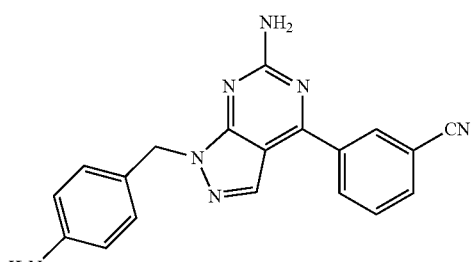

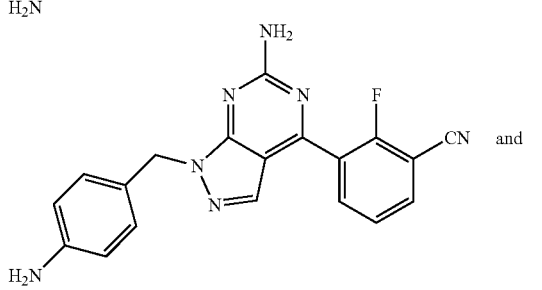

and

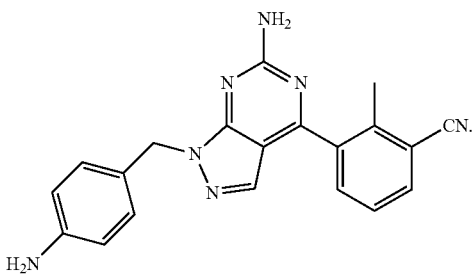

or a solvate, a hydrate, a prodrug, and/or a stereoisomer thereof, or a pharmaceutically acceptable salt thereof.

In some embodiments of formula (III), the compound is of formula (IV):

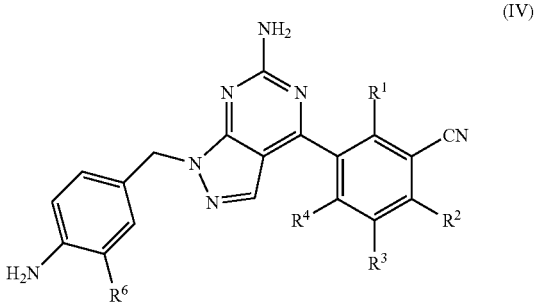

(IV)

or a solvate, a hydrate, a prodrug, and/or a stereoisomer thereof, or a pharmaceutically acceptable salt thereof.

In some embodiments of formula (IV), $R^6$ is selected from $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (IV), $R^6$ is selected from $(C_1-C_5)$alkyl, substituted $(C_1-C_5)$alkyl, and $(C_1-C_3)$haloalkyl. In some embodiments of formula (IV), $R^6$ is $CH_3$ or $CF_3$.

In some embodiments of formula (IV), $R^2$ to $R^4$ are each H, and $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (IV), $R^1$ is selected from H, F, $CH_3$, and $CF_3$.

In some embodiments of formula (IV), the compound is selected from:

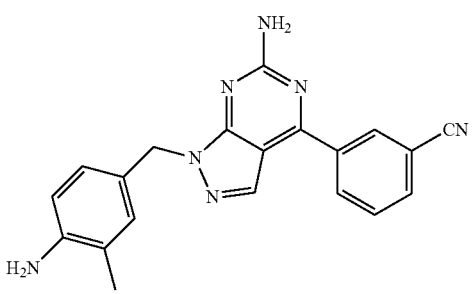

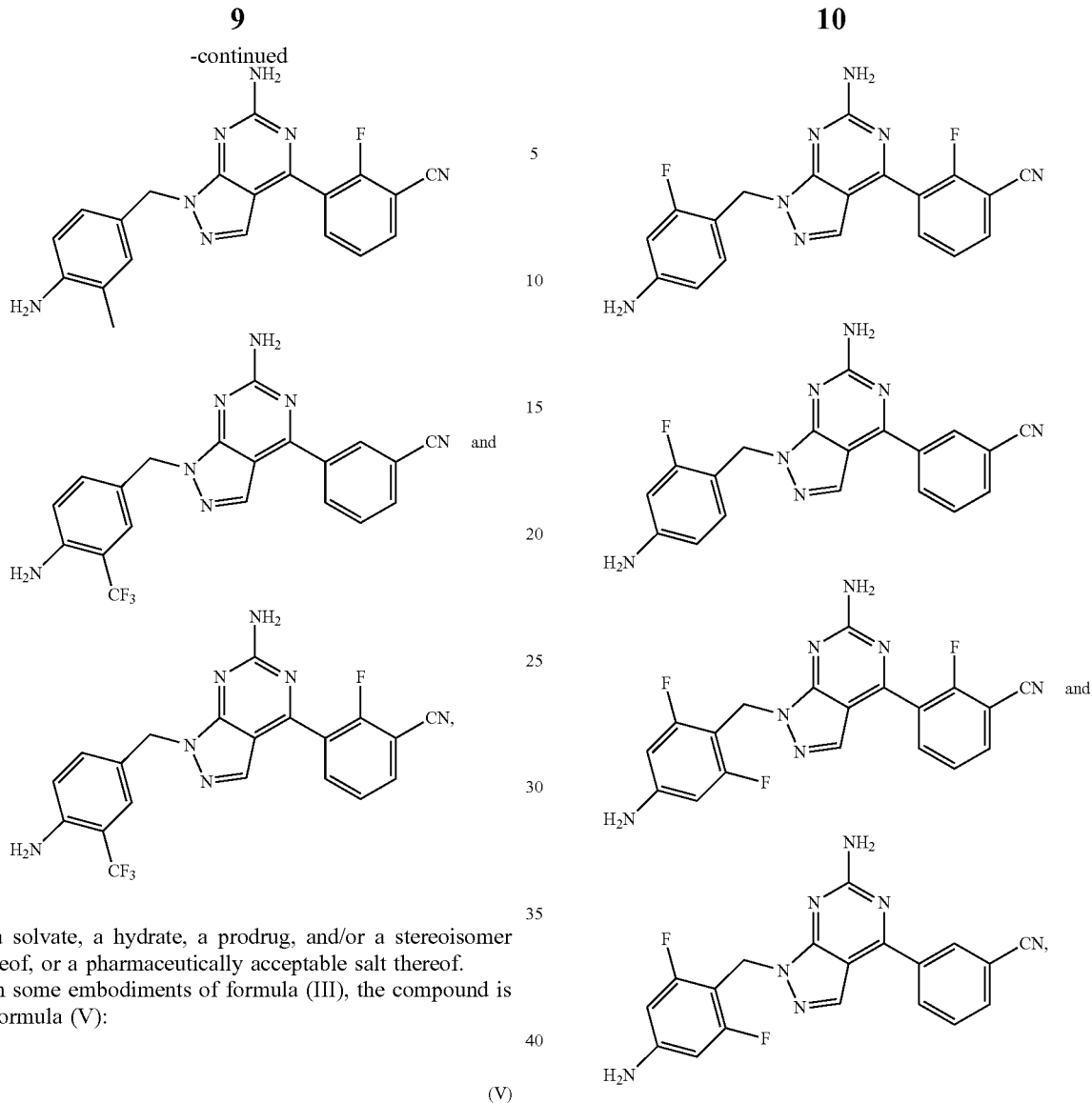

or a solvate, a hydrate, a prodrug, and/or a stereoisomer thereof, or a pharmaceutically acceptable salt thereof.

In some embodiments of formula (III), the compound is of formula (V):

or a solvate, a hydrate, a prodrug, and/or a stereoisomer thereof, or a pharmaceutically acceptable salt thereof.

In some embodiments of formula (V), $R^5$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (V), $R^5$ and $R^9$ are independently selected from H and halogen. In some embodiments of formula (V), $R^5$ is F. In some embodiments of formula (V), $R^9$ is F. In some embodiments of formula (V), $R^5$ and $R^9$ are each F. In some embodiments of formula (V), $R^5$ is H and $R^9$ is F.

In some embodiments of formula (V), the compound is selected from:

or a solvate, a hydrate, a prodrug, and/or a stereoisomer thereof, or a pharmaceutically acceptable salt thereof.

In some embodiments of formula (II), the compound is of formula (VI):

or a solvate, a hydrate, a prodrug, and/or a stereoisomer thereof, or a pharmaceutically acceptable salt thereof.

In some embodiments of formula (VI), $R^5$, $R^6$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted ($C_1$-$C_5$)alkoxy, —$NH_2$, substituted amino, halogen, and hydroxyl. In some embodiments of formula (VI), $R^6$ is selected from H, ($C_1$-$C_5$)alkyl, substituted ($C_1$-$C_5$)alkyl, and ($C_1$-$C_3$)haloalkyl. In some embodiments of formula (VI), $R^6$ is $CH_3$ or $CF_3$. In some embodiments of formula (VI), $R^6$ is H.

In some embodiments of formula (VI), $R^5$ and $R^9$ are independently selected from H and halogen. In some embodiments of formula (VI), $R^5$ is F. In some embodiments of formula (VI), $R^9$ is F. In some embodiments of formula (VI), $R^5$ and $R^9$ are each F. In some embodiments of formula (VI), $R^5$ is H and $R^9$ is F.

In some embodiments of formula (VI), the compound is selected from:

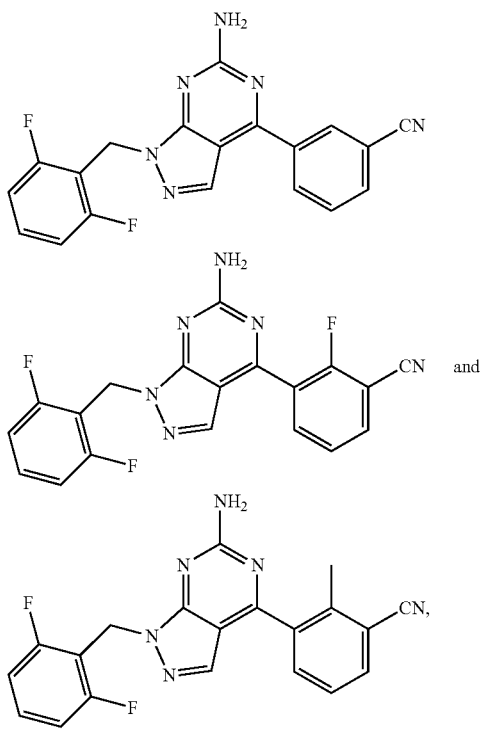

or a solvate, a hydrate, a prodrug, and/or a stereoisomer thereof, or a pharmaceutically acceptable salt thereof.

In some embodiments of formula (II)-(VI), $R^1$ to $R^4$ are independently selected from H, ($C_1$-$C_5$)alkyl, substituted ($C_1$-$C_5$)alkyl, ($C_1$-$C_3$)haloalkyl, ($C_1$-$C_5$)alkoxy, substituted ($C_1$-$C_5$)alkoxy, —$NH_2$, substituted amino, halogen, and hydroxyl. In some embodiments of formula (II)-(VI), $R^1$ to $R^4$ are independently selected from H, ($C_1$-$C_5$)alkyl, substituted ($C_1$-$C_5$)alkyl, ($C_1$-$C_3$)haloalkyl and halogen.

In some embodiments of formula (II)-(VI), $R^1$ is H. In some embodiments of formula (II)-(VI), $R^1$ is selected from ($C_1$-$C_5$)alkyl, substituted ($C_1$-$C_5$)alkyl, ($C_1$-$C_3$)haloalkyl and halogen. In some embodiments of formula (II)-(VI), $R^1$ is F, $CH_3$ or $CF_3$. In some embodiments of formula (II)-(VI), $R^2$, $R^3$ or $R^4$ is selected from ($C_1$-$C_5$)alkyl, substituted ($C_1$-$C_5$)alkyl, ($C_1$-$C_3$)haloalkyl and halogen. In some embodiments of formula (II)-(VI), $R^2$, $R^3$ and $R^4$ are each H.

In some embodiments of formula (Ia), the compound is of formula (VII):

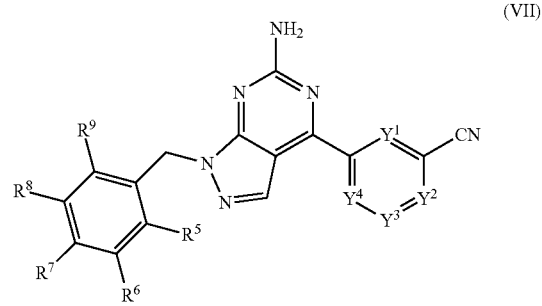

wherein:
$Y^1$ to $Y^4$ are independently selected from $CR^{10}$ and N, wherein at least three of $Y^1$ to $Y^4$ are independently $CR^{10}$;
$R^5$ to $R^9$ and each $R^{10}$ are independently selected from H, ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$)alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;
or a solvate, a hydrate, a prodrug, and/or a stereoisomer thereof, or a pharmaceutically acceptable salt thereof.

In some embodiments of formula (VII), one of $Y^1$ to $Y^4$ is N.

In some embodiments of formula (VII), $R^5$ to $R^9$ and each $R^{10}$ are independently selected from H, ($C_1$-$C_5$)alkyl, substituted ($C_1$-$C_5$)alkyl, ($C_1$-$C_3$)haloalkyl, ($C_1$-$C_5$)alkoxy, substituted ($C_1$-$C_5$)alkoxy, —$NH_2$, substituted amino, halogen, and hydroxyl. In some embodiments of formula (VII), $R^5$ to $R^9$ and each $R^{10}$ are independently selected from H, $NH_2$, F, $CH_3$, and $CF_3$.

In some embodiments of formula (VII), the compound is of formula (VIII):

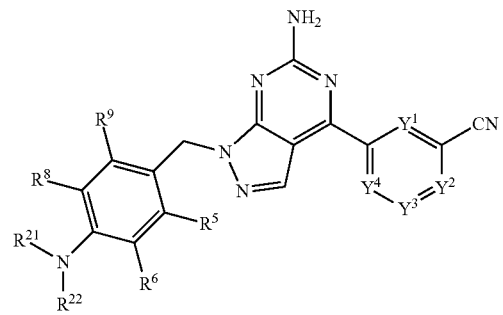

wherein:
one of $Y^1$ to $Y^4$ is N; and
$R^{21}$ and $R^{22}$ are independently selected from H, ($C_1$-$C_8$) alkyl, substituted ($C_1$-$C_8$)alkyl, $SO_2R^{30}$, and $COR^{30}$, wherein $R^{30}$ is ($C_1$-$C_8$)alkyl, or substituted ($C_1$-$C_8$) alkyl;
or a solvate, a hydrate, a prodrug, and/or a stereoisomer thereof, or a pharmaceutically acceptable salt thereof.

In some embodiments of formula (VIII), $R^{21}$ and $R^{22}$ are each H.

In some embodiments of formula (VIII), $R^5$, $R^6$, $R^8$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (VIII), $R^5$, $R^6$, $R^8$ and $R^9$ are independently selected from H, F, $CH_3$, and $CF_3$. In some embodiments of formula (VIII), $R^5$, $R^6$, $R^8$ and $R^9$ are each H.

In some embodiments of formula (VIII), the compound is selected from:

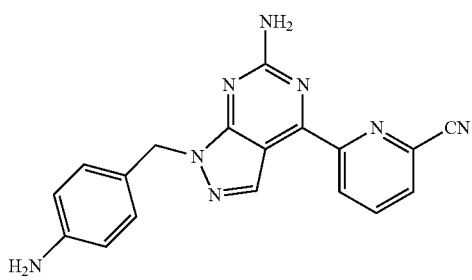 [SMILES: N#Cc1cccc(-c2nc(N)nc3c2cnn3Cc2ccc(N)cc2)n1]

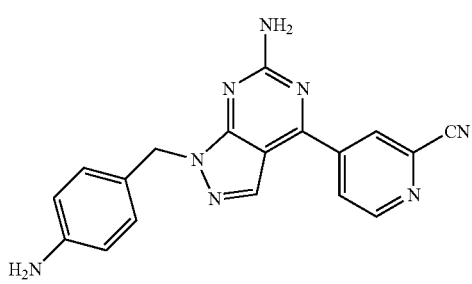 [SMILES: N#Cc1cc(-c2nc(N)nc3c2cnn3Cc2ccc(N)cc2)ccn1]

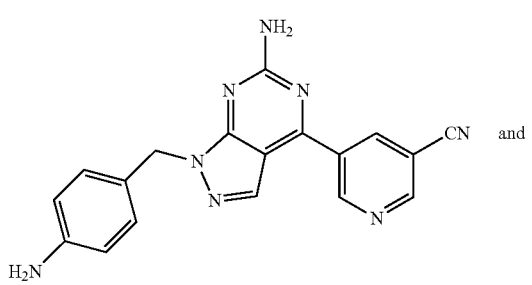

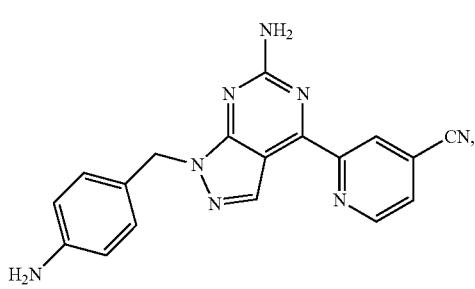

or a solvate, a hydrate, a prodrug, and/or a stereoisomer thereof, or a pharmaceutically acceptable salt thereof.

In some embodiments of formula (VIII), the compound is of formula (IX):

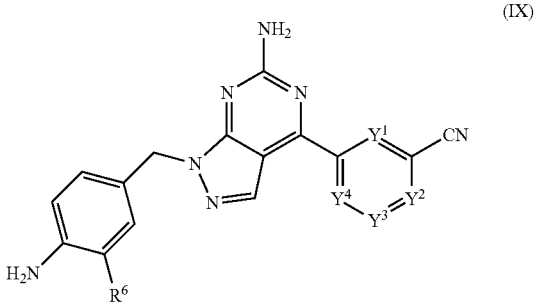

or a solvate, a hydrate, a prodrug, and/or a stereoisomer thereof, or a pharmaceutically acceptable salt thereof.

In some embodiments of formula (IX), $R^6$ is selected from $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (IX), $R^6$ is selected from $(C_1-C_5)$alkyl, substituted $(C_1-C_5)$alkyl, and $(C_1-C_3)$haloalkyl. In some embodiments of formula (IX), $R^6$ is $CH_3$ or $CF_3$.

In some embodiments of formula (IX), the compound is selected from:

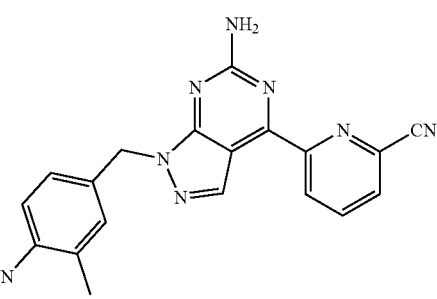

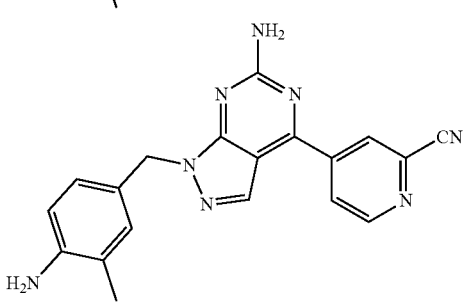

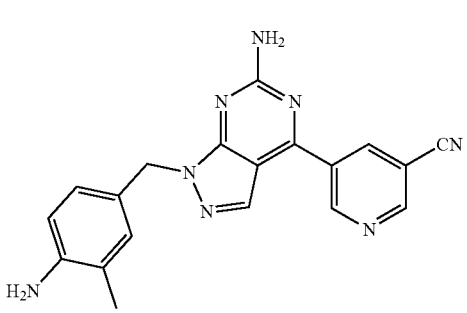

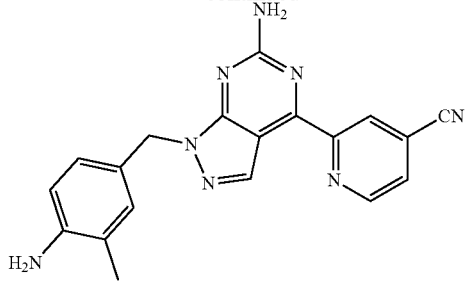

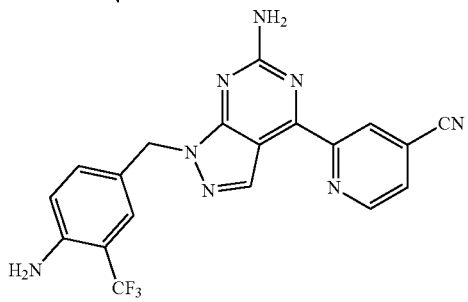

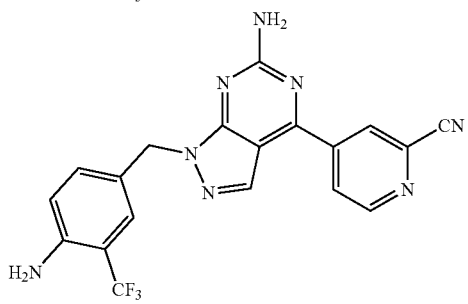

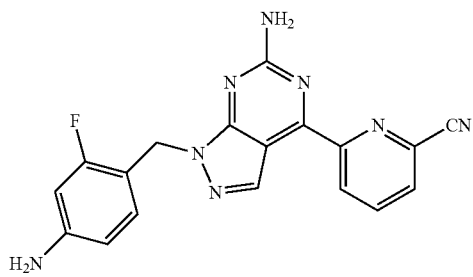 [SMILES: N#Cc1cccc(-c2nc(N)nc3c2cnn3Cc2ccc(N)cc2F)n1]

or a solvate, a hydrate, a prodrug, and/or a stereoisomer thereof, or a pharmaceutically acceptable salt thereof.

In some embodiments of formula (VIII), is of formula (X):

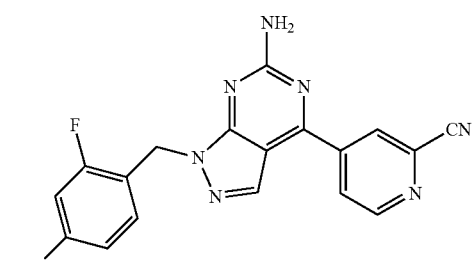

or a solvate, a hydrate, a prodrug, and/or a stereoisomer thereof, or a pharmaceutically acceptable salt thereof.

In some embodiments of formula (X), $R^5$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (X), $R^5$ and $R^9$ are independently selected from H and halogen. In some embodiments of formula (X), $R^5$ is F. In some embodiments of formula (X), $R^9$ is F. In some embodiments of formula (X), $R^5$ and $R^9$ are each F. In some embodiments of formula (X), $R^5$ is H and $R^9$ is F.

In some embodiments of formula (X), the compound is selected from:

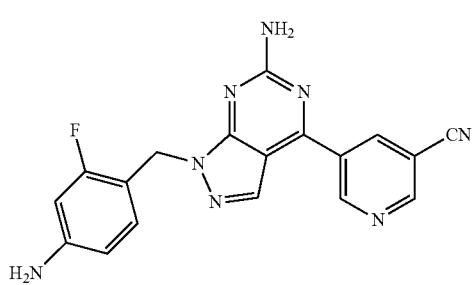 [SMILES: N#Cc1cncc(-c2nc(N)nc3c2cnn3Cc2ccc(N)cc2F)c1]

-continued

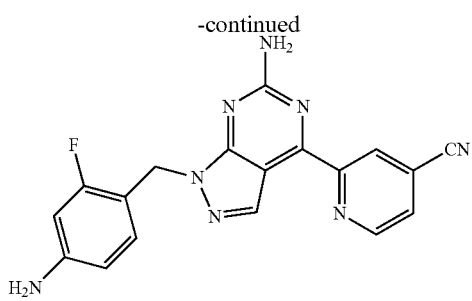

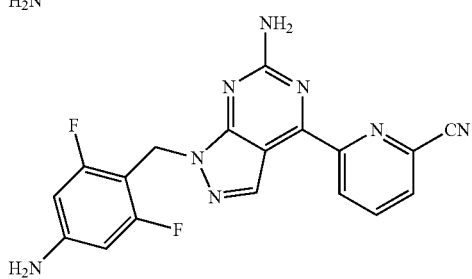

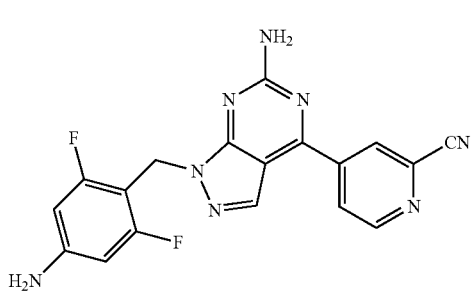 [SMILES: N#Cc1cc(-c2nc(N)nc3c2cnn3Cc2c(F)cc(N)cc2F)ccn1]

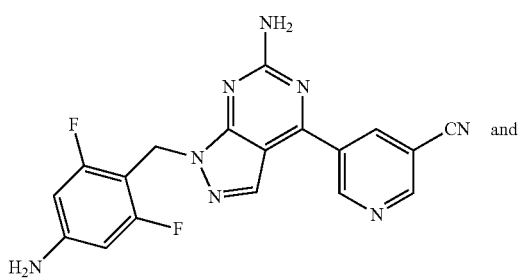

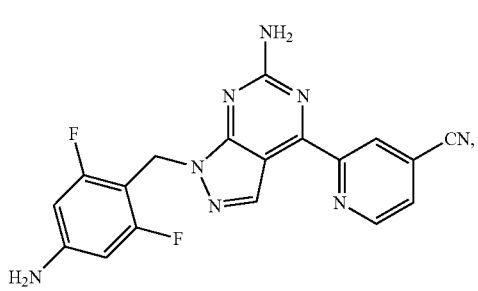

or a solvate, a hydrate, a prodrug, and/or a stereoisomer thereof, or a pharmaceutically acceptable salt thereof.

In some embodiments of formula (VII), the compound is of formula (XI):

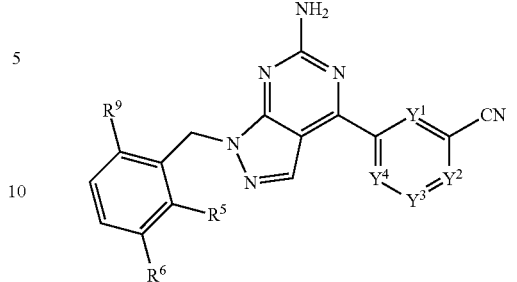

(XI)

or a solvate, a hydrate, a prodrug, and/or a stereoisomer thereof, or a pharmaceutically acceptable salt thereof.

In some embodiments of formula (XI), $R^5$, $R^6$ and $R^9$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —$NH_2$, substituted amino, halogen, and hydroxyl. In some embodiments of formula (XI), $R^6$ is selected from H, $(C_1-C_5)$alkyl, substituted $(C_1-C_5)$alkyl, and $(C_1-C_3)$haloalkyl. In some embodiments of formula (XI), $R^6$ is $CH_3$ or $CF_3$. In some embodiments of formula (XI), $R^6$ is H.

In some embodiments of formula (XI), $R^5$ and $R^9$ are independently selected from H and halogen. In some embodiments of formula (XI), $R^5$ is F. In some embodiments of formula (XI), $R^9$ is F. In some embodiments of formula (XI), $R^5$ and $R^9$ are each F. In some embodiments of formula (XI), $R^5$ is F and $R^9$ is H.

In some embodiments of formula (XI), the compound is selected from:

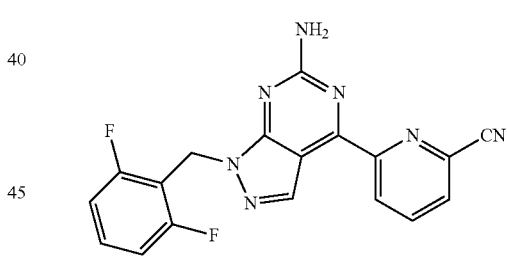

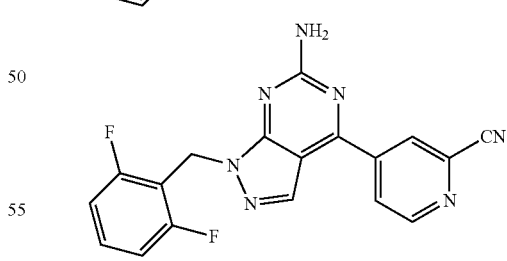

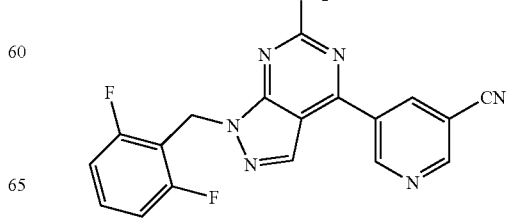

and

-continued

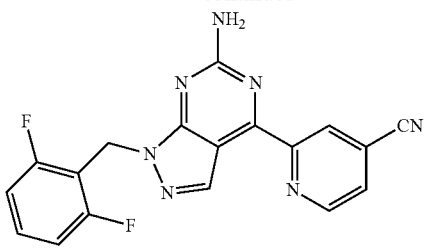 [SMILES: N#Cc1ccnc(-c2nc(N)nc3c2cnn3Cc2c(F)cccc2F)c1]

or a solvate, a hydrate, a prodrug, and/or a stereoisomer thereof, or a pharmaceutically acceptable salt thereof.

In some embodiments of formula (VII), the compound is of formula (XIV):

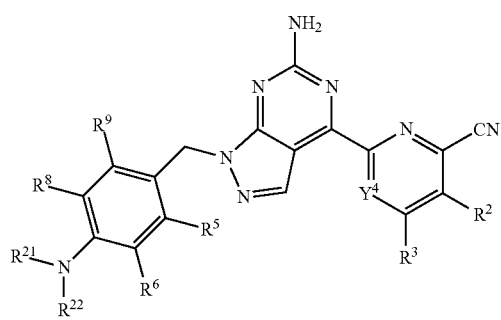

(XIV)

wherein:

Y$^4$ is CR$^4$ or N;

R$^1$ to R$^4$ are independently selected from H, (C$_1$-C$_8$)alkyl, substituted (C$_1$-C$_8$)alkyl, (C$_2$-C$_8$)alkenyl, substituted (C$_2$-C$_8$)alkenyl, (C$_2$-C$_8$)alkynyl, substituted (C$_2$-C$_8$) alkynyl, (C$_1$-C$_3$)haloalkyl, (C$_1$-C$_8$)alkoxy, substituted (C$_1$-C$_8$)alkoxy, —CONH$_2$, substituted amido, —NH$_2$, substituted amino, —CO$_2$H, cyano, halogen, hydroxyl, —NO$_2$, —SO$_3$H, —SO$_2$NH$_2$, substituted sulfonamide, and thiol; and R$^{21}$ and R$^{22}$ are independently selected from H, (C$_1$-C$_8$) alkyl, substituted (C$_1$-C$_8$)alkyl, SO$_2$R$^{30}$, and COR$^{30}$, wherein R$^{30}$ is (C$_1$-C$_8$)alkyl, or substituted (C$_1$-C$_8$) alkyl, or a solvate, a hydrate, a prodrug, and/or a stereoisomer thereof, or a pharmaceutically acceptable salt thereof.

In some embodiments of formula (XIV), R$^5$, R$^6$, R$^8$ and R$^9$ are independently selected from H, (C$_1$-C$_5$)alkyl, substituted (C$_1$-C$_5$)alkyl, (C$_1$-C$_3$)haloalkyl, (C$_1$-C$_5$)alkoxy, substituted (C$_1$-C$_5$)alkoxy, halogen, and hydroxyl.

In some embodiments of formula (XIV), R$^{21}$ and R$^{22}$ are each H.

In some embodiments of formula (XIV), R$^2$ to R$^4$ are each H; and R$^1$ is selected from H, (C$_1$-C$_5$)alkyl, substituted (C$_1$-C$_5$)alkyl, (C$_1$-C$_3$)haloalkyl, (C$_1$-C$_5$)alkoxy, substituted (C$_1$-C$_5$)alkoxy, halogen, and hydroxyl. In some embodiments of formula (XIV), R$^1$ is selected from H, F, CH$_3$, and CF$_3$.

In some embodiments of formula (XIV), the compound is of formula (XV):

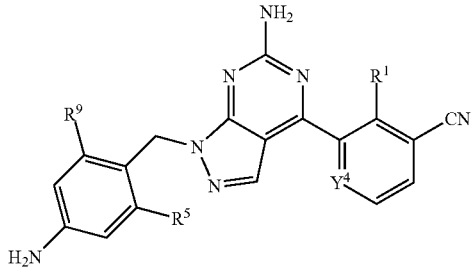

(XV)

or a solvate, a hydrate, a prodrug, and/or a stereoisomer thereof, or a pharmaceutically acceptable salt thereof.

In some embodiments of formula (XV), R$^5$ and R$^9$ are independently selected from H, (C$_1$-C$_5$)alkyl, substituted (C$_1$-C$_5$)alkyl, (C$_1$-C$_3$)haloalkyl, (C$_1$-C$_5$)alkoxy, substituted (C$_1$-C$_5$)alkoxy, halogen, and hydroxyl. In some embodiments of formula (XV), R$^5$ and R$^9$ are independently selected from H and halogen. In some embodiments of formula (XV), R$^5$ is F. In some embodiments of formula (XV), R$^9$ is F. In some embodiments of formula (XV), R$^5$ and R$^9$ are each F. In some embodiments of formula (XV), R$^5$ is H and R$^9$ is F.

In some embodiments of formula (XV), 10 is selected from H, (C$_1$-C$_5$)alkyl, substituted (C$_1$-C$_5$)alkyl, (C$_1$-C$_3$) haloalkyl, (C$_1$-C$_5$)alkoxy, substituted (C$_1$-C$_5$)alkoxy, halogen, and hydroxyl. In some embodiments of formula (XV), R$^1$ is selected from H, F, CH$_3$, and CF$_3$.

In some embodiments of formula (XV), Y$^4$ is CH. In some embodiments of formula (XV), Y$^4$ is N.

In some embodiments of formula (XV), the compound is selected from:

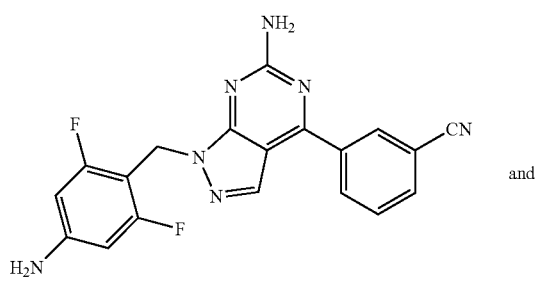

and

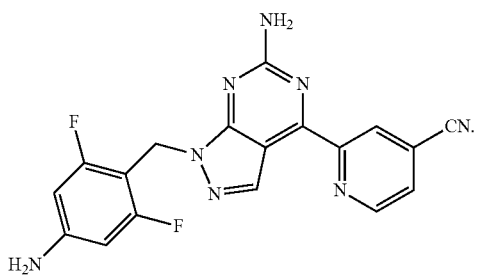

or a solvate, a hydrate, a prodrug, and/or a stereoisomer thereof, or a pharmaceutically acceptable salt thereof.

In some embodiments of formula (XIV), the compound is of formula (XVI):

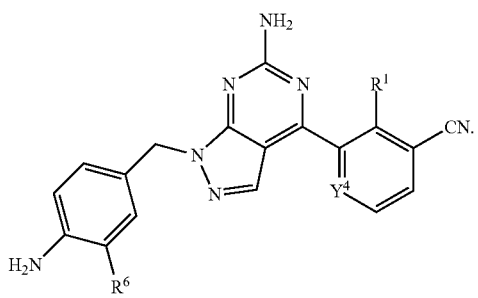

(XVI)

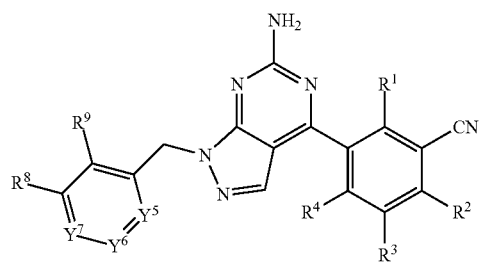

(XII)

or a solvate, a hydrate, a prodrug, and/or a stereoisomer thereof, or a pharmaceutically acceptable salt thereof.

In some embodiments of formula (XVI), $R^6$ is selected from $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XVI), $R^6$ is selected from $(C_1-C_5)$alkyl, substituted $(C_1-C_5)$alkyl, and $(C_1-C_3)$haloalkyl. In some embodiments of formula (XVI), $R^6$ is $CH_3$ or $CF_3$.

In some embodiments of formula (XVI), $R^1$ is selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, halogen, and hydroxyl. In some embodiments of formula (XVI), $R^1$ is selected from H, F, $CH_3$, and $CF_3$.

In some embodiments of formula (XVI), $Y^4$ is CH. In some embodiments of formula (XVI), $Y^4$ is N.

In some embodiments of formula (XVI), the compound is selected from:

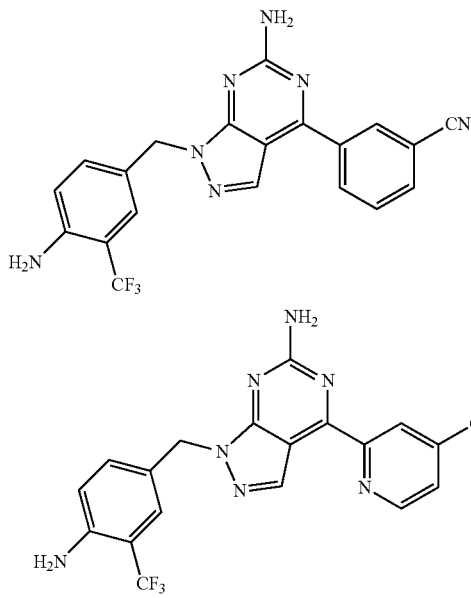

and or a solvate, a hydrate, a prodrug, and/or a stereoisomer thereof, or a pharmaceutically acceptable salt thereof.

In some embodiments of formula (I)-(Ia), the compound is of formula (XII):

wherein:
$Y^5$ to $Y^7$ are each independently $CR^{20}$ or N, wherein one of $Y^5$ to $Y^7$ is N; and
$R^1$ to $R^4$, $R^8$, $R^9$ and each $R^{20}$ are independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol.

In some embodiments of formula (XII), $Y^5$ is N. In some embodiments of formula (XII), $Y^6$ is N. In some embodiments of formula (XII), $Y^7$ is N.

In some embodiments of formula (XII), $R^8$, $R^9$ and each $R^{20}$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —$NH_2$, substituted amino, halogen, and hydroxyl.

In some embodiments of formula (XII), $R^8$, $R^9$ and each $R^{20}$ are independently selected from H, $NH_2$, F, $CH_3$, and $CF_3$.

In some embodiments of formula (XII), $R^1$ to $R^4$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —$NH_2$, substituted amino, halogen, and hydroxyl. In some embodiments of formula (XII), $R^1$ to $R^4$ are independently selected from H, $(C_1-C_5)$alkyl, substituted $(C_1-C_5)$alkyl, $(C_1-C_3)$haloalkyl and halogen.

In some embodiments of formula (I)-(Ia), the compound is of formula (XIII):

(XIII)

wherein:
$Y^5$ to $Y^7$ are each independently $CR^{20}$ or N, wherein one of $Y^5$ to $Y^7$ is N; and
$R^8$, $R^9$, each $R^{19}$, and each $R^{20}$ are independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —NH₂, substituted amino, —CO₂H, cyano, halogen, hydroxyl, —NO₂, —SO₃H, —SO₂NH₂, substituted sulfonamide, and thiol.

In some embodiments of formula (XIII), $Y^5$ is N. In some embodiments of formula (XIII), $Y^6$ is N. In some embodiments of formula (XIII), $Y^7$ is N.

In some embodiments of formula (XIII), $R^8$, $R^9$ and each $R^{20}$ are independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —NH₂, substituted amino, halogen, and hydroxyl. In some embodiments of formula (XIII), $R^8$, $R^9$ and each $R^{20}$ are independently selected from H, NH₂, F, CH₃, and CF₃. In some embodiments of formula (XIII), each $R^{10}$ is independently selected from H, $(C_1-C_5)$alkyl, substituted $(C_1-C_5)$alkyl, $(C_1-C_3)$haloalkyl, $(C_1-C_5)$alkoxy, substituted $(C_1-C_5)$alkoxy, —NH₂, substituted amino, halogen, and hydroxyl.

In some embodiments of formula (XIII), $Y^1$ is $CR^{10}$.

In some embodiments of formula (XIII), $R^{10}$ is H. In some embodiments of formula (XIII), $R^{19}$ is selected from $(C_1-C_5)$alkyl, substituted $(C_1-C_5)$alkyl, $(C_1-C_3)$haloalkyl and halogen. In some embodiments of formula (XIII), $R^{10}$ is F, CH₃ or CF₃.

In some embodiments of formula (XIII), $Y^1$ to $Y^4$ are each $CR^{10}$.

In some embodiments of formula (XIII), each $R^{10}$ is independently selected from $(C_1-C_5)$alkyl, substituted $(C_1-C_5)$alkyl, $(C_1-C_3)$haloalkyl and halogen.

In some embodiments of formula (XIII), $Y^1$ to $Y^4$ are each CH. In some embodiments of formula (XIII), one and only one of $Y^1$ to $Y^4$ is N. In some embodiments of formula (XIII), $Y^1$ is N. In some embodiments of formula (XIII), $Y^2$ is N. In some embodiments of formula (XIII), $Y^3$ is N. In some embodiments of formula (XIII), $Y^4$ is N.

In some embodiments of formula (I), the compound is selected from: 3-(6-amino-1-(4-aminobenzyl)-1H-pyrazolo[3,4-d]pyrimidine-4-yl)-benzonitrile; 3-(6-amino-1-(4-aminobenzyl)-1H-pyrazolo[3,4-d]pyrimidine-4-yl)-2-methyl-benzonitrile; 3-(6-amino-1-(4-amino-3-methylbenzyl)-1H-pyrazolo[3,4-d]pyrimidine-4-yl)-2-fluorobenzonitrile; 3-(6-amino-1-(4-amino-3-(trifluoromethyl)benzyl)-1H-pyrazolo[3,4-d]pyrimidine-4-yl)benzonitrile; and 3-(6-amino-1-(4-aminobenzyl)-1H-pyrazolo[3,4-d]pyrimidine-4-yl)-2-fluorobenzonitrile.

It is understood that all variations of salts, and/or solvates, hydrates, prodrugs and/or stereoisomers of the compounds described herein e.g., of formula (I)-(XVI), or shown in Table 1 are meant to be encompassed by the present disclosure. Accordingly, any of the compounds described herein may also be referred to as a compound of formula (I)-(XVI) or a solvate, a hydrate, a prodrug, and/or a stereoisomer thereof, or a pharmaceutically acceptable salt thereof.

In some embodiments, the compound is represented by the structure of one of the compounds in Table 1, or a solvate, a hydrate, a prodrug, and/or a stereoisomer thereof, or a salt (e.g., a pharmaceutically acceptable salt) thereof. The present disclosure is meant to encompass, a compound of any one of Table 1, or a salt thereof, and/or a solvate, a hydrate, a prodrug thereof, a single stereoisomer, a mixture of stereoisomers and/or an isotopically labelled form thereof. For example, salts of a solvate, hydrate, prodrug and/or stereoisomer form of any of the compounds described herein (e.g., of formula (I)-(XVI)) or shown in Table 1 are meant to be encompassed by the present disclosure.

TABLE 1

Exemplary A2A and/or A1 Receptor Antagonist Compounds

| Compound No. | Compounds of Formula (Ia) |
|---|---|
| 201 | [structure] |
| 202 | [structure] |
| 203 | [structure] |
| 204 | [structure] |
| 205 | [structure] |

TABLE 1-continued
Exemplary A2A and/or A1 Receptor Antagonist Compounds
| Compound No. | Compounds of Formula (Ia) |
|---|---|
| 206 | 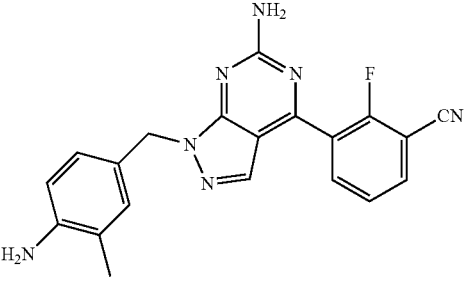 |
| 207 | 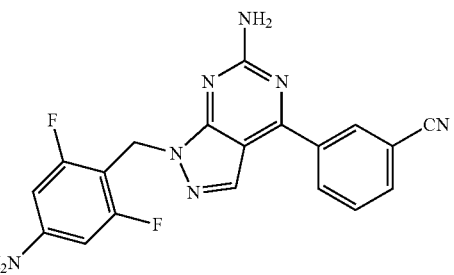 |
| 208 | 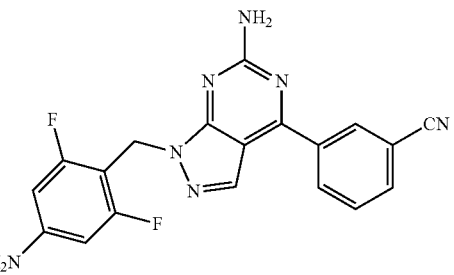 |
| 209 | 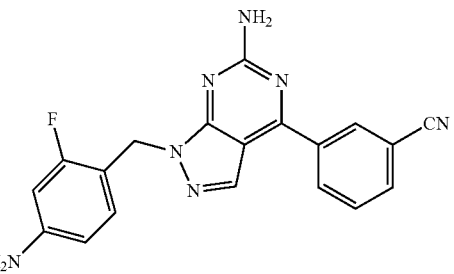 |
| 210 | 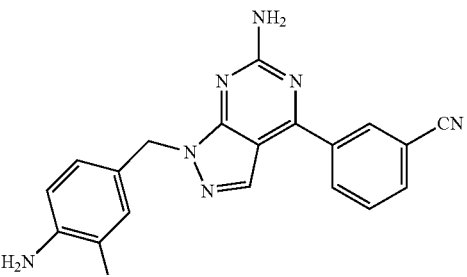 |
| 211 | 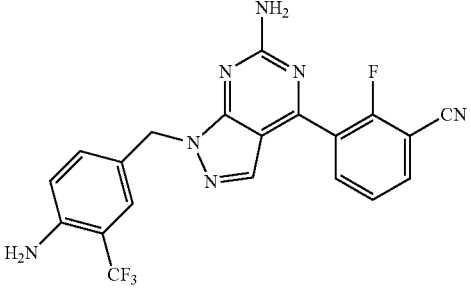 |
| 212 | 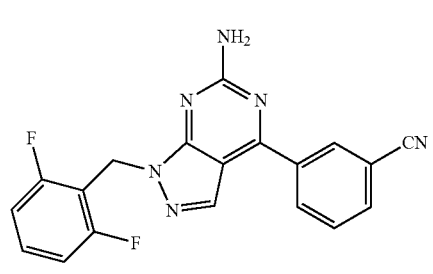 |
| 213 | 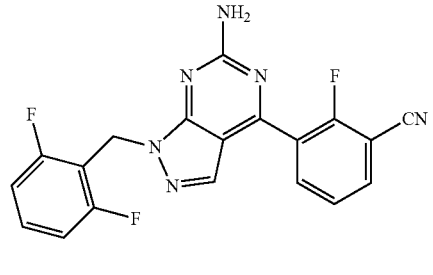 |
| 214 | 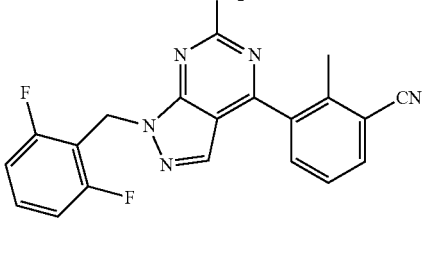 |
| 215 | 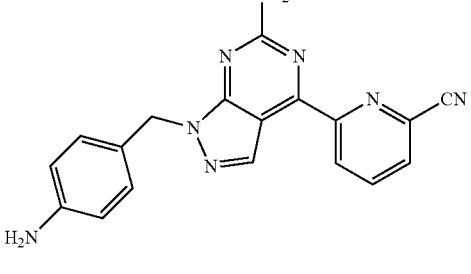 |

TABLE 1-continued

Exemplary A2A and/or A1 Receptor Antagonist Compounds

| Compound No. | Compounds of Formula (Ia) |
|---|---|
| 216 | [structure] |
| 217 | [structure] |
| 218 | [structure] |
| 219 | [structure] |
| 220 | [structure] |
| 221 | [structure] |
| 222 | [structure] |
| 223 | [structure] |
| 224 | [structure] |
| 225 | [structure] |

TABLE 1-continued

Exemplary A2A and/or A1 Receptor Antagonist Compounds

| Compound No. | Compounds of Formula (Ia) |
|---|---|
| 226 | (structure) |
| 227 | (structure) |
| 228 | (structure) |
| 229 | (structure) |
| 230 | (structure) |
| 231 | (structure) |
| 232 | (structure) |
| 233 | (structure) |
| 234 | (structure) |
| 235 | (structure) |

TABLE 1-continued

Exemplary A2A and/or A1 Receptor Antagonist Compounds

| Compound No. | Compounds of Formula (Ia) |
|---|---|
| 236 | (structure: pyrazolo[3,4-d]pyrimidine with NH$_2$, substituted with 4-amino-3-trifluoromethylbenzyl group on N, and 2-cyanopyridin-4-yl group) |
| 237 | (structure: pyrazolo[3,4-d]pyrimidine with NH$_2$, substituted with 4-amino-3-trifluoromethylbenzyl group on N, and 5-cyanopyridin-3-yl group) |
| 238 | (structure: pyrazolo[3,4-d]pyrimidine with NH$_2$, substituted with 4-amino-3-trifluoromethylbenzyl group on N, and 6-cyanopyridin-2-yl group) |

Uses of analogs, salts, isomers, prodrugs of the above-described A2A and/or A1 receptor antagonist compounds described in WO 2021099837 A of which the content is incorporated herein by reference in its entirety, in preventing and/or treating CNS disorders or neurodegenerative disorders are also encompassed in the instant application. In embodiments, the CNS disorders or neurodegenerative disorders are associated with A2A and/or A1 receptor.

Pharmaceutical Compositions

Compounds of the present disclosure may be formulated in pharmaceutical compositions. The pharmaceutical composition can include one or more such A2A and/or A1 receptor antagonist compounds (e.g., as described herein) and at least one excipient (e.g., a pharmaceutically acceptable excipient).

The compounds described herein can find use in pharmaceutical compositions for administration to a subject in need thereof in a variety of therapeutic applications where inhibition or antagonism of the activity of A2A and/or A1 receptor is desirable.

Accordingly, in embodiments, the present disclosure provides pharmaceutical compositions comprising at least one compound described herein, a pharmaceutically acceptable salt thereof, or a prodrug thereof, and at least one pharmaceutically acceptable excipient. The phrase "pharmaceutically acceptable excipient," refers any ingredient other than the inventive compounds described herein (for example, a vehicle capable of suspending or dissolving the active compound, or any other convenient pharmaceutically acceptable carriers, excipients or additives) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, dispensing, or dispersing agents, sweeteners, and waters of hydration. In some embodiments, the pharmaceutical composition comprises a compound as described herein, a pharmaceutically acceptable salt thereof, or a prodrug thereof in a therapeutically effective amount.

The pharmaceutical composition may be formulated according to any convenient methods, and may be prepared in various forms for oral administration such as tablets, pills, powders, nanoparticles, capsules, syrups, suspensions, emulsions and microemulsions, or in forms for non-oral administration such as preparations for intramuscular, intravenous or subcutaneous administration. The pharmaceutical compositions provided herein can be administered by a variety of routes including, but not limited to, oral (enteral) administration, parenteral (by injection) administration, rectal administration, transdermal administration, intradermal administration, intrathecal administration, subcutaneous (SC) administration, intravenous (IV) administration, intramuscular (IM) administration, and intranasal administration.

In a specific example, the pharmaceutical composition could contain a pharmaceutically allowed carrier, excipient, or additive. The pharmaceutical composition could be produced as medicine in the conventional method, and could be produced as various oral medicine such as tablet, pill, powder, capsule, syrup, emulsion, micro-emulsion, and so on, or could be produced as non-oral medicine such as muscular injection, vascular injection, or subcutaneous injection.

The term "carrier," "adjuvant," "vehicle," and "excipients" are exchangeably used herein, and the compound of this disclosure is administered with the carrier. The carrier is a solid carrier or a flowable carrier. Suitable pharmaceutical carriers include those described in Remington: The Science and Practice of Pharmacy, 21st Ed., Lippincott Williams & Wilkins (2005).

If the pharmaceutical composition is produced in the form of an oral medicine, examples of the used additive or carrier could include cellulose, silicic calcium, corn starch, lactose, sucrose, dextrose, phosphoric acid calcium, stearic acid, stearic acid magnesium, stearic acid calcium, gelatin, talc, surfactant, suspension, emulsifying agent, diluting agent, and so on. If the pharmaceutical composition of this disclosure is produced in the form of an injection, the additives or carrier could include water, saline water, glucose aqueous solution, similar sugar-soluble solution, alcohol, glycol, ether (e.g., polyethylene glycol 400), oil, fatty acid, fatty acid ester, glyceride, surfactant, suspension, emulsifying agent, and so on.

In some embodiments, the pharmaceutical compositions are formulated for parenteral administration to a subject in need thereof. In some parenteral embodiments, the pharmaceutical compositions are formulated for intravenous administration to a subject in need thereof. In some parenteral embodiments, the pharmaceutical compositions are formulated for subcutaneous administration to a subject in need thereof.

Methods of Modulating A2A and/or A1 Receptor

Aspects of the present disclosure include methods of modulating the activity of A2A and/or A1 receptor in a biological system or sample. In some embodiments, modulating the activity of A2A and/or A1 receptor refers to inhibiting an A2A and/or A1 receptor in a sample. In some embodiments, modulating the activity of A2A and/or A1 receptor refers to antagonizing the activity of an A2A and/or A1 receptor in a cell or biological system.

In some embodiments, the method includes contacting a sample with a compound of this disclosure which can modulate A2A and/or A1 receptor activity. In some embodiments, the method includes contacting a cell or biological system with a compound of this disclosure which can modulate A2A and/or A1 receptor activity.

The present disclosure provides compounds having A2A and/or A1 receptor modulating activity, e.g., A2A and/or A1 receptor inhibition and/or antagonistic activity. In some embodiments, the compound has A2A receptor inhibition and/or antagonistic activity. In some embodiments, the compound has A2A and A1 receptor inhibition and/or antagonistic activity. In some embodiments, the compound has A1 receptor inhibition and/or antagonistic activity. The ability of the compounds to modulate A2A and/or A1 receptor activity may be characterized using a variety of assays, e.g., by an A2A and/or A1 receptor binding assay and/or an A2A and/or A1 receptor functional assay. For example, the experimental section describes A2A receptor binding assays. Exemplary compounds of this disclosure were assessed, and $K_i$ values determined, to show that the compounds of this disclosure can provide specific binding to human A2A receptor in an assay system. In addition, the experimental section describes A2A functional assays involving monitoring cAMP signals produced in a human recombinant A2A receptor stable cell line. Exemplary compounds of this disclosure were assessed, and $IC_{50}$ values obtained, indicating that the compounds can antagonize human A2A receptor in an assay system.

Aspects of the present disclosure include methods of modulating (e.g., inhibiting or antagonizing) A2A and/or A1 receptor using a compound described herein. Such methods may include methods of modulating A2A and/or A1 receptor in biological systems by contacting such systems with compounds (e.g., compounds having structures according to Formula (I)-(XVI) or the compounds of Table 1). Biological systems may include, but are not limited to, cells, tissues, organs, bodily fluids, organisms, non-mammalian subjects, and mammalian subjects (e.g., humans, dogs, cats, mice, rats, rabbits, guinea pigs, sheep, goats, cows, horses, primates, such as monkeys, chimpanzees, and apes, and, in particular, humans).

In some embodiments, the method of inhibiting or antagonizing A2A and/or A1 receptor comprises contacting a biological system or sample comprising A2A and/or A1 receptor with an effective amount of any of the compounds or a pharmaceutically acceptable salt thereof as described herein, or a pharmaceutical composition as described herein to inhibit or antagonize the A2A receptor. In certain embodiments, the biological system or sample is in vitro. In another embodiment, the biological system or sample is in vivo. In some embodiments, the sample is a cell sample. In some embodiments, the A2A and/or A1 receptor is cell membrane bound.

In some embodiments, the compound is an A2A receptor antagonist that exhibits a desirable level of inhibition activity at A1 receptor. In some embodiments, the compound is a dual antagonist of the A2A receptor and the A1 receptor. In some embodiments, a desirable level of A1 receptor inhibition activity refers to compound having a Ki value at a human A1 receptor in a cell model (e.g., as assessed in Example 2.1) that is 1 mM or lower, such as 300 µM or lower, 100 µM or lower, 30 µM or lower, 10 µM or lower, 3 µM or lower, or 1 µM or lower. In some embodiments, the compound of this disclosure exhibits inhibition activity for A2A receptor and A1 receptor. Example 2, Table 2, of the experimental section, provides A2A and A1 receptor inhibition data which indicates compounds of this disclosure can have potent activity as dual antagonists. In such cases, the compounds can find use in treatment of CNS and neurodegenerative diseases.

Cancer and Immuno-Oncology

The present disclosure provides a method of treating or preventing cancer in a subject using the subject compounds as therapeutic agents, and compositions including the compounds. Any cancer for which an A2A receptor antagonist are thought to be useful by those of ordinary skill in the art are contemplated as cancers treatable by this embodiment, either as a monotherapy or in combination with other therapeutic agents discussed below.

The illness subject to prevention or treatment by the aforementioned pharmaceutical composition, which is "cancer," refers collectively to the illness caused by cells wherein cells have aggressive characteristics such as dividing and growing by ignoring normal growth limit, invasive characteristics whereby cells invade the surrounding tissues, and metastatic characteristics whereby cells spread to other areas of the body. In some embodiments, the cancer is a solid tumor cancer. Cancers which are the object of prevention or therapy using the compounds and pharmaceutical compositions of this disclosure include, but are not limited to, lung cancer, breast cancer, prostate cancer, ovarian cancer, solenoma, cervical cancer, bladder cancer, head and neck cancer, renal cell carcinoma, cancer of the esophagus, pancreatic cancer, brain cancer, liver cancer, leukemia, lymphoma, melanoma, multiple myeloma, Ewing's sarcoma, osteosarcoma, colorectal neoplasm, cholangiocarcinoma, choriocarcinoma, mouth cancer, neuroblastoma, skin cancer, testicular cancer, stromal tumor, germ cell tumor, and thyroid cancer.

In some embodiments, the cancer is cancer of the kidney, breast, lung, or liver. In some embodiments, the cancer is a solid tumor cancer. In some embodiments, the liver cancer is hepatocellular carcinoma (HCC). In some embodiments, the lung cancer is non-small cell lung carcinoma (NSCLC). In some embodiments, the cancer is a solid tumor cancer.

In some embodiments, the method further comprises identifying a subject suffering from or having cancer.

The compounds of this disclosure can be administered alone or in combination with one or more additional agents described herein. Accordingly, aspects of the methods include co-administering to the subject an effective amount of a compound or composition of this disclosure and an effective amount of an additional active agent. The compound and additional active agent can be administered concurrently or sequentially.

In some embodiments of the methods, the additional active agent is an anticancer agent selected from anti-angiogenesis agent, anti-inflammatory agent, immune checkpoint inhibitor, poly ADP ribose polymerase (PARP) inhibitor, chemotherapeutic agent, and immunity anticancer agent.

Given the immunosuppressive role of adenosine, the administration of an A2A receptor antagonist of this disclosure can enhance the efficacy of an immunotherapy, such as an immune checkpoint inhibitor therapy. In some embodiments, the additional active agent is an immune checkpoint inhibitor selected from CTLA-4 inhibitor, PD-1 inhibitors, and PD-L1 inhibitor.

In some embodiments, the immune checkpoint inhibitor is an antibody or antibody fragment. In some embodiments, the additional therapeutic agent is an anti-PD-1 antibody. In another embodiment, the additional therapeutic agent is an anti-PD-L1 antibody. In some embodiments, the additional therapeutic agent is selected from pembrolizumab, nivolumab, atezolizumab, durvalumab, and avelumab.

Inflammatory Disease

The present disclosure provides a method of treating or preventing an inflammatory disease in a subject using the subject compounds as therapeutic agents, and compositions including the compounds. Any inflammatory diseases for which an A2A receptor antagonist are thought to be useful by those of ordinary skill in the art are contemplated as diseases treatable using compounds of this disclosure, either as a monotherapy or in combination with other therapeutic agents (e.g., as described herein).

In some embodiments, the method includes administering to a subject having an inflammatory disease a therapeutically effective amount of an A2A and/or A1 receptor antagonist compound (e.g., as described herein). In some embodiments, the inflammatory disease is a chronic inflammatory disease, such as rheumatoid arthritis (RA). In some embodiments, the inflammatory disease is an acute inflammatory disease.

In some embodiments, the method further comprises identifying a subject suffering from or at risk of an inflammatory disease.

In some embodiments, the method further comprises identifying an underlying disease or condition associated with the inflammatory disease.

CNS and Neurodegenerative Disorder or Diseases

The present disclosure provides a method selected from (i) a method of treating a central nerve system (CNS) disorder selected from the group consisting of Huntington's disease, Parkinson's disease, Alzheimer's disease, schizophrenia, mild-cognitive impairment, attention deficit hyperactivity disorder (ADHD), multiple sclerosis (MS), vascular dementia, amyotrophic lateral sclerosis (ALS), depression, schizophrenia, and epilepsy; (ii) a method of treating an injury or disease that results in neuronal degeneration selected from the group consisting of closed head injuries, blunt trauma, penetrating trauma, hemorrhagic stroke, ischemic stroke, glaucoma, cerebral ischemia, spinal cord injury, ageing, and neuronal damage caused by surgical procedures (wherein the injury may be a primary nervous system injury selected from the group comprising closed head injuries, blunt trauma, penetrating trauma, hemorrhagic stroke, ischemic stroke, glaucoma, cerebral ischemia, spinal cord injury, ageing, and neuronal damage caused by surgical procedures); or (iii) a method of treating a movement disorder, wherein the method comprises administering to a subject in need thereof an effective amount of an adenosine receptor (e.g., A2A and/or A1) antagonist compound of the formula (Ia) described herein. In the above mentioned methods, the A2A and/or A1 antagonist compound may be a compound of formula (I)-(XVI). In the above mentioned methods, the CNS disorder or neurodegenerative diseases may be associated with an adenosine receptor (e.g., A2A and/or A1 receptor). In some embodiments, the CNS disorder or neurodegenerative diseases may be associated with the A2A receptor.

Aspects of the present disclosure include methods of treating a subject for a therapeutic indication of interest using compounds and/or compositions disclosed herein. The term "therapeutic indication" refers to any symptom, condition, disorder, or disease that may be alleviated, stabilized, improved, cured, or otherwise addressed in a subject by some form of treatment or other therapeutic intervention (e.g., through A2A and/or A1 receptor antagonist administration). Therapeutic indications associated with modulation of A2A and/or A1 receptor biological activity and/or dysfunction are referred to herein as "adenosine receptor-associated disorder." In some embodiments, methods of the present disclosure may include treating adenosine receptor-related indications by administering an effective amount of compounds and/or compositions disclosed herein (e.g., A2A and/or A1 receptor antagonist compounds) to a subject.

The present disclosure provides a method of treating or preventing central nervous system (CNS) or neurodegenerative diseases or disorders in a subject using the compounds of this disclosure as therapeutic agents, or pharmaceutical compositions including the compounds. In some embodiments, the CNS disease is referred to as a neurodegenerative disease or disorder of the CNS. CNS and neurodegenerative diseases, which are the object of prevention or therapy using the compounds and pharmaceutical compositions of this disclosure, are diseases that include, but are not limited to, Parkinson's disease, Alzheimer's disease, amyotrophic lateral sclerosis, multiple sclerosis, Huntington's disease, depression, schizophrenia, and epilepsy.

In some embodiments, method is a method of treating or preventing Parkinson's disease, and includes administering to a subject having, or at risk of Parkinson's disease an effective amount of a compound of this disclosure. In some cases, the compound is one having dual inhibition activity at both A2A receptor and A1 receptor. In some cases, the compound is one having inhibition activity at A2A receptor.

In another embodiments, provided herein are methods for treating a movement disorder (hyperkinetic movement disorders related abnormalities in muscle control) or tremor. Exemplary movement disorders or tremor include, but are not limited to, Parkinson's disease and parkinsonism (defined particularly by bradykinesia), dystonia, chorea and Huntington's disease, ataxia, tremor (e.g., essential tremor, Parkinsonian tremor, orthostatic tremor, physiological tremor, psychogenic tremor), myoclonus and startle, tics and Tourette syndrome, Restless legs syndrome, stiff person syndrome, dyskinesia, and gait disorders.

In some embodiments, the method further comprises identifying a subject suffering from, or at risk of, a CNS or neurodegenerative disease.

In some embodiments, the method further comprises identifying an underlying disease or condition associated with the CNS or neurodegenerative disease.

The amount of the aforementioned pharmaceutical composition administered is the effective amount to treat or prevent illness for an entity or patient, and could be administered orally or non-orally according to the purpose. When administered orally, the amount administered based on the active component is 0.01 to 1,000 mg per 1 kg of body weight, more specifically 0.1 to 300 mg per 1 kg. When administered non-orally, 0.01 to 100 mg based on the active component is administered per 1 kg of body weight per day, and more specifically 0.1 to 50 mg is administered once or several times. The amount administered for a specific entity or patient can be determined based on many related factors including the patient's weight, age, sex, health status, diet, time of administration, method of administration, severity of the illness, and so on, must be understood to be able to be increased or decreased appropriately by the specialist, and the aforementioned amount of administration does not limit the scope of the present disclosure in any way. A medical doctor or veterinarian with ordinary level of knowledge in the related technological field may determine and prescribe effective amount of the pharmaceutical composition. For example, a medical doctor or veterinarian may start with the amount of the compound under the present disclosure used in a pharmaceutical composition that is lower than the amount required to achieve the desired treatment effect, and may increase the amount administered gradually until the desired effect is achieved.

Examples of suitable routes of administration include oral, rectal, transmucosal (including sublingual and buccal), intranasal, topical, transdermal or intestinal administration; parenteral delivery, including intramuscular, subcutaneous, intravenous, intramedullary injections, as well as intrathecal, direct intracerebroventricular injection, direct injections to the human brain, direct intraventricular, intraperitoneal, intranasal, or intraocular injections. The compounds can also be administered in sustained or controlled release dosage forms, including nanoparticles, depot injections, osmotic pumps, electronic pumps, pills, transdermal (including electrotransport) patches, and the like, for prolonged and/or timed, pulsed administration at a predetermined rate. Sustained or controlled release dosage forms may be used to increase CNS exposure and minimize systemic exposure. It is also possible to combine at least two different routes of administration.

The compounds and compositions of this disclosure may be administered alone, in combination with a compound according to another example of the present disclosure, or in simultaneous, separate or sequential concomitant administration with at least one other therapeutic agent, for example with other pharmaceutical active ingredients described herein.

In a specific example, a pharmaceutical composition of this disclosure includes within its scope at least one of the compounds in accordance with a specific example of the effective treatment amount as effective component, or a pharmaceutical composition that is contained in combination with a pharmaceutical carrier. Arbitrarily, the compound in accordance with an embodiment of the present disclosure could be administered independently, in combination with a compound in accordance with another specific example, or simultaneously with one or more other treatment medications, for example simultaneously with an anticancer medicine (e.g., as described herein) or with an active pharmaceutical material, separately, or consecutively in conjunction.

Definitions

Unless defined otherwise, all technical and scientific terms used herein have the same meaning as commonly understood by one of ordinary skill in the art to which this disclosure pertains.

It is understood that the definitions provided herein are not intended to be mutually exclusive. Accordingly, some chemical moieties may fall within the definition of more than one term.

Singular articles such as "a," "an" and "the" and similar referents in the context of describing the elements are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (i.e., "such as") provided herein, is intended merely to better illuminate the embodiments and does not pose a limitation on the scope of the claims unless otherwise stated.

In some embodiments, where the use of the term "about" is before a quantitative value, the present disclosure also includes the specific quantitative value itself, unless specifically stated otherwise. As used herein, the term "about" refers to a ±10% variation from the nominal value unless otherwise indicated or inferred. Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

The terms "pharmaceutically acceptable excipient," "pharmaceutically acceptable diluent," "pharmaceutically acceptable carrier," and "pharmaceutically acceptable adjuvant" are used interchangeably and refer to an excipient, diluent, carrier, or adjuvant that is useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. The phrase "pharmaceutically acceptable excipient" includes both one and more than one such excipient, diluent, carrier, and/or adjuvant.

The term "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (i.e., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal, intranasal, intramuscular, subcutaneous, and the like.

The terms "disease," "disorder," and "condition" are used interchangeably herein.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition. "Treatment" or "treating" includes: (i) prevention of the disease, disorder, or condition, i.e., reducing the incidence of and/or ameliorating the effect and/or duration of a disease, disorder, or condition from occurring in subjects that may get, be exposed to and/or be predisposed to the disease, disorder or condition, but may not yet have been diagnosed as having it; or are diagnosed as having the disease, disease, or condition; or are at risk of developing such disease, disorder, or condition; (ii) inhibition of the disease, disorder, or condition, i.e., preventing or delaying the onset of a disease, disorder, or condition; arresting further development or progression of a disease, disorder, or condition in a subject already suffering from or having one or more symptoms of the disease, disorder, or condition; or reducing the risk of a disease, disorder, or condition worsening; (iii) amelioration of the disease, disorder, or condition, i.e., attenuating, relieving, reversing or eliminating the disease, disorder, or condition, or one or more of symptoms thereof.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

Exemplary Embodiments

As described herein, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Notwithstanding the appended claims, aspects of the present disclosure are illustrated by the following clauses.

Clause 1. A method of treating a subject with a CNS disorder or neurodegenerative disorder, comprising administering an effective amount of a compound of formula (Ia)

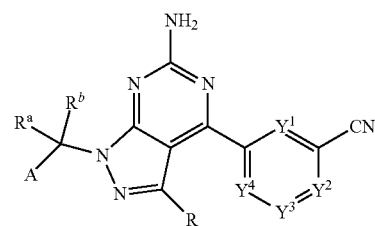

wherein:
R is H, $(C_1-C_3)$alkyl, or substituted $(C_1-C_3)$alkyl;
$Y^1$ to $Y^4$ are independently selected from $CR^{10}$ and N, wherein at least two of $Y^1$ to $Y^4$ are independently $CR^{10}$;
each $R^{10}$ is independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —CONH$_2$, substituted amido, —NH$_2$, substituted amino, —CO$_2$H, cyano, halogen, hydroxyl, —NO$_2$, —SO$_3$H, —SO$_2$NH$_2$, substituted sulfonamide, and thiol;
$R^a$ and $R^b$ are each independently selected from H, F, $(C_1-C_3)$alkyl, and substituted $(C_1-C_3)$alkyl, or $R^a$ and $R^b$ are cyclically linked and together with the carbon atom to which they are attached form a cyclopropyl or substituted cyclopropyl; and
A is phenyl, substituted phenyl, pyridyl or substituted pyridyl;
or a solvate, a hydrate, a prodrug, and/or a stereoisomer thereof, or a pharmaceutically acceptable salt thereof, to the subject.

Clause 2. The method of clause 1, wherein A is phenyl or phenyl substituted with one, two or three $R^{20}$ groups, each $R^{20}$ is independently selected from $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —CONH$_2$, substituted amido, —NH$_2$, substituted amino, —CO$_2$H, cyano, halogen, hydroxyl, —NO$_2$, —SO$_3$H, —SO$_2$NH$_2$, substituted sulfonamide, and thiol.

Clause 3. The method of clause 1, wherein R is H.

Clause 4. The method of clause 1, wherein Ra and Rb are each H.

Clause 5. The method of clause 2, wherein the compound is of formula (II):

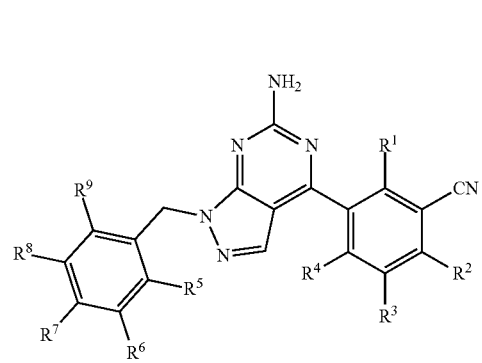

$R^1$ to $R^9$ are independently selected from H, $(C_1-C_8)$alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$ alkynyl, (C₁-C₃)haloalkyl, (C₁-C₈)alkoxy, substituted (C₁-C₈)alkoxy, —CONH₂, substituted amido, —NH₂, substituted amino, —CO₂H, cyano, halogen, hydroxyl, —NO₂, —SO₃H, —SO₂NH₂, substituted sulfonamide, and thiol.

Clause 6. The method of clause 5, wherein $R^1$ to $R^9$ are independently selected from H, (C₁-C₅)alkyl, substituted (C₁-C₅)alkyl, (C₁-C₃)haloalkyl, (C₁-C₅)alkoxy, substituted (C₁-C₅)alkoxy, —NH₂, substituted amino, halogen, and hydroxyl.

Clause 7. The method of clause 6, wherein $R^1$ to $R^9$ are independently selected from H, NH₂, F, CH₃, and CF₃.

Clause 8. The method of clause 5, wherein the compound is of formula (III):

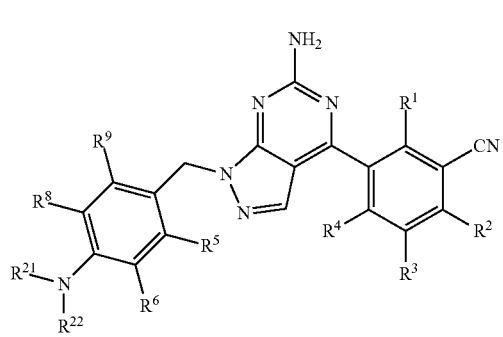

(III)

wherein:

$R^{21}$ and $R^{22}$ are independently selected from H, (C₁-C₈) alkyl, substituted (C₁-C₈)alkyl, SO₂R³⁰, and COR³⁰, wherein $R^{311}$ is (C₁-C₈)alkyl, or substituted (C₁-C₈) alkyl.

Clause 9. The method of clause 8, wherein $R^{21}$ and $R^{22}$ are each H;

$R^5$, $R^6$, $R^8$ and $R^9$ are independently selected from H, (C₁-C₅)alkyl, substituted (C₁-C₅)alkyl, (C₁-C₃)haloalkyl, (C₁-C₅)alkoxy, substituted (C₁-C₅)alkoxy, halogen, and hydroxyl.

$R^2$ to $R^4$ are each H; and $R^1$ is selected from H, (C₁-C₅)alkyl, substituted (C₁-C₅) alkyl, (C₁-C₃)haloalkyl, (C₁-C₅)alkoxy, substituted (C₁-C₅)alkoxy, halogen, and hydroxyl.

Clause 10. The method of clause 9, wherein $R^1$ is selected from H, F, CH₃, and CF₃.

Clause 11. The method of clause 1, wherein the compound of formula (Ia) is selected from:

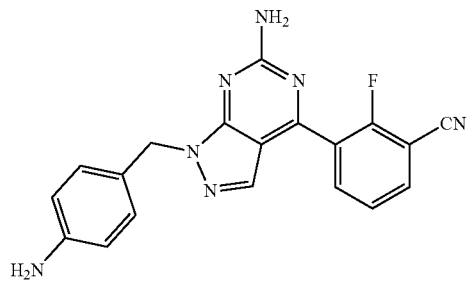

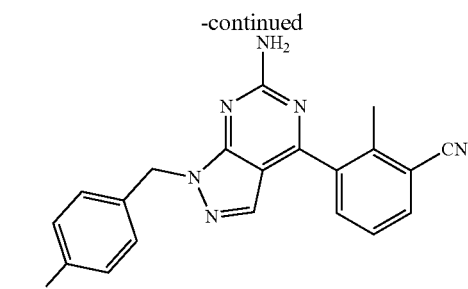

-continued

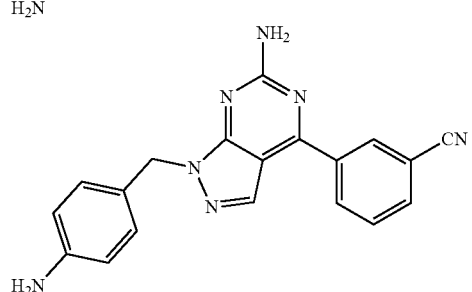

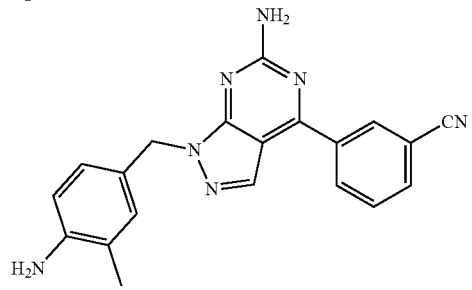

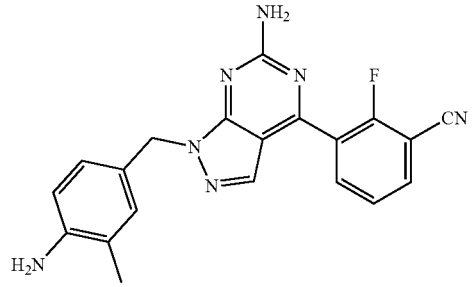

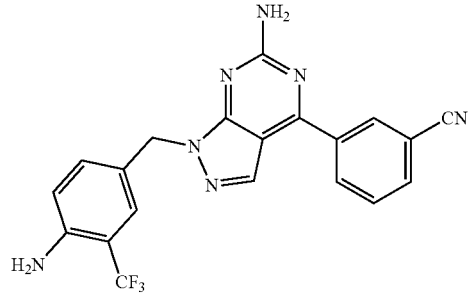

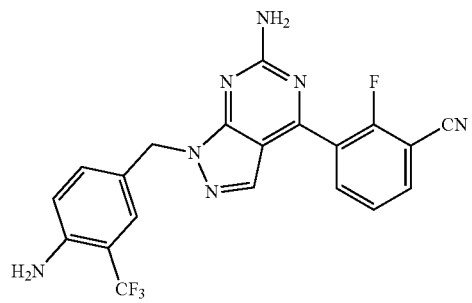

-continued
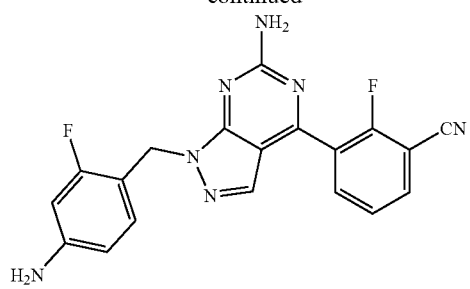
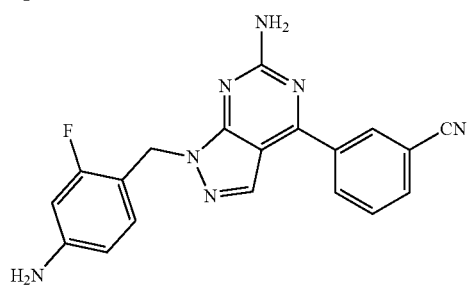
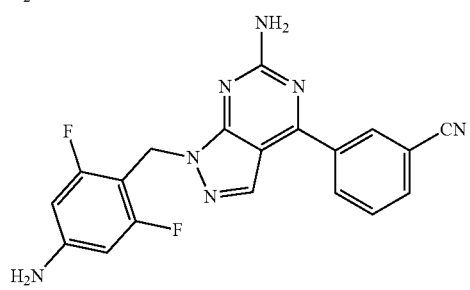
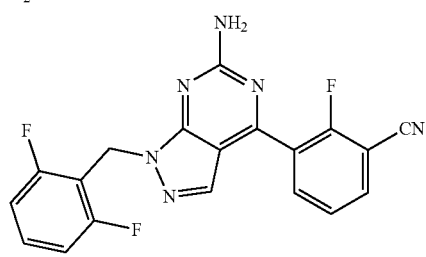
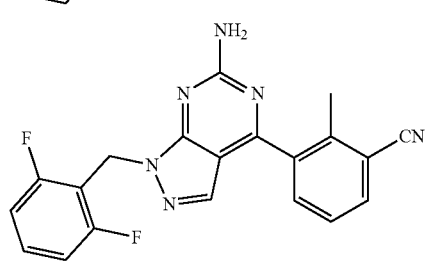
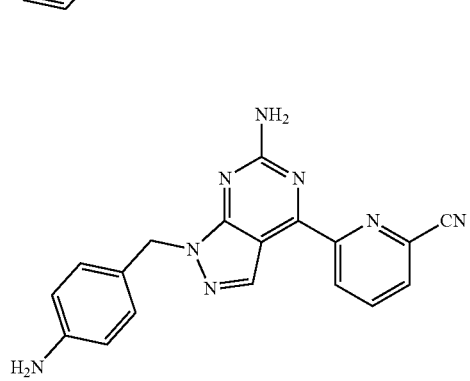
-continued
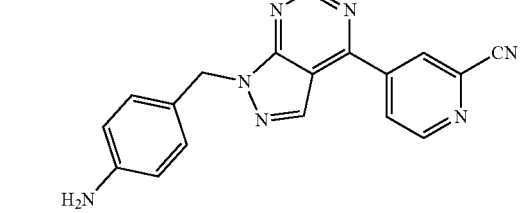
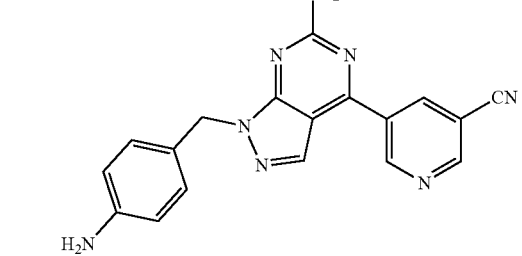
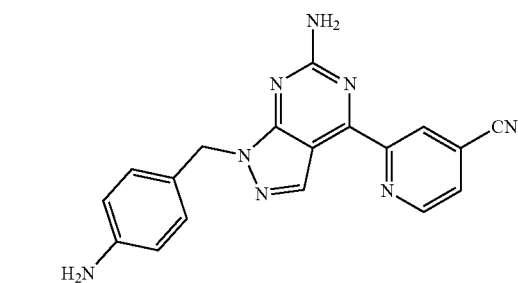
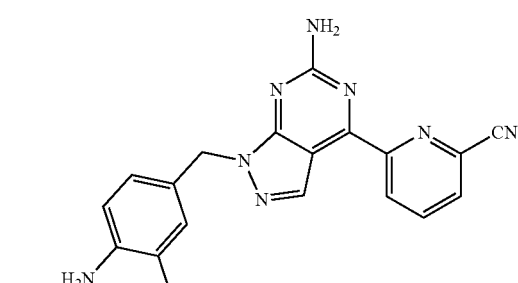
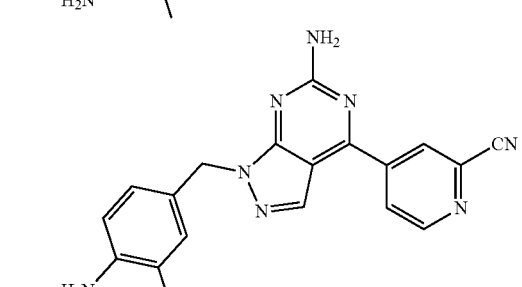
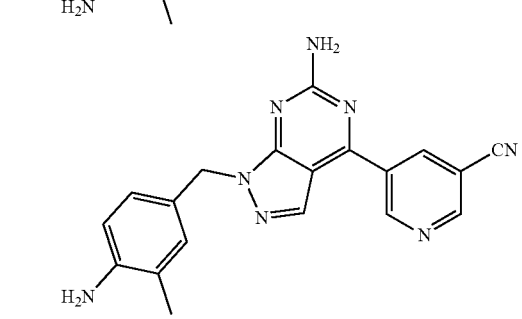

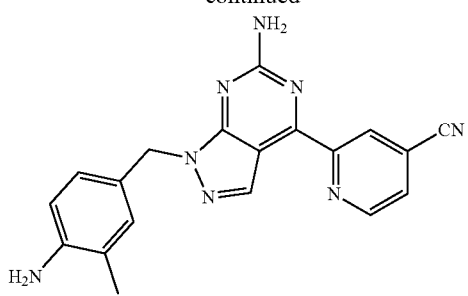
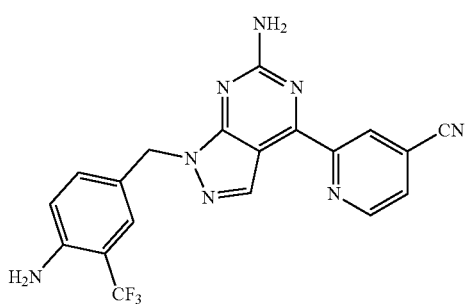
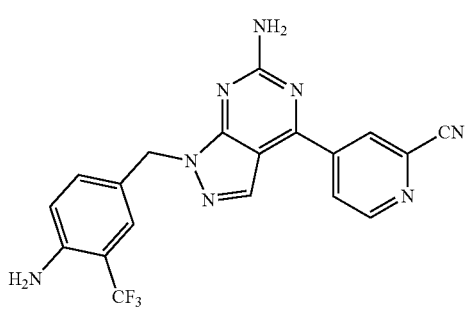
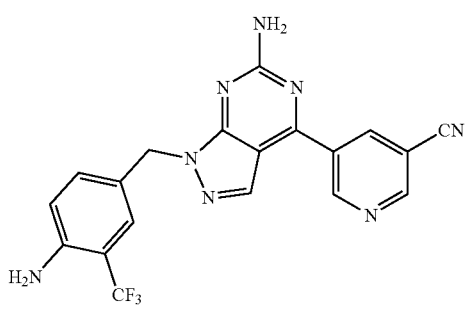
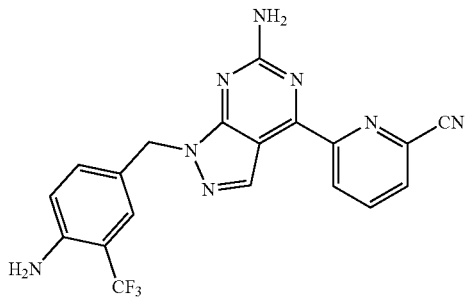
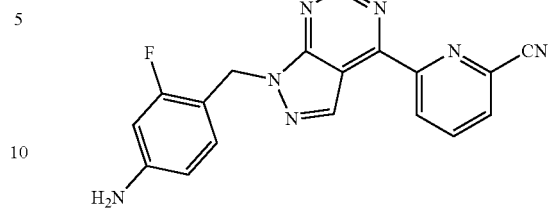
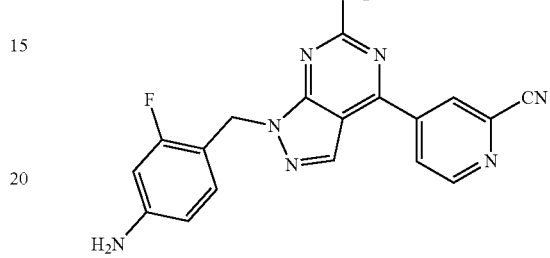
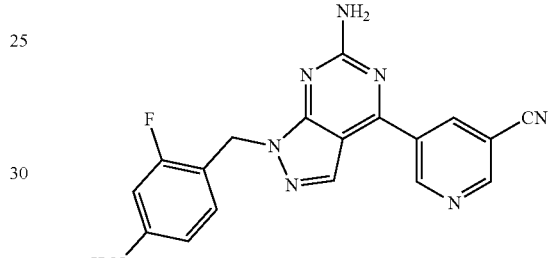
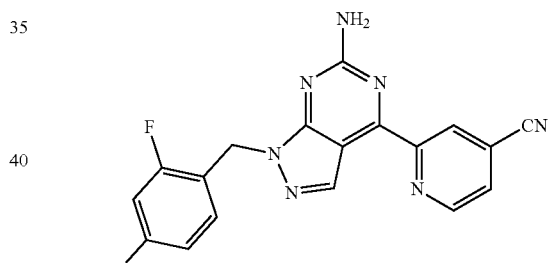
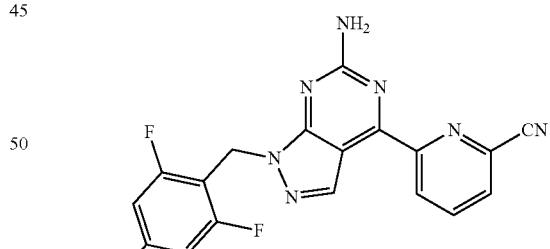
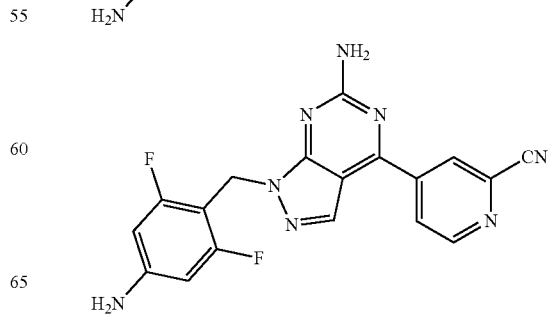

-continued

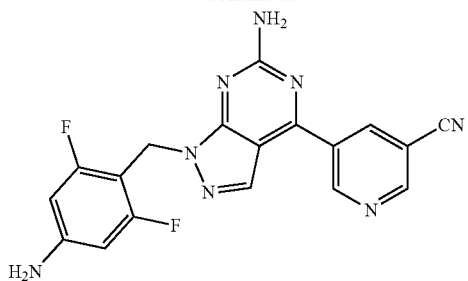

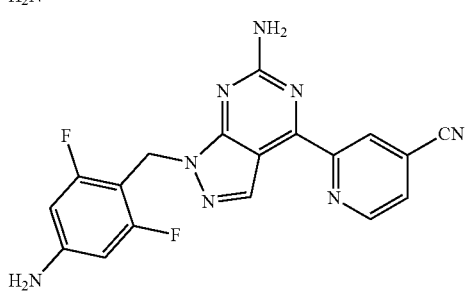

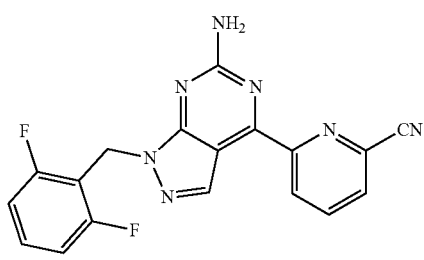

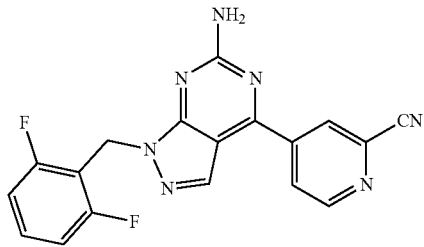

-continued

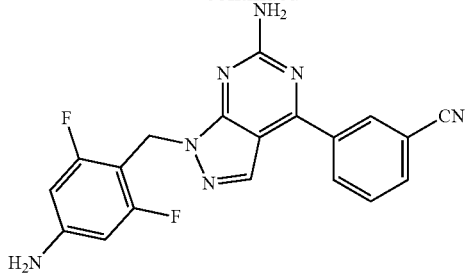

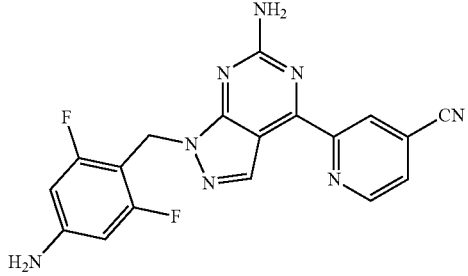

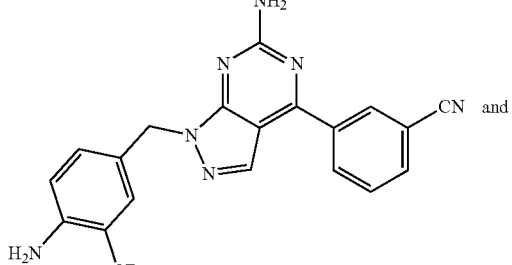

and

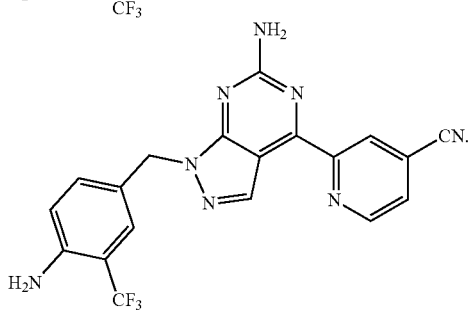

Clause 12. The method of clause 1, wherein the CNS disorder is selected from the group consisting of Huntington's disease, Parkinson's disease, Alzheimer's disease, schizophrenia, mild-cognitive impairment, attention deficit hyperactivity disorder (ADHD), multiple sclerosis, vascular dementia, and amyotrophic lateral sclerosis.

Clause 13. The method of clause 1, wherein the CNS disorder is associated with an adenosine receptor.

Clause 14. The method of clause 13, wherein the adenosine receptor is adenosine A2A and/or A1 receptor.

Clause 15. The method of clause 1, wherein the CNS disorder is Parkinson's disease.

Clause 16. A method of treating an injury or disease that results in neuronal degeneration selected from the group consisting of closed head injuries, blunt trauma, penetrating trauma, hemorrhagic stroke, ischemic stroke, glaucoma, cerebral ischemia, ageing, and neuronal damage caused by surgical procedures, comprising administering a therapeutically effective amount of a compound of the formula (Ia) described herein to the subject in need thereof, wherein the injury is a primary nervous system injury selected from the group comprising closed head injuries, blunt trauma, penetrating trauma, hemorrhagic stroke, ischemic stroke, glaucoma, cerebral ischemia, spinal cord injury, ageing, and neuronal damage caused by surgical procedures.

Clause 17. The method of clause 16, wherein the disease that results in neuronal degeneration is Parkinson's disease.

Clause 18. A method of treating a movement disorder in a subject, comprising administering to a subject in need thereof a therapeutically effective amount of a compound of the formula (Ia) described herein to the subject.

Clause 19. The method of clause 18, wherein the subject suffers from an adenosine receptor associated disorder, wherein the adenosine receptor associated disorder is Parkinson's disease).

Clause 20. The method of clause 18, wherein the movement disorders is selected from the group consisting of bradykinesia, dystonia, chorea and Huntington's disease, ataxia, tremor, myoclonus and startle, tics and Tourette syndrome, Restless legs syndrome, stiff person syndrome, dyskinesia, and gait disorders.

EXAMPLES

The following examples are offered to illustrate the present disclosure and are not to be construed in any way as limiting the scope of the present technology. Any methods that are functionally equivalent are within the scope of the present technology. Various modifications of the present technology in addition to those described herein will become apparent to those skilled in the art from the foregoing description. Such modifications fall within the scope of the appended claims.

Unless otherwise stated, all temperatures are in degrees Celsius. Efforts have been made to ensure accuracy with respect to numbers used (e.g., amounts, temperatures, etc.), but some experimental errors and deviation should be allowed for.

If an abbreviation is not defined, it has its generally accepted meaning.

General Synthetic Methods

Final compounds were confirmed by high-performance liquid chromatography/mass spectrometry (HPLC/MS) analysis and determined to be >90% pure by weight. $^1$H nuclear magnetic resonance (NMR) spectra were recorded in CDCl3 (residual internal standard CHCl$_3$=δ 7.26), dimethyl sulfoxide (DMSO)-d$_6$ (residual internal standard CD$_3$SOCD$_2$H=δ 2.50), methanol-d$_4$ (residual internal standard CD$_2$HOD=δ 3.30), or acetone-d$_6$ (residual internal standard CD$_3$COCD$_2$H=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

Example 1: Preparation of Compounds

The compounds of this disclosure are produced by adapting well known chemical conversions in accordance with the method illustrated by Scheme 1 or 2 below. The synthesis of several exemplary compounds of Table 1 is described below in examples 1.1 to 1.33. Several other compounds of Table 1 were prepared by adapting the methods described herein and assessed according to the biological assays described in Example 2.

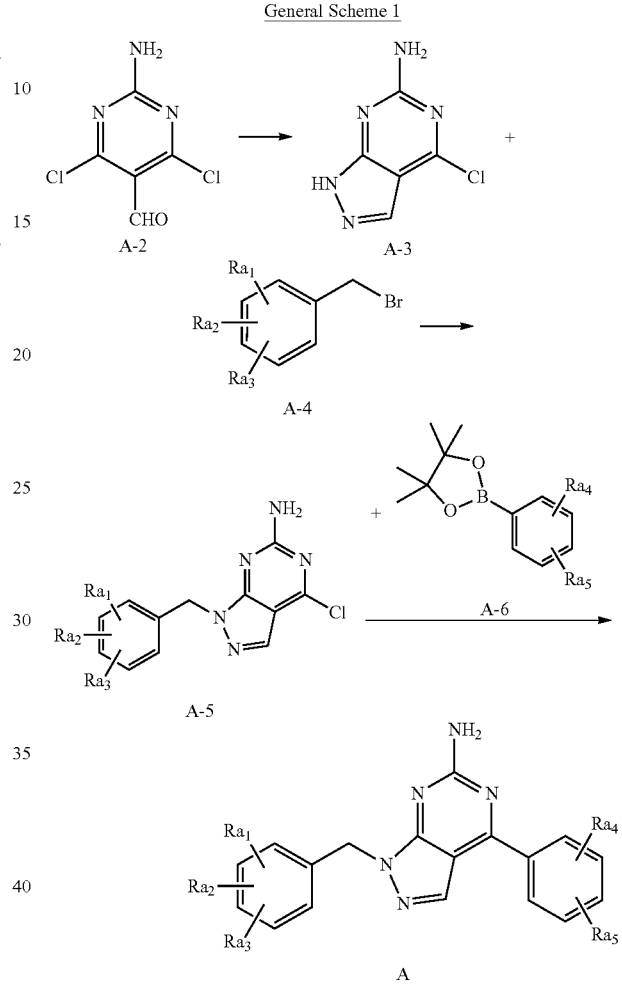

General Scheme 1

Exemplary synthetic methods for Scheme 1 are described in detail below.

To describe in more detail by referring to the aforementioned scheme 1, it is possible to produce the compound indicated by the aforementioned scheme 1 through a series of processes that includes the first stage in which the A-2 compound is dissolved in a solvent of tetrahydrofuran and H$_2$O, and in which the compound of scheme A-3 is produced by subjecting the solution to chain reaction with hydrazine monohydrate for 24 hours at 25° C. to 60° C., the second stage in which the A-3 compound is dissolved in the N,N-dimethylformamide solvent, and then subjecting the solution to nucleophilic substitution reaction with the compound of scheme A-4 for 24 hours at 25° C. to 60° C. under the condition in which potassium carbonate or cesium carbonate is provided to produce the scheme A-5 compound; and the third stage in which the A-5 compound is dissolved in 1,4-dioxane and distilled water, and in which the solution is subject to Suzuki coupling reaction with the compound of scheme A-6 for two hours to 24 hours at 100° C. to 115° C. to produce the A compound under the condition in which 3-(4,4,5,5-tetramethyl-1,3,2-dioxaborolane-2-yl) benzonitrile and its derivative, and tetrakis (triphenylphosphine) palladium and sodium carbonate are provided, or in which the solution is subject to the Suzuki coupling reaction under the same conditions and in which the solution is dissolved in ethanol solvent, and in which the solution is subject to reduction reaction under the conditions of tin (II) chloride dihydrate and acid. Here, the aforementioned scheme 1's $R_{a1}$, $R_{a2}$, $R_{a3}$, $R_{a4}$, and $R_{a5}$ correspond to the substituents of the formula described herein, e.g., formula (II)'s $R^1$ to $R^9$, and cyano group.

Example 1.1: Production of 3-(6-amino-1-(4-aminobenzyl)-1H-pyrazolo[3,4-d]pyrimidine-4-yl) benzonitrile (Compound 201)

1.1.1. Production of 4-chloro-(4-nitrobenzyl)-1H-pyrazolo[3,4-d]pyrimidine-6-amine

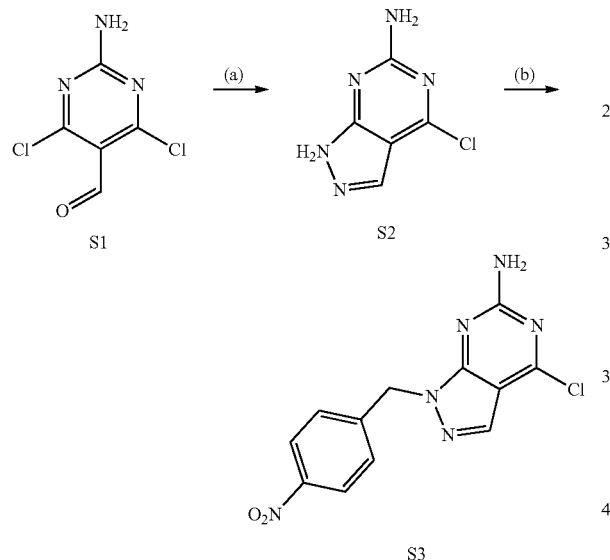

Reagents and Conditions: (a) hydrazine, TEA, THF:H$_2$O (3:1), r.t. to 50° C., 3 h, quant; (b) 4-nitrobenzyl bromide, K$_2$CO$_3$, DMF, 0° C. to r.t., 12 h, 58%.

Stage 1: Production of 4-chloro-1H-pyrazolo[3,4-d]pyrimidine-6-amine 2-amino-4,6-dichloropyrimidine-5-carbaldehyde (51, 4 g, 20.83 mmol) was melted in a solvent of tetrahydrofuran (THF) and H$_2$O, and to this hydrazine monohydrate (0.78 ml, 24.99 mmol) and triethylamine (TEA, 3.51 ml, 24.99 mmol) were added. Afterwards, the aforementioned reaction mixture was heated at 50° C. and agitated for 3 hours, and concentrated. Then, the aforementioned concentrate was cleaned and distilled with distilled water to obtain an intermediate compound (S2, 3.45 g, 100%). $^1$H-NMR (DMSO-d$_6$, 400 MHz): δ 13.25 (s, 1H), 8.02 (s, 1H), 7.14 (s, 2H).

Stage 2: Production of 4-chloro-1-(4-nitrobenzyl)-1H-pyrazolo[3,4-d]pyrimidine-6-amine The intermediate compound produced in the aforementioned stage 1 (S2, 3.0 g, 18.12 mmol) was dissolved in dimethylformamide (DMF), and 4-nitro benzyl bromide (3.92 g, 18.12 mmol) and potassium carbonate (K$_2$CO$_3$, 3.75 g, 27.18 mmol) was added to this. Then, this was agitated in room temperature for 12 hours. The aforementioned reaction mixture was diluted with ethyl acetate (EA), and was cleaned with distilled. Then, it was dried with magnesium sulfate and then filtered and concentrated. Then, the aforementioned concentrate was refined with silica gen chromatography to obtain the desired compound (S3, 3.2 g, 58%). $^1$H-NMR (DMSO-d$_6$, 400 MHz): δ 8.19 (d, 2H), 8.09 (s, 1H), 7.40-7.38 (m, 4H), 5.56 (s, 2H).

1.1.2. Production of 3-(6-amino-1-(4-aminobenzyl)-1H-pyrazolo[3,4-d]pyrimidine-4-yl) benzonitrile (Compound 201)

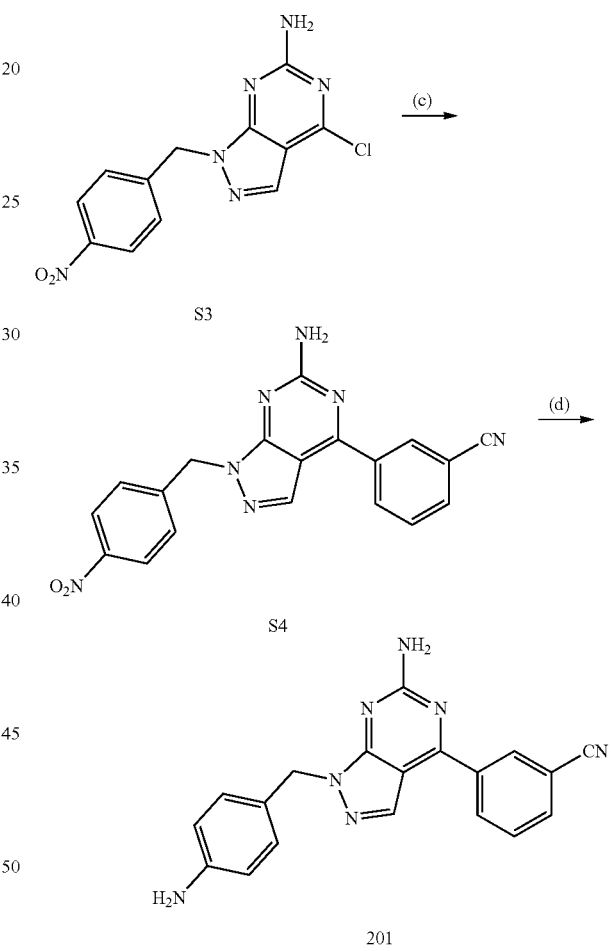

Reagents and Conditions: (c) 3-(4,4,5,5-tetramethyl-1,3,2-dioxaborolan-2-yl)benzonitrile, Pd(PPh$_3$)$_4$, Na$_2$CO$_3$, dioxane:H$_2$O (8:1), r.t. to 105° C., 12 h, 70%; (d) SnCl$_2$.2H$_2$O, conc. HCl, EtOH, r.t. to 50° C., 3 h, 45%.

Stage 1: Production of 3-(6-amino-1-(4-nitrobenzyl)-1H-pyrazolo[3,4-d]pyrimidine-4-yl) benzonitrile The compound of the aforementioned example 1-1 (S3, 1.0 g, 3.28 mmol) was dissolved in the solvent of 1,4-dioxane and H$_2$O, and 3-(4,4,5,5-tetramethyl-1,3,2-dioxaborolan-2-yl) benzonitrile (1.12 g, 4.92 mmol), tetrakis (triphenylphosphine) palladium ((0) (Pd(PPh$_3$)$_4$, 758 mg, 0.65 mmol), and sodium carbonate (Na$_2$CO$_3$, 695 mg, 6.56 mmol) were added to this. Afterwards, the aforementioned reaction mixture was agitated for 12 hours at the 105° C. using a sealed tube, and then was diluted with dichloromethane (DCM), and then this was cleaned with distilled water. Afterwards, this was dried with magnesium sulfate and then filtered and concentrated, and the aforementioned concentrate was cleaned with ethyl acetate/hexane (EA/Hex) to obtain an intermediate compound (S4, 852 mg, 70%). $^1$H-NMR (DMSO-d$_6$, 400 MHz): δ 8.54 (s, 1H), 8.51-8.49 (m, 2H), 8.08 (dd, 1H), 7.80 (t, 1H), 7.42 (d, 2H), 7.15 (s, 2H), 5.62 (s, 2H).

Stage 2: Production of 3-(6-amino-1-(4-aminobenzyl)-1H-pyrazolo[3,4-d]pyrimidine-4-yl) benzonitrile The intermediate compound produced in the aforementioned stage 1 (S4, 400 mg, 1.07 mmol) was dissolved in ethanol (EtOH), and then tin (II) chloride dihydrate (SnCl$_2$ 2H$_2$O, 730 mg, 3.23 mmol) and Conc. HCl (aq) (1.8 ml, 21.54 mmol) were added to this. Afterwards, the aforementioned reaction mixture was agitated for 3 hours at 50° C., and then was diluted with dichloromethane (DCM), and was cleaned with distilled water. Afterwards, this was dried with magnesium sulfate, and then dried, filtered, and concentrated. Then, the aforementioned concentrate was refined with silica gen chromatography to obtain the desired compound (201, 161 mg, 45%). $^1$H-NMR (DMSO-d$_6$, 400 MHz): δ 8.50 (s, 1H), 8.48-8.45 (m, 1H), 8.35 (s, 1H), 8.07-8.04 (m, 1H), 7.79 (t, 1H), 7.07 (s, 2H), 6.95 (d, 2H), 6.47 (d, 2H), 5.23 (s, 2H), 5.04 (s, 2H).

Example 1.2: Production of 3-(6-amino-1-(4-aminobenzyl)-1H-pyrazolo[3,4-d]pyrimidine-4-yl)-2-methylbenzonitrile (Compound 205)

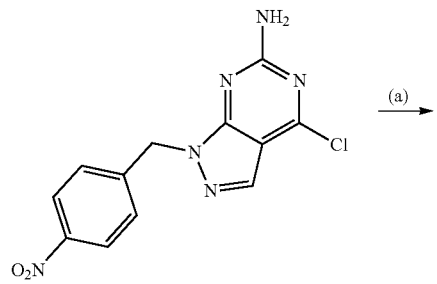

S3

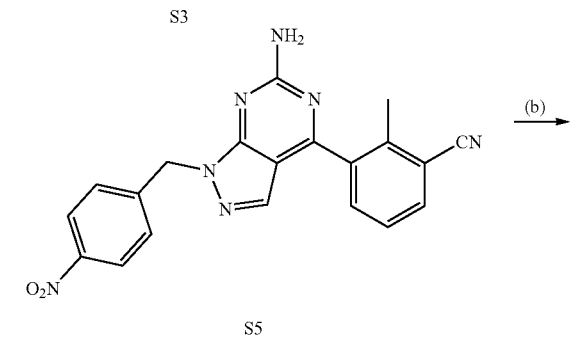

S5

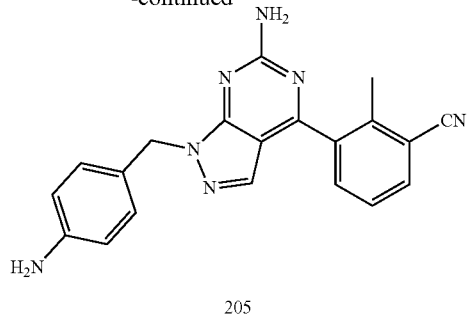

205

Reagents and Conditions: (a) 2-methyl-3-(4,4,5,5-tetramethyl-1,3,2-dioxaborolan-2-yl)benzonitrile, Pd(PPh$_3$)$_4$, Na$_2$CO$_3$, dioxane:H$_2$O (8:1), r.t. to 105° C., 12 h, 81%; (b) SnCl$_2$.2H$_2$O, conc HCl, EtOH, r.t. to 50° C., 3 h, 74%.

Stage 1: Production of 3-(6-amino-1-(4-nitrobenzyl)-1H-pyrazolo[3,4-d]pyrimidine-4-yl)-2-methylbenzonitrile In stage 1 of the aforementioned example 1.1.2, except for using 2-methyl-3-(4,4,5,5-tetramethyl-1,3,2-dioxiborolan-2-yl) benzonitrile (120 mg, 0.49 mmol) instead of 3-(4,4,5,5-tetramethyl-1,3,2-dioxaborolane-2-yl) benzonitrile (1.12 g, 4.92 mmol), the same process as stage 1 of the aforementioned example 1.1.2 was carried out to obtain an intermediate compound (S5, 103 mg, 81%). $^1$H-NMR (DMSO-d$_6$, 400 MHz): δ 8.21 (d, 2H), 7.97 (d, 1H), 7.90 (s, 1H), 7.82 (d, 1H), 7.56 (t, 1H), 7.46 (d, 2H), 7.13 (s, 2H), 5.59 (s, 2H), 2.52 (s, 3H)

Stage 2: Production of 3-(6-amino-1-(4-aminobenzyl)-1H-pyrazolo[3,4-d]pyrimidine-4-yl)-2-methylbenzonitrile In stage 2 of the aforementioned example 1.1.2, except for changing the amount of tin (II) chloride dihydrate (SnCl$_2$ 2H$_2$O, 180 mg, 0.80 mmol), and Conc. HCl (aq) (0.45 ml, 5.34 mmol), the same process as stage 2 of the aforementioned example 1.1.2 was performed on the intermediate compound of the aforementioned stage 1 (S5,103 mg, 0.26 mmol), to obtain a desired compound (205.71 mg, 74%). $^1$H-NMR (DMSO-d$_6$, 400 MHz): δ 7.95 (d, 1H), 7.79 (d, 1H), 7.77 (s, 1H), 7.54 (t, 1H), 7.05 (s, 2H), 6.98 (d, 2H), 6.48 (d, 2H), 5.21 (s, 2H), 5.04 (s, 2H), 2.49 (s, 3H).

Example 1.3: Production of 3-(6-amino-1-(4-aminobenzyl)-1H-pyrazolo[3,4-d]pyrimidine-4-yl)-2-fluorobenzonitrile (Compound 202)

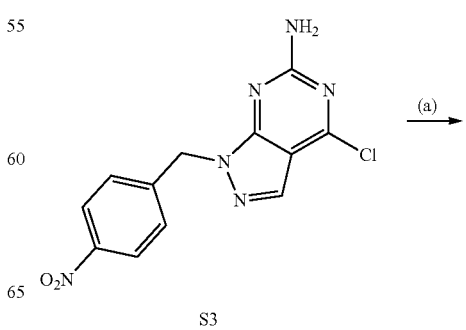

S3

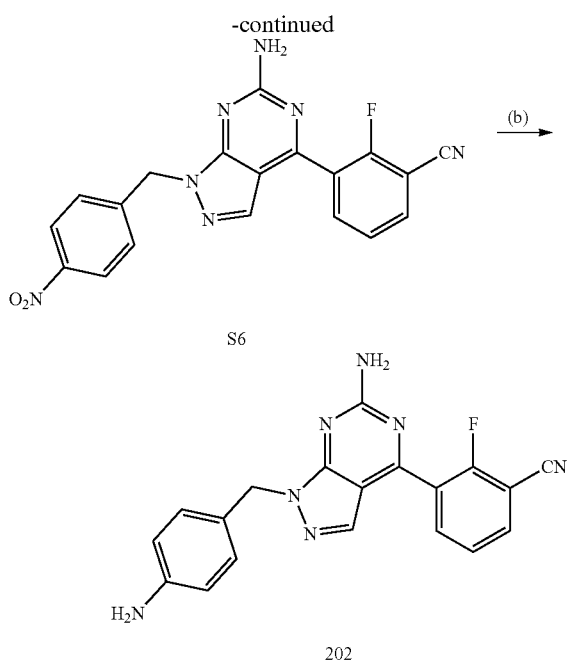

S6

202

Reagents and Conditions: (a) 2-fluoro-3-(4,4,5,5-tetramethyl-1,3,2-dioxaborolan-2-yl)benzonitrile, Pd(PPh₃)₄, Na₂CO₃, dioxane:H₂O (8:1), r.t. to 105° C., 12 h, 90%; (b) SnCl₂.2H₂O, conc. HCl, EtOH, r.t. to 50° C., 3 h, 92%.

Stage 1: Production of 3-(6-amino-1-(4-nitrobenzyl)-1H-pyrazolo[3,4-d]pyrimidine-4-yl)-2-fluorobenzonitrile The same process as stage 1 of the aforementioned example 1.1.2 was performed except that 2-fluoro-3-(4,4,5,5-tetramethyl-1,3,2-dioxaborolan-2-yl) benzonitrile (1.21 g, 4.92 mmol) was used instead of 3-(4,4,5,5-tetramethyl-1,3,2-dioxaborolan-2-yl) benzonitrile (1.12 g, 4.92 mmol) in stage 1 of the aforementioned example 1.1.2, and except that the amount of tetrakis (triphenylphosphine) palladium (0) (Pd(PPh₃)₄, 758 mg, 0.65 mmol), and the amount of sodium carbonate (Na₂CO₃, 695 mg, 6.56 mmol) were changed, to obtain an intermediate compound (S6, 1.15 g, 90%). ¹H-NMR (DMSO-d₆, 400 MHz): δ 8.22-8.15 (m, 4H), 8.10 (d, 1H), 7.61 (t, 1H), 7.43 (d, 2H), 7.21 (s, 2H), 5.60 (s, 2H).

Stage 2: Production of 3-(6-amino-1-4(4-aminobenzyl)-1H-pyrazolo[3,4-d]pyrimidine-4-yl)-2-fluorobenzonitrile The same process as stage 2 of the aforementioned example 1.1.2 was performed for the intermediate compound of the aforementioned stage 1 (S6, 144 mg, 0.37 mmol) except that the amount of tin (II) chloride dihydrate (SnCl₂ 2H₂O, 250 mg, 1.11 mol), Conc. HCl (aq) (0.62 ml, 7.40 mmol) in stage 2 of the aforementioned example 1.1.2 was changed to obtain the desired compound (202, 131 mg, 92%). ¹H-NMR (DMSO-d₆, 400 MHz): δ 8.14 (t, 2H) 7.96 (d, 1H), 7.11 (s, 2H), 6.96 (d, 2H), 6.48 (d, 2H), 5.22 (s, 2H), 5.04 (s, 2H).

Example 1.4: Production 3-(6-amino-1-(4-amino-3-methylbenzyl)-1H-pyrazolo[3,4-d]pyrimidine-4-yl)benzonitrile (Compound 204)

1.4.1. Production of 3-(6-amino-1H-pyrazolo[3,4-d]pyrimidine-4-yl)benzonitrile (Intermediate Compound S7)

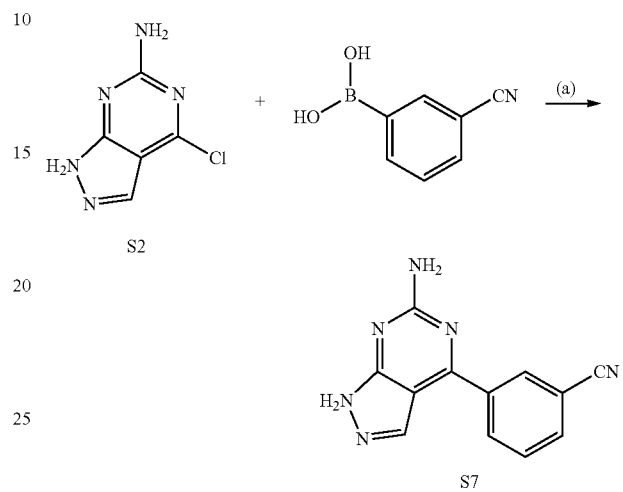

S2

S7

Reagents and Conditions: (a) Pd(PPh₃)₄, Na₂CO₃, dioxane/H₂O, 100° C., 16 h.

A mixture of 4-chloro-1H-pyrazolo[3,4-d]pyrimidine-6-amine (500 mg, 1 eq), (3-cyanophenyl)boronic acid (519 mg, 1.2 eq), Pd(PPh₃)₄ (340 mg, 0.1 eq) and Na₂CO₃ (625 mg, 2 eq) in dioxane (20 mL) was degassed and purged with nitrogen for three times, and then the mixture was stirred at 100° C. for 16 hr under nitrogen atmosphere. The reaction mixture was partitioned between ethyl acetate (100 mL) and water (30 mL). The organic phase was separated, washed by brine (20 mL), dried over sodium sulfate, filtered and concentrated under reduced pressure to give a residue. The crude product 3-(6-amino-1H-pyrazolo[3,4-d]pyrimidine-4-yl)benzonitrile (500 mg, crude) was obtained as a yellow solid and used into the next step without further purification. MS: m/z=237.1 (M+1, ESI+).

1.4.2. Production of 3-(6-amino-1-(4-amino-3-methylbenzyl)-1H-pyrazolo[3,4-d]pyrimidine-4-yl)benzonitrile (Compound 204)

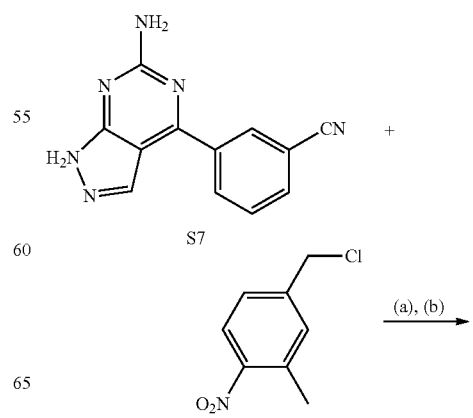

S7

-continued

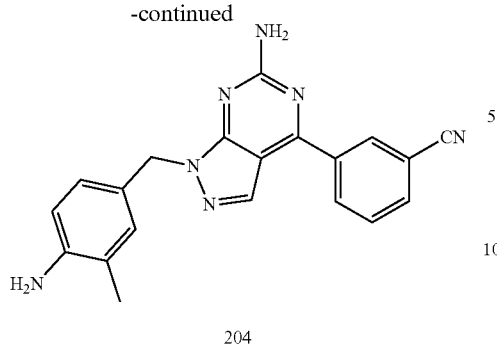

204

Reagents and Conditions: (a) K₂CO₃, DMF, 80° C., 16h; (b) Fe, NH₄Cl, EtOH/H₂O, 60° C., 1 h.

Stage 1: Production of 3-[6-amino-1-[(3-methyl-4-nitro-phenyl)methyl]pyrazolo[3,4-d]pyrimidine-4-yl]benzonitrile To a solution of 4-(chloromethyl)-2-methyl-1-nitro-benzene (500 mg, 1.27 eq) and intermediate compound S7 or 3-(6-amino-1H-pyrazolo[3,4-d]pyrimidine-4-yl)benzonitrile (500 mg, 1 eq) in DMF (10 mL) was added K₂CO₃ (585 mg, 2 eq). The mixture was stirred at 80° C. for 16 hr. The reaction mixture was concentrated under reduced pressure to give a residue. The residue was purified by prep-HPLC (column: Phenomenex Luna C18 150*25 mm*10 μm; mobile phase: [water (0.225% FA)-ACN]; B %: 40%-70%, 10 min). Compound 3-[6-amino-1-[(3-methyl-4-nitro-phenyl)methyl]pyrazolo[3,4-d]pyrimidine-4-yl]benzonitrile (200 mg, 24% yield) was obtained as a yellow solid. ¹H NMR (400 MHz, DMSO-d₆) δ=8.56-8.42 (m, 3H), 8.10-8.06 (m, 1H), 8.00-7.92 (m, 1H), 7.86-7.76 (m, 1H), 7.40-7.30 (m, 1H), 7.24-7.08 (m, 3H), 5.65-5.43 (m, 2H), 2.49 (s, 3H). MS: m/z=386.0 (M+1, ESI+).

Stage 2: Production of 3-(6-amino-1-(4-amino-3-methylbenzyl)-1H-pyrazolo[3,4-d]pyrimidine-4-yl)benzonitrile (Compound 204)

To a solution of 3-[6-amino-1-[(3-methyl-4-nitro-phenyl)methyl]pyrazolo[3,4-d]pyrimidine-4-yl]benzonitrile (150 mg, 1 eq) in ethanol (12 mL) and water (4 mL) were added iron dust (108 mg, 1.95 mmol, 5 eq) and NH₄Cl (166 mg, 8 eq). The mixture was stirred at 60° C. for 1 hr. The reaction mixture was filtered and concentrated under reduced pressure to give a residue. The residue was purified by prep-HPLC (column: Phenomenex Luna C18 150*25 mm*10 μm; mobile phase: [water (0.225% FA)-ACN]; B %: 23%-53%, 10 min). Compound 204 or 3-[6-amino-1-[(4-amino-3-methyl-phenyl)methyl]pyrazolo[3,4-d]pyrimidine-4-yl]benzonitrile (54.26 mg, 38% yield, 98.27% purity) was obtained as a white solid. ¹H NMR (400 MHz, DMSO-d6) δ=8.54-8.49 (m, 1H), 8.49-8.45 (m, 1H), 8.37-8.31 (m, 1H), 8.09-8.01 (m, 1H), 7.84-7.70 (m, 1H), 7.16-6.99 (m, 2H), 6.91-6.86 (m, 1H), 6.86-6.80 (m, 1H), 6.58-6.45 (m, 1H), 5.33-5.14 (m, 2H), 4.98-4.57 (m, 2H), 2.02-1.96 (m, 3H).

Example 1.5: Production 3-(6-amino-1-(4-amino-3-methylbenzyl)-1H-pyrazolo[3,4-d]pyrimidine-4-yl)-2-fluorobenzonitrile (Compound 206)

1.5.1. Production of 4-chloro-1-(3-methyl-4-nitrobenzyl)-1H-pyrazolo[3,4-d]pyrimidine-6-amine (Intermediate Compound S8)

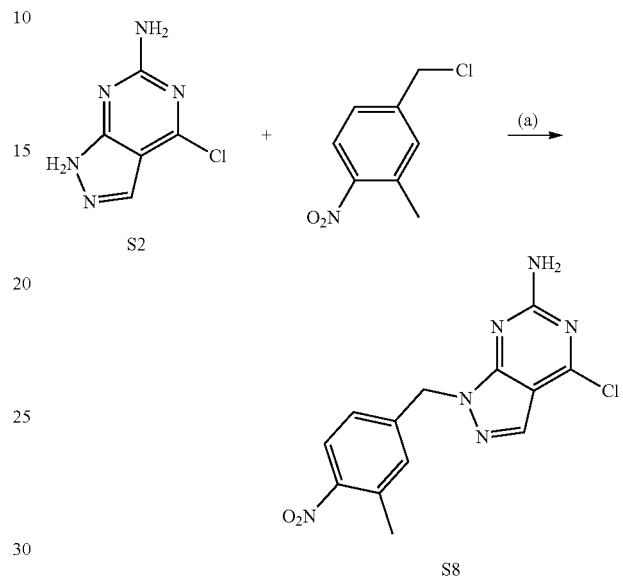

Reagents and Conditions: (a) K₂CO₃, DMAc, 80° C., 16 h.

To a solution of 4-chloro-1H-pyrazolo[3,4-d]pyrimidine-6-amine (0.8 g, 1 eq) and 4-(chloromethyl)-2-methyl-1-nitro-benzene (720 mg, 0.8) in DMAc (50 mL) was added K₂CO₃ (1.30 g, 2 eq). The mixture was stirred at 80° C. for 16 hr. The reaction mixture filtered and concentrated under reduced pressure to give a residue. The crude product 4-chloro-1-[(3-methyl-4-nitro-phenyl)methyl]pyrazolo[3,4-d]pyrimidine-6-amine (800 mg, crude) was obtained as a yellow solid and used into the next step without further purification. MS: m/z=354.9 (M+1, ESI+).

1.5.2. Production of 3-(6-amino-1-(4-amino-3-methylbenzyl)-1H-pyrazolo[3,4-d]pyrimidine-4-yl)-2-fluorobenzonitrile (Compound 206)

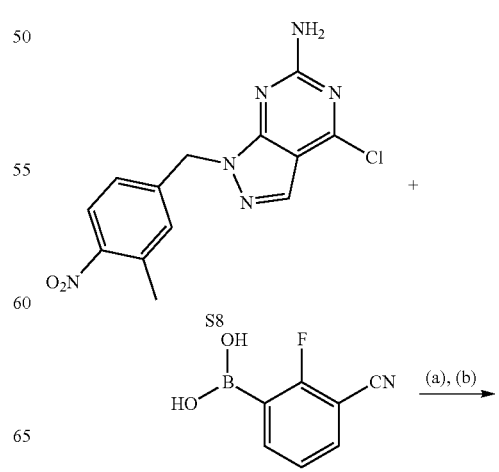

-continued

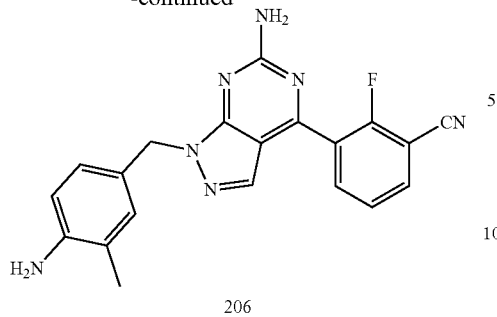

206

Reagents and condition: (a) Pd(PPh$_3$)$_4$, K$_2$CO$_3$, dioxane/H$_2$O, 100° C., 16 h; (b) Fe, NH$_4$Cl, EtOH/H$_2$O, 60° C., 1 h.

Stage 1: Production of 3-(6-amino-1-(3-methyl-4-nitrobenzyl)-1H-pyrazolo[3,4-d]pyrimidine-4-yl)-2-fluorobenzonitrile A mixture of (3-cyano-2-fluoro-phenyl)boronic acid (434 mg, 1.2 eq), intermediate compound S8 or 4-chloro-1-[(3-methyl-4-nitro-phenyl)methyl]pyrazolo[3,4-d]pyrimidine-6-amine (700 mg, 1 eq), Pd(PPh$_3$)$_4$ (253 mg, 219.63 μmol, 0.1 eq) and Na$_2$CO$_3$ (465 mg, 2 eq) in dioxane (10 mL) and water (2 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography CISCO®; 40 g SEPAFLASH® Silica Flash Column, Eluent of 0~80% Ethyl acetate/Petroleum ether gradient @ 40 mL/min). Compound 3-[6-amino-1-[(3-methyl-4-nitro-phenyl)methyl]pyrazolo[3,4-d]pyrimidine-4-yl]-2-fluoro-benzonitrile (800 mg, 90% yield) was obtained as a yellow solid. MS: m/z=386.0 (M+1, ESI+).

Stage 2: Production of 3-(6-amino-1-(4-amino-3-methylbenzyl)-1H-pyrazolo[3,4-d]pyrimidine-4-yl)-2-fluorobenzonitrile (Compound 206)

To a solution of 3-[6-amino-1-[(3-methyl-4-nitro-phenyl)methyl]pyrazolo[3,4-d]pyrimidine-4-yl]-2-fluoro-benzonitrile (200 mg, 1 eq) in water (4 mL) and ethanol (12 mL) were added iron dust (138 mg, 5 eq) and NH$_4$Cl (212 mg, 8 eq). The mixture was stirred at 60° C. for 1 hr. The reaction mixture was filtered and concentrated under reduced pressure to give a residue. The residue was purified by prep-HPLC (column: Phenomenex Synergi C18 150*25 mm*10 μm; mobile phase: [water (0.225% FA)-ACN]; B %: 16%-46%, 11 min), the 89% purity compound was obtained after first purification. The residue was purified by prep-HPLC (column: Phenomenex Luna C18 150*25 mm*10 μm; mobile phase: [water (0.225% FA)-ACN]; B %: 18%-48%, 10 min). Compound 206 or 3-[6-amino-1-[(4-amino-3-methyl-phenyl)methyl]pyrazolo[3,4-d]pyrimidine-4-yl]-2-fluoro-benzonitrile (111.35 mg, 59% yield, 97.78% purity) was obtained as a white solid. $^1$H NMR (400 MHz, DMSO-d$_6$) δ=8.21-8.10 (m, 2H), 8.00-7.94 (m, 1H), 7.66-7.52 (m, 1H), 7.16-7.07 (m, 2H), 6.92-6.80 (m, 2H), 6.56-6.46 (m, 1H), 5.34-5.15 (m, 2H), 4.93-4.67 (m, 2H), 2.06-1.88 (m, 3H).

Example 1.6: Production 3-(6-amino-1-(4-amino-3-(trifluoromethyl)benzyl)-1H-pyrazolo[3,4-d]pyrimidine-4-yl)benzonitrile (Compound 210)

1.6.1. Production of 4-chloro-1-(4-nitro-3-(trifluoromethyl)benzyl)-1H-pyrazolo[3,4-d]pyrimidine-6-amine (Intermediate Compound S9)

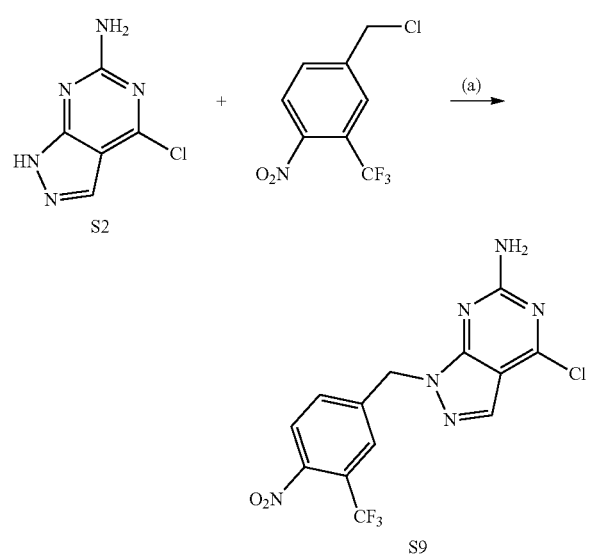

Reagents and Conditions: (a) K$_2$CO$_3$, DMAc, 80° C., 16 h.

To a solution of 4-(chloromethyl)-1-nitro-2-(trifluoromethyl)benzene (3.39 g, 1.2 eq) and 4-chloro-1H-pyrazolo[3,4-d]pyrimidine-6-amine (2 g, 1 eq) in DMF (20 mL) was added K$_2$CO$_3$ (3.26 g, 2 eq). The mixture was stirred at 80° C. for 16 hr. The reaction mixture was concentrated under reduced pressure to remove DMF to give a residue. The residue was purified by flash silica gel chromatography (ISCO®; 40 g SEPAFLASH® Silica Flash Column, Eluent of 0~100% Ethyl acetate/Petroleum ether gradient @ 45 mL/min). Compound 4-chloro-1-[[4-nitro-3-(trifluoromethyl)phenyl]methyl]pyrazolo[3,4-d]pyrimidine-6-amine (2 g, 45% yield) was obtained as a yellow solid. MS: m/z=373.3 (M+1, ESI+)

1.6.2. Production of 3-(6-amino-1-(4-amino-3-(trifluoromethyl)benzyl)-1H-pyrazolo[3,4-d]pyrimidine-4-yl)benzonitrile (Compound 210)

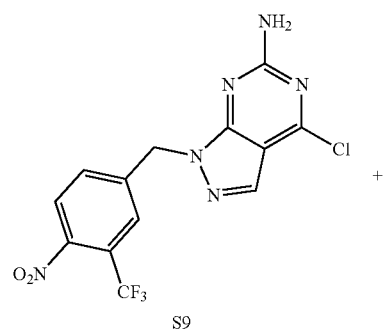

S9

-continued

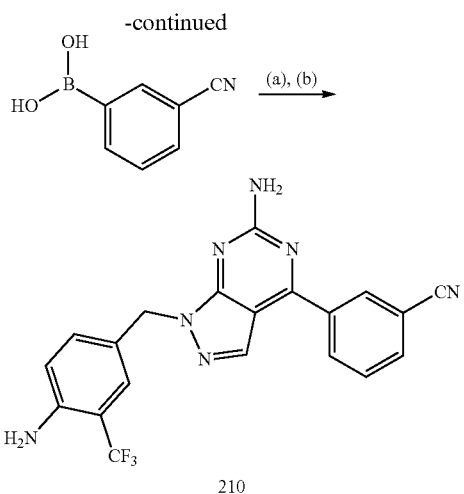

210

Reagents and condition: (a) Pd(PPh₃)₄, K₂CO₃, dioxane/H₂O, 100° C., 15 h; (b) Fe, NH₄Cl, EtOH/H₂O, 60° C., 2 h.

Stage 1: Production of 3-(6-amino-1-(4-nitro-3-(trifluoromethyl)benzyl)-1H-pyrazolo[3,4-d]pyrimidine-4-yl)benzonitrile A mixture of (3-cyanophenyl)boronic acid (236 mg, 1.5 eq), intermediate compound S9 or 4-chloro-1-[[4-nitro-3-(trifluoromethyl) phenyl]methyl]pyrazolo[3,4-d]pyrimidine-6-amine (400 mg, 1 eq), Pd(PPh₃)₄ (124 mg, 0.1 eq), K₂CO₃ (296 mg, 2 eq) in dioxane (10 mL) and water (1 mL) was degassed and purged with nitrogen for three times, and then the mixture was stirred at 100° C. for 15 hr under nitrogen atmosphere. The reaction mixture was concentrated under reduced pressure to remove dioxane and water to give a residue. The residue was purified by flash silica gel chromatography (ISCO®; 12 g SEPAFLASH® Silica Flash Column, Eluent of 0~100% Ethyl acetate/Petroleum ether gradient @ 35 mL/min). Compound 3-[6-amino-1-[[4-nitro-3-(trifluoromethyl)phenyl]methyl]pyrazolo[3,4-d]pyrimidine-4-yl]benzonitrile (300 mg, 63% yield) was obtained as a yellow oil. MS: m/z=440.1 (M+1, ESI+).

Stage 2: Production of 3-(6-amino-1-(4-amino-3-(trifluoromethyl)benzyl)-1H-pyrazolo[3,4-d]pyrimidine-4-yl)benzonitrile (Compound 210)

To a solution of 3-[6-amino-1-[[4-nitro-3-(trifluoromethyl)phenyl]methyl]pyrazolo[3,4-d]pyrimidine-4-yl]benzonitrile (290 mg, 1 eq) in water (5 mL) and ethanol (15 mL) was added iron dust (190 mg, 5 eq) and NH₄Cl (292 mg, 8 eq). The mixture was stirred at 60° C. for 2 hr. The reaction mixture was concentrated under reduced pressure to remove ethanol to give a residue. The residue was purified by prep-HPLC (column: Unisil 3-100 C18 Ultra 150*50 mm*3 µm; mobile phase: [water (0.225% FA)-ACN]; B %: 43%-63%, 10 min). Compound 210 or 3-[6-amino-1-[[4-amino-3-(trifluoromethyl)phenyl]methyl]pyrazolo[3,4-d]pyrimidine-4-yl]benzonitrile (59.98 mg, 21% yield, 99.14% purity) was obtained as a white solid. $^1$H NMR (400 MHz, DMSO-d6) δ=8.52 (s, 1H), 8.47 (d, J=8.1 Hz, 1H), 8.38 (s, 1H), 8.06 (d, J=7.7 Hz, 1H), 7.79 (t, J=7.8 Hz, 1H), 7.30 (d, J=1.5 Hz, 1H), 7.23-7.17 (m, 1H), 7.10 (s, 2H), 6.78 (d, J=8.4 Hz, 1H), 5.59 (s, 2H), 5.30 (s, 2H).

Example 1.7: Production of 3-(6-amino-1-(4-amino-3-(trifluoromethyl)benzyl)-1H-pyrazolo[3,4-d]pyrimidine-4-yl)-2-fluorobenzonitrile (Compound 211)

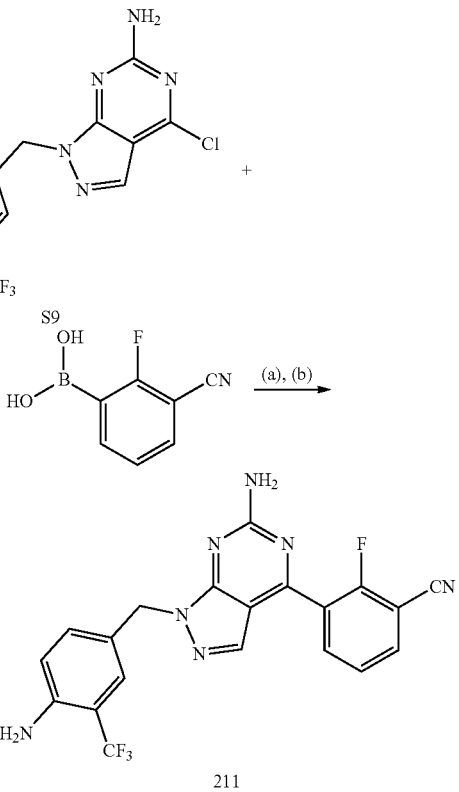

211

Reagents and condition: (a) Pd(PPh₃)₄, K₂CO₃, dioxane/H₂O, 100° C., 15h; (b) Fe, NH₄Cl, EtOH/H₂O, 60° C., 2 h.

Stage 1: Production of 3-(6-amino-1-(4-nitro-3-(trifluoromethyl)benzyl)-1H-pyrazolo[3,4-d]pyrimidine-4-yl)-2-fluorobenzonitrile A mixture of (3-cyano-2-fluoro-phenyl)boronic acid (265 mg, 1.5 eq), intermediate compound S9 or 4-chloro-1-[[4-nitro-3-(trifluoromethyl)phenyl]methyl]pyrazolo[3,4-d]pyrimidine-6-amine (400 mg, 1 eq), Pd(PPh₃)₄ (124 mg, 0.1 eq), K₂CO₃ (296 mg, 2 eq) in dioxane (10 mL) and water (1 mL) was degassed and purged with nitrogen for three times, and then the mixture was stirred at 100° C. for 15 hr under nitrogen atmosphere. The reaction mixture was concentrated under reduced pressure to remove dioxane and water to give a residue. The residue was purified by flash silica gel chromatography (ISCO®; 12 g SEPAFLASH® Silica Flash Column, Eluent of 0~100% Ethyl acetate/Petroleum ether gradient @ 35 mL/min). Compound 3-[6-amino-1-[[4-nitro-3-(trifluoromethyl)phenyl]methyl]pyrazolo[3,4-d]pyrimidine-4-yl]-2-fluoro-benzonitrile (350 mg, 71% yield) was obtained as a yellow oil. MS: m/z=458.3 (M+1, ESI+).

Stage 2: Production of 3-(6-amino-1-(4-amino-3-(trifluoromethyl)benzyl)-1H-pyrazolo[3,4-d]pyrimidine-4-yl)-2-fluorobenzonitrile (Compound 211)

To a solution of 3-[6-amino-1-[[4-nitro-3-(trifluoromethyl)phenyl]methyl]pyrazolo[3,4-d]pyrimidine-4-yl]-2- fluoro-benzonitrile (300 mg, 1 eq) in ethanol (15 mL) and water (5 mL) was added iron dust (183 mg, 5 eq) and NH$_4$Cl (280 mg, 8 eq). The mixture was stirred at 60° C. for 2 hr. The reaction mixture was concentrated under reduced pressure to remove ethanol to give a residue. The residue was purified by prep-HPLC (column: Unisil 3-100 C18 Ultra 150*50 mm*3 µm; mobile phase: [water (0.225% FA)-ACN]; B %: 43%-63%, 10 min). Compound 211 or 3-[6-amino-1-[[4-amino-3-(trifluoromethyl)phenyl]methyl]pyrazolo[3,4-d]pyrimidine-4-yl]-2-fluoro-benzonitrile (41.58 mg, 15% yield, 98.23% purity) was obtained as a solid off-white. $^1$H NMR (400 MHz, DMSO-d$_6$) δ=8.20-8.11 (m, 2H), 8.00 (d, J=3.5 Hz, 1H), 7.60 (t, J=7.8 Hz, 1H), 7.30 (d, J=1.6 Hz, 1H), 7.23-7.17 (m, 1H), 7.15 (s, 2H), 6.78 (d, J=8.4 Hz, 1H), 5.60 (s, 2H), 5.29 (s, 2H).

Example 1.8: Production of 3-(6-amino-1-(2,6-difluorobenzyl)-1H-pyrazolo[3,4-d]pyrimidine-4-yl)-2-fluorobenzonitrile (Compound 213)

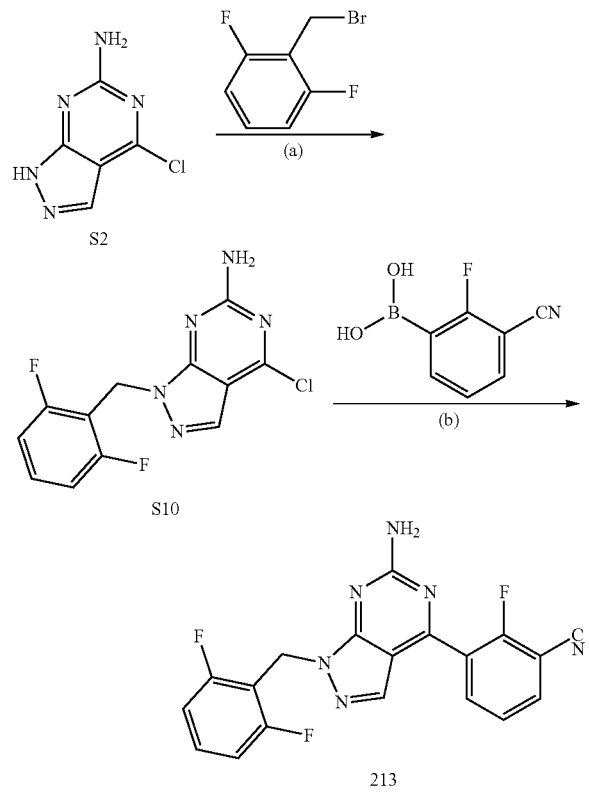

Reagents and Conditions: (a) K$_2$CO$_3$, DMAc, 80° C., 16 h; (b) Pd(PPh$_3$)$_4$, K$_2$CO$_3$, dioxane/H$_2$O, 80° C., 16 h.

Stage 1: Production of 4-chloro-1-[(2,6-difluorophenyl)methyl]pyrazolo[3,4-d]pyrimidine-6-amine (Intermediate Compound S10)

To a solution of 4-chloro-1H-pyrazolo[3,4-d]pyrimidine-6-amine (8 g, 47.18 mmol, 1 eq) and 2-(bromomethyl)-1,3-difluoro-benzene (11.72 g, 56.61 mmol, 1.2 eq) in DMAc (100 mL) was added K$_2$CO$_3$ (13.04 g, 94.36 mmol, 2 eq). The mixture was stirred at 80° C. for 16 hr. The reaction mixture was filtered and concentrated under reduced pressure to give a residue. The residue was purified by flash silica gel chromatography (ISCO®; 80 g SEPAFLASH® Silica Flash Column, Eluent of 0~100% Ethyl acetate/Petroleum ether gradient @ 60 mL/min). Intermediate compound S10 or 4-chloro-1-[(2,6-difluorophenyl)methyl]pyrazolo[3,4-d]pyrimidine-6-amine (4 g, 13.53 mmol, 29% yield) was obtained as a white solid. $^1$H NMR (400 MHz, DMSO-d$_6$) δ=8.35-7.77 (m, 1H), 7.53-7.41 (m, 1H), 7.40-7.31 (m, 2H), 7.19-6.98 (m, 2H), 5.60-5.20 (m, 2H).

Stage 2: Production of 3-(6-amino-1-(2,6-difluorobenzyl)-1H-pyrazolo[3,4-d]pyrimidine-4-yl)-2-fluorobenzonitrile (Compound 213)

A mixture of (3-cyano-2-fluoro-phenyl)boronic acid (251 mg, 1.5 eq), intermediate compound S10 or 4-chloro-1-[(2,6-difluorophenyl) methyl]pyrazolo[3,4-d]pyrimidine-6-amine (300 mg, 1 eq), Pd(PPh$_3$)$_4$ (117 mg, 0.1 eq), K$_2$CO$_3$ (280 mg, 2 eq) in dioxane (10 mL) and water (2 mL) was degassed and purged with nitrogen for three times, and then the mixture was stirred at 80° C. for 16 hr under nitrogen atmosphere. The reaction mixture was concentrated under reduced pressure to give a residue. The residue was purified by prep-HPLC (column: Unisil 3-100 C18 Ultra 150*50 mm*3 nm; mobile phase: [water (0.225% FA)-ACN]; B %: 45%-65%, 10 min). Compound 213 or 3-[6-amino-1-[(2,6-difluorophenyl)methyl]pyrazolo[3,4-d]pyrimidine-4-yl]-2-fluoro-benzonitrile (118.51 mg, 30% yield, 98.93% purity) was obtained as a white solid. $^1$H NMR (400 MHz, DMSO-d$_6$) δ=8.22-8.09 (m, 2H), 7.95 (d, J=3.5 Hz, 1H), 7.60 (t, J=7.8 Hz, 1H), 7.52-7.39 (m, 1H), 7.19 (s, 2H), 7.13 (t, J=8.0 Hz, 2H), 5.45 (s, 2H).

Example 1.9: Production of 3-(6-amino-1-(4-amino-2-fluorobenzyl)-1H-pyrazolo[3,4-d]pyrimidine-4-yl)benzonitrile (Compound 209)

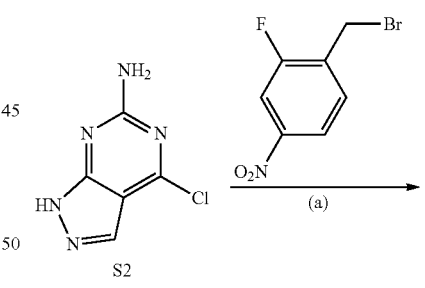

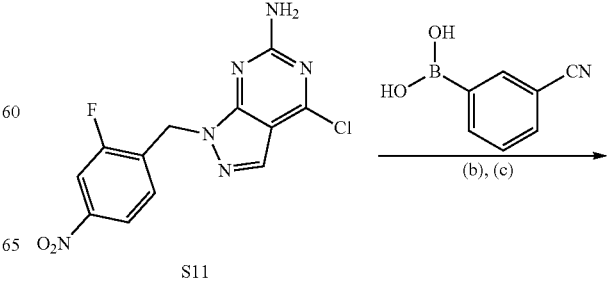

-continued

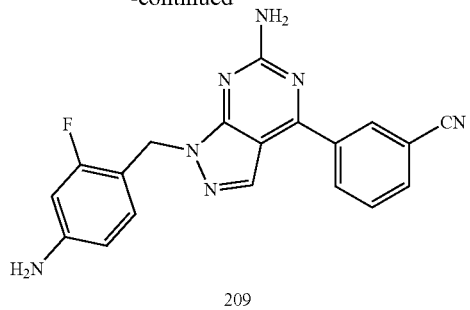

209

Reagents and Conditions: (a) K₂CO₃, DMAc, 60° C., 16 h; (b) Pd(PPh₃)₄, K₂CO₃, dioxane/H₂O, 80° C., 16 h; (c) Fe, NH₄Cl, EtOH/H₂O, 80° C., 3 h.

Stage 1: Production of 4-chloro-1-(2-fluoro-4-nitrobenzyl)-1H-pyrazolo[3,4-d]pyrimidine-6-amine (Intermediate Compound S11)

To a solution of 4-chloro-1H-pyrazolo[3,4-d]pyrimidine-6-amine (5.1 g, 1 eq) and 1-(bromomethyl)-2-fluoro-4-nitrobenzene (7 g, 1 eq) in DMF (20 mL) was added K₂CO₃ (8.3 g, 2 eq). The mixture was stirred at 60° C. for 16 hr. The reaction mixture was filtered and concentrated under reduced pressure to give a residue. The residue was purified by flash silica gel chromatography (ISCO®; 40 g SEPA-FLASH® Silica Flash Column, Eluent of 0~100% Ethyl acetate/Petroleum ether gradient @ 40 mL/min). Intermediate compound S11 or 4-chloro-1-[(2-fluoro-4-nitro-phenyl) methyl]pyrazolo[3,4-d]pyrimidine-6-amine (5 g, 52% yield) was obtained as a yellow solid. ¹H NMR (400 MHz, DMSO-d₆) δ=8.15-8.11 (m, 1H), 8.08-8.06 (m, 1H), 8.05-8.01 (m, 1H), 7.47-7.38 (m, 2H), 7.33 (t, J=8.0 Hz, 1H), 5.57 (s, 2H). MS: m/z=323.3 (M+1, ESI+).

Stage 2: Production of 3-(6-amino-1-(2-fluoro-4-nitrobenzyl)-1H-pyrazolo[3,4-d]pyrimidine-4-yl) benzonitrile A mixture of (3-cyanophenyl)boronic acid (341 mg, 1.5 eq), intermediate compound S11 or 4-chloro-1-[(2-fluoro-4-nitro-phenyl)methyl]pyrazolo[3,4-d]pyrimidine-6-amine (500 mg, 1 eq), Pd(PPh₃)₄ (179 mg, 0.1 eq), K₂CO₃ (428 mg, 2 eq) in dioxane (10 mL) and water (2 mL) was degassed and purged with nitrogen for three times, and then the mixture was stirred at 100° C. for 16 hr under nitrogen atmosphere. The reaction mixture was concentrated under reduced pressure to remove dioxane to give a residue. The residue was purified by prep-HPLC (column: Unisil 3-100 C18 Ultra 150*50 mm*3 μm; mobile phase: [water (0.225% FA)-ACN]; B %: 45%-65%, 10 min). Compound 3-[6-amino-1-[(2-fluoro-4-nitro-phenyl)methyl]pyrazolo[3,4-d]pyrimidine-4-yl]benzonitrile (200 mg, 33% yield, 99% purity) was obtained as a yellow solid. ¹H NMR (400 MHz, DMSO-d₆) δ=8.55-8.51 (m, 1H), 8.49-8.46 (m, 1H), 8.31-8.26 (m, 1H), 8.18-8.01 (m, 4H), 7.38-7.28 (m, 1H), 7.22-7.05 (m, 2H), 5.62 (s, 2H). MS: m/z=389.9 (M+1, ESI+).

Stage 3: Production of 3-(6-amino-1-(4-amino-2-fluorobenzyl)-1H-pyrazolo[3,4-d]pyrimidine-4-yl) benzonitrile (Compound 209)

To a solution of 3-[6-amino-1-[(2-fluoro-4-nitro-phenyl) methyl]pyrazolo[3,4-d]pyrimidine-4-yl]benzonitrile (200 mg, 513.69 μmol, 1 eq) in ethanol (15 mL) and water (5 mL) were added iron dust (143 mg, 5 eq) and NH₄Cl (219 mg, 8 eq). The mixture was stirred at 80° C. for 3 hr. The reaction mixture was concentrated under reduced pressure to remove ethanol and water to give a residue. The residue was purified by prep-HPLC (column: Unisil 3-100 C18 Ultra 150*50 mm*3 μm; mobile phase: [water (0.225% FA)-ACN]; B %: 30%-50%, 10 min). Compound 209 or 3-[6-amino-1-[(4-amino-2-fluoro-phenyl)methyl]pyrazolo[3,4-d]pyrimidine-4-yl]benzonitrile (36.42 mg, 19% yield, 97.66% purity) was obtained as an off-white solid. ¹H NMR (400 MHz, DMSO-d₆) δ=8.51 (s, 1H), 8.49-8.44 (m, 1H), 8.35 (s, 1H), 8.08-8.01 (m, 1H), 7.79 (t, J=7.8 Hz, 1H), 7.07 (s, 2H), 6.88 (t, J=8.5 Hz, 1H), 6.36-6.22 (m, 2H), 5.40 (s, 2H), 5.28 (s, 2H).

Example 1.10: Production of 3-(6-amino-1-(4-amino-2,6-difluorobenzyl)-1H-pyrazolo[3,4-d]pyrimidine-4-yl)benzonitrile (Compound 207)

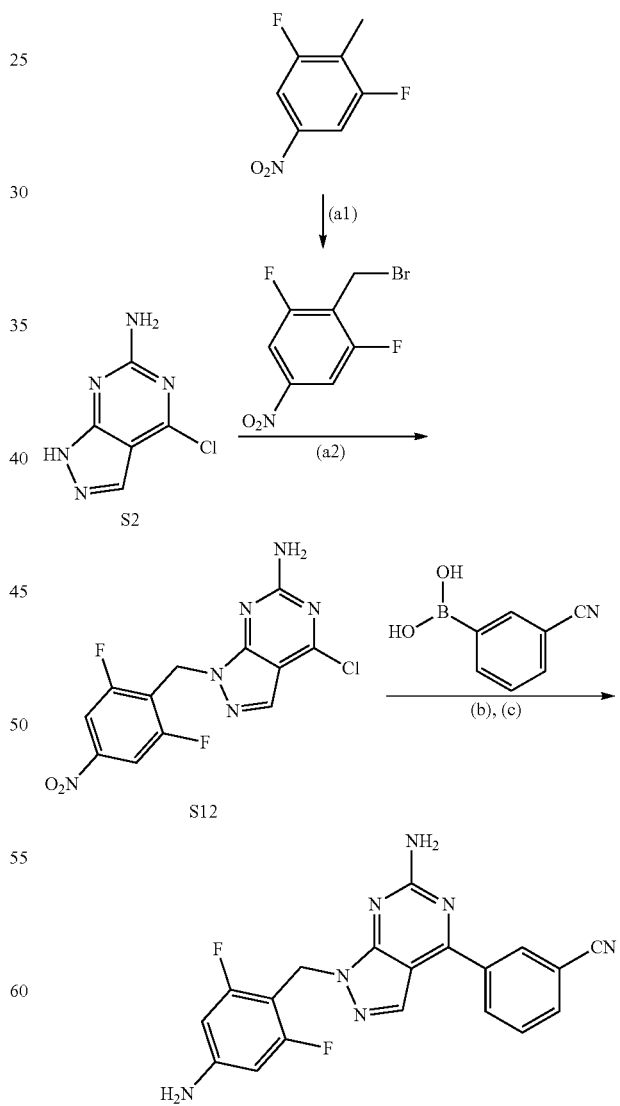

207

Reagents and Conditions: (a1) NBS, AIBN, CC14, 90° C., 15h; (a2) K$_2$CO$_3$, DMAc, 80° C., 3 h; (b) Pd(dppf)Cl$_2$, K$_2$CO$_3$, dioxane/H$_2$O, 110° C., 2 h, MW; (c) Fe, NH$_4$Cl, EtOH/H$_2$O, 80° C., 1 h.

Stage 1: Production of 4-chloro-1-[(2,6-difluoro-4-nitro-phenyl)methyl]pyrazolo[3,4-d]pyrimidine-6-amine (Intermediate Compound S12)

To the solution of 1,3-difluoro-2-methyl-5-nitro-benzene (2 g, 11.55 mmol, 1 eq) in tetrachloromethane (50 mL) were added NBS (3.08 g, 17.33 mmol, 1.5 eq) and AIBN (190 mg, 1.16 mmol, 0.1 eq). Then the mixture was stirred at 90° C. for 15 h. The reaction mixture was concentrated in vacuum to give a residue. To the residue was added DMAc (50 mL), 4-chloro-1H-pyrazolo[3,4-d]pyrimidine-6-amine (1.96 g, 11.55 mmol, 1 eq) and K$_2$CO$_3$ (3.19 g, 23.11 mmol, 2 eq). Then the mixture was stirred at 80° C. for 3 h. To the mixture was added water (130 mL) and ethyl acetate (130 mL), and the layers were separated. The aqueous was extracted with ethyl acetate (130 mL×2). Combined the organic phase to wash by brines (150 mL×2), dry over anhydrous sodium sulfate, filter and the filtrate was concentrated in vacuum to give a residue. The residue was purified by flash silica gel chromatography (40 g SEPAFLASH® Silica Flash Column, Eluent of 0~30% Ethyl acetate/Petroleum ether gradient @ 60 mL/min). Intermediate compound S12 or 4-chloro-1-[(2, 6-difluoro-4-nitro-phenyl) methyl]pyrazolo[3,4-d]pyrimidine-6-amine (1.5 g, 4.26 mmol, 37% yield, 96.7% purity) was obtained as a yellow solid.

Stage 2: Production of 3-[6-amino-1-[(2,6-difluoro-4-nitro-phenyl) methyl]pyrazolo[3,4-d]pyrimidine-4-yl]benzonitrile Intermediate compound S12 or 4-chloro-1-[(2,6-difluoro-4-nitro-phenyl)methyl]pyrazolo[3,4-d]pyrimidine-6-amine (500 mg, 1.47 mmol, 1 eq), (3-cyanophenyl)boronic acid (323 mg, 2.20 mmol, 1.5 eq), K$_2$CO$_3$ (405 mg, 2.94 mmol, 2 eq) and Pd(dppf)Cl$_2$ (107 mg, 146.77 μmol, 0.1 eq) were taken up into a microwave tube in dioxane (6 mL) and water (2 mL). The sealed tube was heated at 110° C. for 2 h under microwave. After that the mixture was added water (80 mL) and ethyl acetate (80 mL), and the layers were separated. The aqueous was extracted with ethyl acetate (80 mL×3). Combined the organic phase to dry over anhydrous sodium sulfate, filter and the filtrate was concentrated in vacuum to give a residue. The residue was purified by flash silica gel chromatography (20 g SEPAFLASH® Silica Flash Column, Eluent of 0~100% Ethyl acetate/Petroleum ether gradient @ 50 mL/min). Compound 3-[6-amino-1-[(2,6-difluoro-4-nitro-phenyl)methyl]pyrazolo[3,4-d]pyrimidine-4-yl]benzonitrile (200 mg, 441.90 μmol, 30% yield, 90% purity) was obtained as a yellow solid. $^1$H NMR (400 MHz, DMSO-d$_6$) δ=8.49 (d, J=1.2 Hz, 1H), 8.47-8.41 (m, 1H), 8.35 (s, 1H), 8.16-8.07 (m, 2H), 8.06 (td, J=1.3, 7.8 Hz, 1H), 7.79 (t, J=7.9 Hz, 1H), 7.16 (s, 2H), 5.55 (s, 2H). MS: m/z=408.0 (M+1, ESI+).

Stage 3: Production of 3-[6-amino-1-[(4-amino-2,6-difluoro-phenyl) methyl]pyrazolo[3,4-d]pyrimidine-4-yl]benzonitrile (Compound 207)

To the solution of 3-[6-amino-1-[(2,6-difluoro-4-nitro-phenyl)methyl]pyrazolo[3,4-d]pyrimidine-4-yl]benzonitrile (200 mg, 491.00 μmol, 1 eq) in ethanol (8 mL) and water (2 mL) were added iron dust (137 mg, 2.45 mmol, 5 eq) and NH$_4$Cl (210 mg, 3.93 mmol, 8 eq). Then the mixture was stirred at 80° C. for 1 h. The reaction mixture was filtered and the filtrate was concentrated in vacuum. After that, to the mixture was added water (30 mL) and then extracted with ethyl acetate (30 mL×3). Combined the organic phase to dry over anhydrous sodium sulfate, filter and the filtrate was concentrated in vacuum to give a residue. The residue was purified by prep-HPLC (column: Welch Ultimate XB-CN 250*70*10 μm; mobile phase: [Hexane-EtOH (0.1% ammonia hydroxide)]; B %: 30%-70%, 15 min). Compound 207 or 3-[6-amino-1-[(4-amino-2,6-difluoro-phenyl)methyl]pyrazolo[3,4-d]pyrimidine-4-yl]benzonitrile (62.95 mg, 163.33 μmol, 33% yield, 97.91% purity) was obtained as a yellow solid. $^1$H NMR (400 MHz, DMSO-d$_6$) δ=8.49 (t, J=1.4 Hz, 1H), 8.45 (td, J=1.4, 7.9 Hz, 1H), 8.29 (s, 1H), 8.05 (td, J=1.3, 7.7 Hz, 1H), 7.79 (t, J=7.8 Hz, 1H), 7.07 (s, 2H), 6.30-6.06 (m, 2H), 5.80 (s, 2H), 5.25 (s, 2H).

Example 1.11: Production of 3-(6-amino-1-(4-amino-2-fluorobenzyl)-1H-pyrazolo[3,4-d]pyrimidine-4-yl)-2-fluorobenzonitrile (Compound 203)

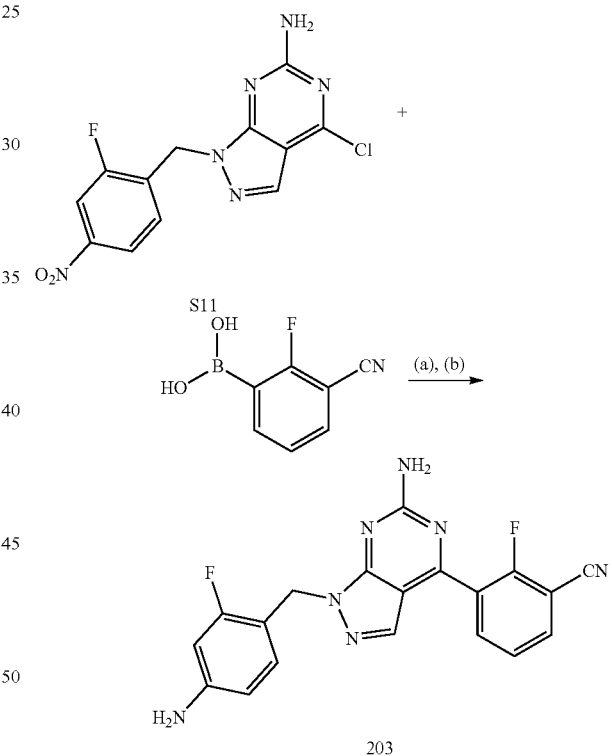

203

Reagents and condition: (a) Pd(dppf)Cl$_2$, K$_2$CO$_3$, dioxane/H$_2$O, 110° C., 16h; (b) Fe, NH$_4$Cl, EtOH/H$_2$O, 80° C., 3 h.

Stage 1: Production of 3-(6-amino-1-(2-fluoro-4-nitrobenzyl)-1H-pyrazolo[3,4-d]pyrimidine-4-yl)-2-fluorobenzonitrile A mixture of (3-cyano-2-fluoro-phenyl)boronic acid (383 mg, 2.33 mmol, 1.5 eq), intermediate compound S11 or 4-chloro-1-[(2-fluoro-4-nitro-phenyl)methyl]pyrazolo[3,4-d]pyrimidine-6-amine (500 mg, 1 eq), Pd(PPh$_3$)$_4$ (179 mg, 0.1 eq), K$_2$CO$_3$ (428 mg, 2 eq) in dioxane (10 mL) and water (2 mL) was degassed and purged with nitrogen for three times, and then the mixture was stirred at 100° C. for 16 hr under nitrogen atmosphere. The reaction mixture was concentrated under reduced pressure to remove dioxane to give a residue. The residue was purified by flash silica gel chromatography (ISCO®; 12 g SEPAFLASH® Silica Flash Column, Eluent of 0~80% Ethyl acetate/Petroleum ether gradient @ 30 mL/min). Compound 3-[6-amino-1-[(2-fluoro-4-nitro-phenyl)methyl]pyrazolo[3,4-d]pyrimidine-4-yl]-2-fluoro-benzonitrile (300 mg, 48% yield) was obtained as a yellow solid. MS: m/z=407.9 (M+1, ESI+).

Stage 2: Production of 3-(6-amino-1-(4-amino-2-fluorobenzyl)-1H-pyrazolo[3,4-d]pyrimidine-4-yl)-2-fluorobenzonitrile (Compound 203)

To a solution of 3-[6-amino-1-[(2-fluoro-4-nitro-phenyl)methyl]pyrazolo[3,4-d]pyrimidine-4-yl]-2-fluoro-benzonitrile (209 mg, 1 eq) in ethanol (15 mL) and water (5 mL) was added iron dust (143 mg, 5 eq) and NH$_4$Cl (219 mg, 8 eq). The mixture was stirred at 80° C. for 3 hr. The reaction mixture was concentrated under reduced pressure to remove ethanol to give a residue. The residue was purified by prep-HPLC (column: Unisil 3-100 C18 Ultra 150*50 mm*3 μm; mobile phase: [water (0.225% FA)-ACN]; B %: 33%-53%, 10 min), 80% purity desired compound was obtained, then the residue was purified by second prep-HPLC (column: Phenomenex Gemini-NX C18 75*30 mm*3 μm; mobile phase: [water (0.225% FA)-ACN]; B %: 22%-52%, 7 min). Compound 203 or 3-[6-amino-1-[(4-amino-2-fluoro-phenyl)methyl]pyrazolo[3,4-d]pyrimidine-4-yl]-2-fluoro-benzonitrile (62.37 mg, 31% yield, 97.40% purity) was obtained as a white solid. $^1$H NMR (400 MHz, DMSO-d$_6$) δ=8.21-8.10 (m, 2H), 7.98 (d, J=3.7 Hz, 1H), 7.61 (t, J=7.8 Hz, 1H), 7.14 (s, 2H), 6.97-6.84 (m, 1H), 6.32 (s, 1H), 6.31-6.28 (m, 1H), 5.42 (s, 2H), 5.27 (s, 2H).

Example 1.12: Production of 3-(6-amino-1-(4-amino-2,6-difluorobenzyl)-1H-pyrazolo[3,4-d]pyrimidine-4-yl)-2-fluorobenzonitrile (Compound 208)

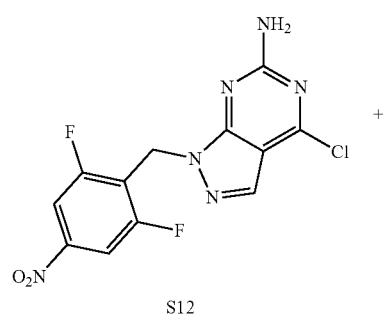

S12

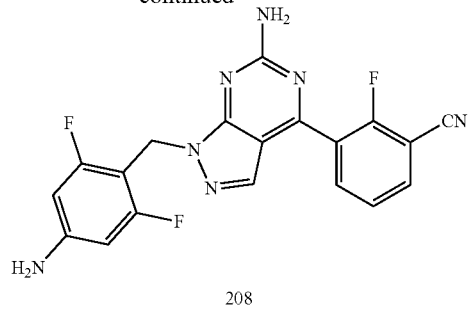

208

Reagents and condition: (a) Pd(dppf)Cl$_4$, K$_2$CO$_3$, dioxane/H$_2$O, 110° C., 15h; (b) Fe, NH$_4$Cl, EtOH/H$_2$O, 80° C., 1 h.

Stage 1: Production of 3-[6-amino-1-[(2,6-difluoro-4-nitro-phenyl)methyl]pyrazolo[3,4-d]pyrimidine-4-yl]-2-fluoro-benzonitrile To the solution of intermediate compound S12 or 4-chloro-1-[(2,6-difluoro-4-nitro-phenyl)methyl]pyrazolo[3,4-d]pyrimidine-6-amine (400 mg, 1.17 mmol, 1 eq) in water (2 mL) and dioxane (8 mL) were added (3-cyano-2-fluoro-phenyl)boronic acid (300 mg, 1.82 mmol, 1.55 eq), Pd(dppf)Cl$_2$ (86 mg, 117.41 μmol, 0.1 eq) and K$_2$CO$_3$ (325 mg, 2.35 mmol, 2 eq). Then the mixture was stirred at 110° C. for 15 h. After that the mixture was concentrated in vacuum to give a residue, and it was purified by flash silica gel chromatography (12 g SEPAFLASH® Silica Flash Column, Eluent of 20~100% Ethyl acetate/Petroleum ether gradient @ 50 mL/min). Compound 3-[6-amino-1-[(2,6-difluoro-4-nitro-phenyl)methyl]pyrazolo[3,4-d]pyrimidine-4-yl]-2-fluoro-benzonitrile (140 mg, 322.25 μmol, 27% yield, 97.9% purity) was obtained as a yellow solid. $^1$H NMR (400 MHz, DMSO-d$_6$) δ=8.20-8.12 (m, 2H), 8.12-8.05 (m, 2H), 7.99 (d, J=3.6 Hz, 1H), 7.60 (t, J=7.8 Hz, 1H), 7.22 (s, 2H), 5.54 (s, 2H). MS: m/z=426.1 (M+1, ESI+).

Stage 2: Production of 3-(6-amino-1-(4-amino-2,6-difluorobenzyl)-1H-pyrazolo[3,4-d]pyrimidine-4-yl)-2-fluorobenzonitrile (Compound 208)

To the solution of 3-[6-amino-1-[(2,6-difluoro-4-nitro-phenyl)methyl]pyrazolo[3,4-d]pyrimidine-4-yl]-2-fluoro-benzonitrile (140 mg, 329.16 μmol, 1 eq) in ethanol (8 mL) and water (2 mL) were added iron dust (92 mg, 1.65 mmol, 5 eq) and NH$_4$Cl (140 mg, 2.63 mmol, 8 eq). Then the mixture was stirred at 80° C. for 1 h. The reaction mixture was filtered and the filtrate was concentrated in vacuum. To the mixture were added water (50 mL) and then extracted with ethyl acetate (30 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% NH$_3$·H$_2$O)]; B %: 35%-75%, 15 min). Compound 208 or 3-[6-amino-1-[(4-amino-2,6-difluoro-phenyl)methyl]pyrazolo[3,4-d]pyrimidine-4-yl]-2-fluoro-benzonitrile (44.01 mg, 109.41 μma 33% yield, 98.28% purity) was obtained as a yellow solid. $^1$H NMR (400 MHz, DMSO-d$_6$) δ=8.14 (dd, J=6.7, 7.7 Hz, 2H), 7.93 (d, J=3.6 Hz, 1H), 7.60 (t, J=7.8 Hz, 1H), 7.13 (s, 2H), 6.27-6.07 (m, 2H), 5.80 (s, 2H), 5.24 (s, 2H).

Example 1.13: Production of 4-[6-amino-1-[(2,6-difluorophenyl)methyl]pyrazolo[3,4-d]pyrimidine-4-yl]pyridine-2-carbonitrile (Compound 234)

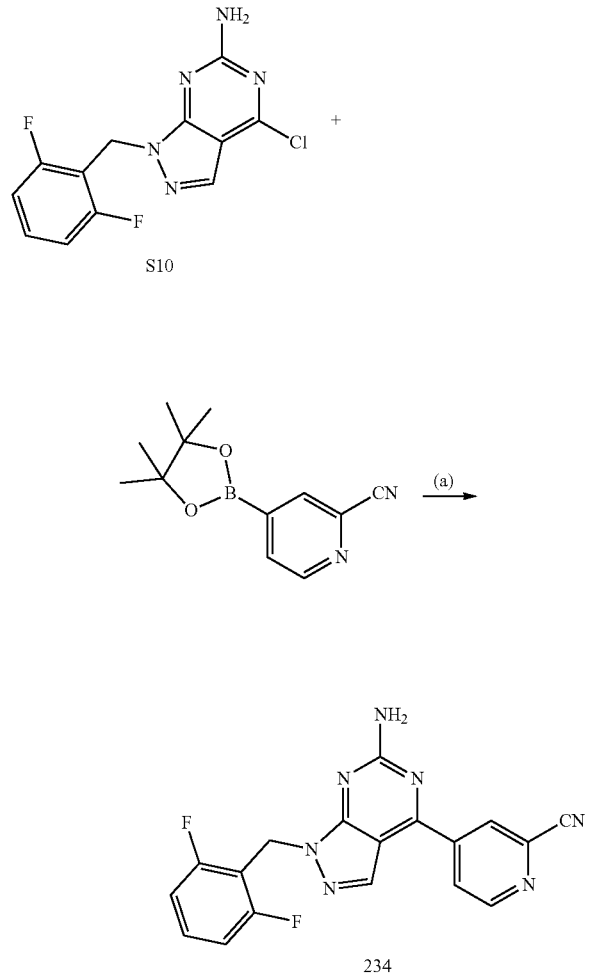

Reagents and condition: (a) Pd(dppf)Cl$_2$, K$_2$CO$_3$, dioxane/H$_2$O, 80° C., 16 h.

A mixture of intermediate compound S10 or 4-chloro-1-[(2,6-difluorophenyl)methyl]pyrazolo[3,4-d]pyrimidine-6-amine (300 mg, 1 eq), 4-(4,4,5,5-tetramethyl-1,3,2-dioxaborolan-2-yl)pyridine-2-carbonitrile (279 mg, 1.2 eq), K$_2$CO$_3$ (279 mg, 2 eq), Pd(dppf)Cl$_2$ (74 mg, 0.1 eq) in dioxane (10 mL) and water (2 mL) was degassed and purged with nitrogen for three times, and then the mixture was stirred at 80° C. for 16 hr under nitrogen atmosphere. The reaction mixture was concentrated under reduced pressure to remove dioxane to give a residue. The residue was purified by prep-HPLC (column: Unisil 3-100 C18 Ultra 150*50 mm*3 μm; mobile phase: [water (0.225% FA)-ACN]; B %: 38%-58%, 10 min). Compound 234 or 4-[6-amino-1-[(2,6-difluorophenyl)methyl]pyrazolo[3,4-d]pyrimidine-4-yl]pyridine-2-carbonitrile (124.39 mg, 34% yield, 99.96% purity) was obtained as a white solid. $^1$H NMR (400 MHz, DMSO-d6) δ=8.96 (d, J=5.1 Hz, 1H), 8.58 (d, J=0.6 Hz, 1H), 8.41-8.39 (m, 1H), 8.39-8.36 (m, 1H), 7.51-7.41 (m, 1H), 7.25 (s, 2H), 7.17-7.08 (m, 2H), 5.47 (s, 2H).

Example 1.14: Production of 4-(6-amino-1-(4-amino-2,6-difluorobenzyl)-1H-pyrazolo[3,4-d]pyrimidine-4-yl)picolinonitrile (Compound 226)

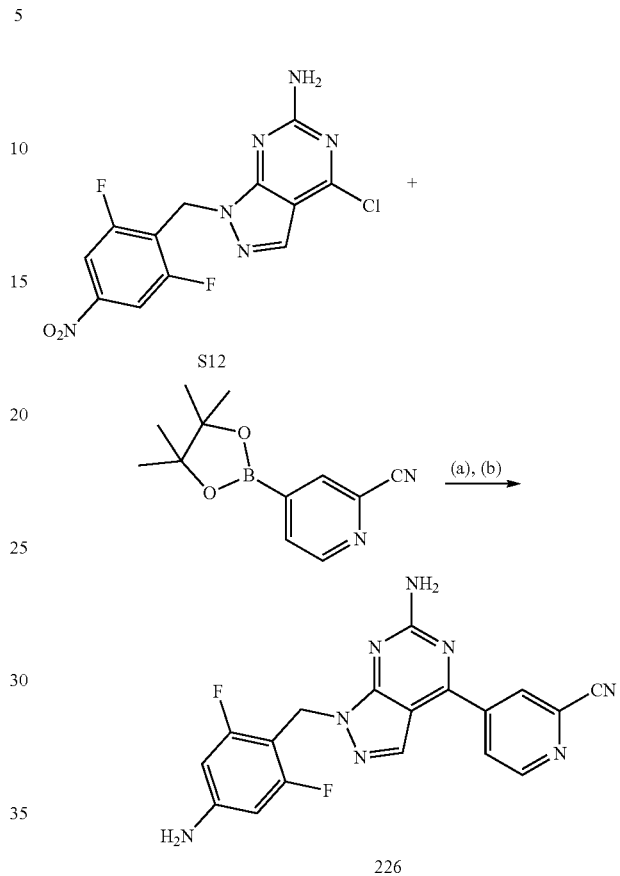

Reagents and condition: (a) Pd(dppf)Cl$_2$, K$_2$CO$_3$, dioxane/H$_2$O, 80° C., 16h; (b) Fe, NH$_4$Cl, EtOH/H$_2$O, 80° C., 2 h.

Stage 1: Production of 4-[6-amino-1-[(2,6-difluoro-4-nitro-phenyl)methyl]pyrazolo[3,4-d]pyrimidine-4-yl]pyridine-2-carbonitrile To the solution of intermediate compound S12 or 4-chloro-1-[(2,6-difluoro-4-nitro-phenyl)methyl]pyrazolo[3,4-d]pyrimidine-6-amine (400 mg, 1.17 mmol, 1 eq) in dioxane (10 mL) and water (2 mL) were added 4-(4,4,5,5-tetramethyl-1,3,2-dioxaborolan-2-yl) pyridine-2-carbonitrile (540 mg, 2.35 mmol, 2 eq), Pd(dppf)Cl$_2$ (86 mg, 117.41 μmol, 0.1 eq) and K$_2$CO$_3$ (325 mg, 2.35 mmol, 2 eq). Then the mixture was stirred at 100° C. for 15 h. The mixture was concentrated in vacuum to give a residue. The residue was purified by flash silica gel chromatography (20 g SEPA-FLASH® Silica Flash Column, Eluent of 0~60% Ethyl acetate/Petroleum ether gradient @ 50 mL/min). Compound 4-[6-amino-1-[(2,6-difluoro-4-nitro-phenyl)methyl]pyrazolo[3,4-d]pyrimidine-4-yl]pyridine-2-carbonitrile (300 mg, 625.68 μmol, 53% yield, 85% purity) was obtained as a yellow solid. $^1$H NMR (400 MHz, DMSO-d$_6$) δ=8.96 (d, J=5.1 Hz, 1H), 8.58 (s, 1H), 8.43 (s, 1H), 8.38 (dd, J=1.7, 5.1 Hz, 1H), 8.09 (br d, J=7.1 Hz, 2H), 7.28 (br s, 2H), 5.56 (s, 2H). MS: m/z=409.1 (M+1, ESI+).

Stage 2: Production of 4-[6-amino-1-[(4-amino-2,6-difluoro-phenyl) methyl]pyrazolo[3,4-d]pyrimidine-4-yl]pyridine-2-carbonitrile (Compound 226)

To the mixture of 4-[6-amino-1-[(2,6-difluoro-4-nitro-phenyl)methyl]pyrazolo[3,4-d]pyrimidine-4-yl]pyridine-2-carbonitrile (300 mg, 734.72 μmol, 1 eq) in water (3 mL) and ethanol (9 mL) were added iron dust (205 mg, 3.67 mmol, 5 eq) and NH$_4$Cl (314 mg, 5.88 mmol, 8 eq). Then the mixture was stirred at 80° C. for 2 h. The reaction mixture was filtered and the filtrate was concentrated in vacuum. To the mixture was added water (30 mL) and extracted with ethyl acetate (30 mL×3). Combined the organic phase to dry over anhydrous sodium sulfate, filter and the filtrate was concentrated in vacuum to give a residue. The residue was purified by prep-HPLC (column: Welch Ultimate XB-CN 250*70*10 μm; mobile phase: [Hexane-ethanol (0.1% NH$_3$·H$_2$O)]; B %: 30%-70%, 15 min). Compound 226 or 4-[6-amino-1-[(4-amino-2,6-difluoro-phenyl)methyl]pyrazolo[3,4-d]pyrimidine-4-yl]pyridine-2-carbonitrile (70.80 mg, 178.73 μmol, 24% yield, 95.51% purity) was obtained as a yellow solid. $^1$H NMR (400 MHz, DMSO-d6) δ=8.96 (dd, J=0.8, 5.1 Hz, 1H), 8.58 (dd, J=0.8, 1.6 Hz, 1H), 8.46-8.24 (m, 2H), 7.19 (s, 2H), 6.29-6.08 (m, 2H), 5.80 (s, 2H), 5.26 (s, 2H).

Example 1.15: Production of 4-(6-amino-1-(4-amino-3-methylbenzyl)-1H-pyrazolo[3,4-d]pyrimidine-4-yl)picolinonitrile (Compound 230)

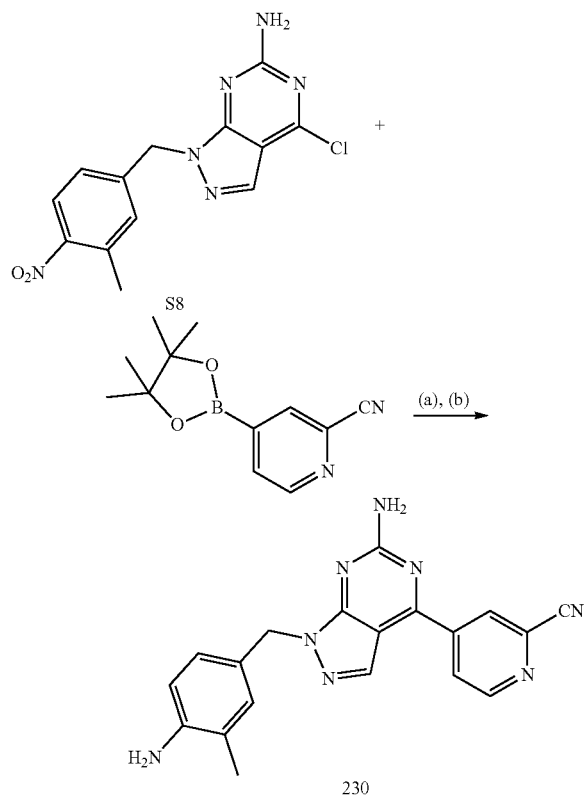

230

Reagents and condition: (a) Pd(dppf)Cl$_2$, K$_2$CO$_3$, dioxane/H$_2$O, 110° C., 16 h; (b) Fe, NH$_4$Cl, EtOH/H$_2$O, 60° C., 3 h.

Stage 1: Production of 4-(6-amino-1-(3-methyl-4-nitrobenzyl)-1H-pyrazolo[3,4-d]pyrimidine-4-yl) picolinonitrile A mixture of intermediate compound S8 or 4-chloro-1-[(3-methyl-4-nitro-phenyl)methyl]pyrazolo[3,4-d]pyrimidine-6-amine (500 mg, 1 eq), 4-(4,4,5,5-tetramethyl-1,3,2-dioxaborolan-2-yl)pyridine-2-carbonitrile (541 mg, 1.5 eq), K$_2$CO$_3$ (433 mg, 2 eq), Pd(dppf)Cl$_2$ (114 mg, 0.1 eq) in dioxane (10 mL) and water (2 mL) was degassed and purged with N2 for three times, and then the mixture was stirred at 110° C. for 16 hr under N$_2$ atmosphere. The reaction mixture was filtered and concentrated under reduced pressure to give a residue. The residue was purified by flash silica gel chromatography (ISCO®; 12 g SEPAFLASH® Silica Flash Column, Eluent of 0~100% Ethyl acetate/Petroleum ether gradient @ 30 mL/min). Compound 4-[6-amino-1-[(3-methyl-4-nitro-phenyl)methyl]pyrazolo[3,4-d]pyrimidine-4-yl]pyridine-2-carbonitrile (500 mg, 82.49% yield) was obtained as a yellow solid. $^1$H NMR (400 MHz, DMSO-d$_6$) δ=8.99 (dd, J=0.7, 5.1 Hz, 1H), 8.56 (s, 1H), 8.43 (dd, J=1.7, 5.1 Hz, 1H), 7.98-7.91 (m, 1H), 7.39-7.31 (m, 1H), 7.30-7.07 (m, 3H), 5.68-5.49 (m, 2H), 2.49-2.47 (m, 3H). MS: m/z=387.1 (M+1, ESI+).

Stage 2: Production of 4-(6-amino-1-(4-amino-3-methylbenzyl)-1H-pyrazolo[3,4-d]pyrimidine-4-yl) picolinonitrile (Compound 230)

To a solution of 4-[6-amino-1-[(3-methyl-4-nitro-phenyl) methyl]pyrazolo[3,4-d]pyrimidine-4-yl]pyridine-2-carbonitrile (400 mg, 1 eq) in ethanol (15 mL) and water (5 mL) were added iron dust (289 mg, 5 eq) and NH$_4$Cl (443 mg, 8 eq). The mixture was stirred at 60° C. for 3 h. The reaction mixture was filtered and concentrated under reduced pressure to give a residue. The residue was purified by prep-HPLC (column: Phenomenex Gemini-NX C18 75*30 mm*3 μm; mobile phase: [water (0.05% ammonia hydroxide v/v)-ACN]; B %: 15%-45%, 11.5 min). Compound 230 or 4-[6-amino-1-[(4-amino-3-methyl-phenyl) methyl]pyrazolo[3,4-d]pyrimidine-4-yl]pyridine-2-carbonitrile (41.4 mg, 7% yield, 95.38% purity) was obtained as a yellow solid. $^1$H NMR (400 MHz, DMSO-d$_6$) δ=8.97 (dd, J=0.6, 5.1 Hz, 1H), 8.60 (d, J=0.9 Hz, 1H), 8.44 (s, 1H), 8.40 (dd, J=1.7, 5.1 Hz, 1H), 7.17 (s, 2H), 6.93-6.79 (m, 2H), 6.52 (d, J=8.1 Hz, 1H), 5.24 (s, 2H), 4.81 (s, 2H), 1.99 (s, 3H).

Example 1.16: Production of 6-(6-amino-1-(4-aminobenzyl)-1H-pyrazolo[3,4-d]pyrimidine-4-yl)picolinonitrile (Compound 215)

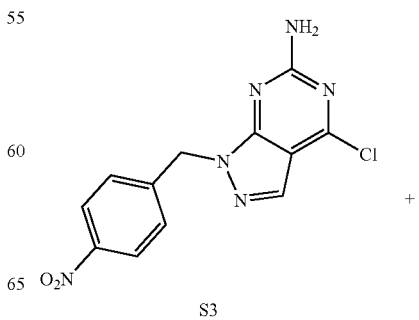

S3

J=1.3, 8.0 Hz, 1H), 8.50 (s, 1H), 8.35-8.30 (m, 1H), 8.28-8.24 (m, 1H), 8.20 (d, J=8.9 Hz, 2H), 7.41 (d, J=8.9 Hz, 2H), 7.20 (s, 2H), 5.64 (s, 2H). MS: m/z=373.1 (M+1, ESI+).

Stage 3: Production of 6-(6-amino-1-(4-aminobenzyl)-1H-pyrazolo[3,4-d]pyrimidine-4-yl)picolinonitrile (Compound 215)

To a solution of 6-[6-amino-1-[(4-nitrophenyl)methyl]pyrazolo[3,4-d]pyrimidine-4-yl]pyridine-2-carbonitrile (200 mg, 1 eq) in water (5 mL) and ethanol (15 mL) was added iron dust (150 mg, 5 eq) and NH₄Cl (230 mg, 8 eq). The mixture was stirred at 60° C. for 3 hr. The reaction mixture was concentrated under reduced pressure to remove ethanol and water to give a residue. The residue was purified by prep-HPLC (column: Phenomenex Gemini-NX C18 75*30 mm*3 μm; mobile phase: [water (0.05% ammonia hydroxide v/v)-ACN]; B %: 10%-40%, 11.5 min), the 89% purity desired compound was obtained, the residue was re-purified by prep-HPLC (column: Welch Ultimate XB-CN 250*50*10 μm; mobile phase: [Hexane-EtOH (0.1% NH₃·H₂O)]; B %: 20%-60%, 15 min), the 91% purity desired compound was obtained. Then the residue was purified by prep-HPLC (column: Phenomenex Luna C18 150*25 mm*10 μm; mobile phase: [water (0.225% FA)-ACN]; B %: 16%-46%, 10 min). Compound 215 or 6-[6-amino-1-[(4-aminophenyl)methyl]pyrazolo[3,4-d]pyrimidine-4-yl]pyridine-2-carbonitrile (21.55 mg, 11% yield, 98.25% purity) was obtained as a yellow solid. ¹H NMR (400 MHz, DMSO-d₆) δ=8.65 (d, J=7.6 Hz, 1H), 8.39 (s, 1H), 8.35-8.27 (m, 1H), 8.26-8.22 (m, 1H), 7.12 (s, 2H), 6.94 (br d, J=8.3 Hz, 2H), 6.48 (br d, J=8.3 Hz, 2H), 5.25 (s, 2H), 5.03 (s, 2H).

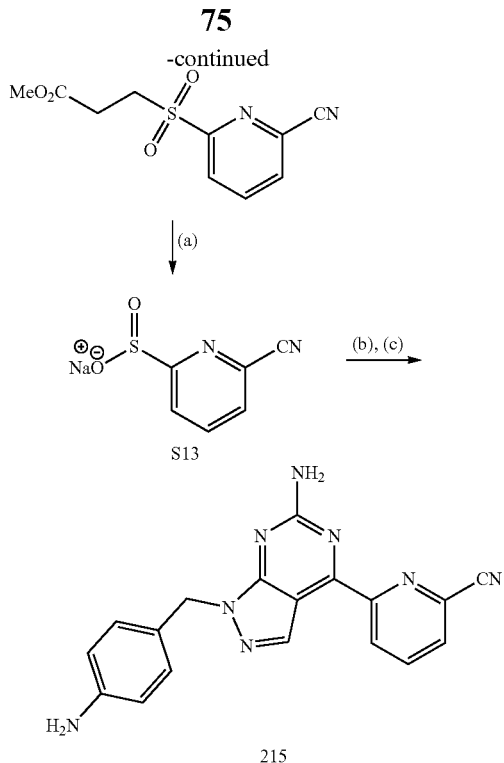

Reagents and condition: (a) NaOMe, MeOH, 25° C., 0.5 h; (b) Pd(OAc)₂, K₂CO₃, Cy₃P, dioxane, 120° C., 16h; (c) Fe, NH₄Cl, EtOH/H₂O, 60° C., 3h.

Stage 1: Production of (6-cyano-2-pyridyl)sulfinyloxy sodium (intermediate compound S13)

To a solution of sodium methoxide (212 mg, 1 eq) in methanol (10 mL) was added methyl 3-[(6-cyano-2-pyridyl)sulfonyl]propanoate (1 g, 1 eq). The mixture was stirred at 25° C. for 0.5 hr. The reaction mixture was concentrated under reduced pressure to remove methanol to give a residue. The crude product of intermediate compound S13 or (6-cyano-2-pyridyl)sulfinyloxy sodium (1 g, crude) was obtained as a yellow solid and used into the next step without further purification. MS: m/z=167.0 (M+1, ESI+).

Stage 2: Production of 6-[6-amino-1-[(4-nitrophenyl)methyl]pyrazolo[3,4-d]pyrimidine-4-yl]pyridine-2-carbonitrile A mixture of intermediate compound S13 or 4-chloro-1-[(4-nitrophenyl) methyl]pyrazolo[3,4-d]pyrimidine-6-amine (500 mg, 1 eq), (6-cyano-2-pyridyl)sulfinyloxy sodium (374 mg, 1.2 eq), palladium acetate (36 mg, 0.1 eq), Cy₃P (92 mg, 32 0.2 eq) and K₂CO₃ (453 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 12 g SEPAFLASH® Silica Flash Column, Eluent of 70~100% Ethyl acetate/Petroleum ether gradient @ 35 mL/min). Compound 6-[6-amino-1-[(4-nitrophenyl)methyl]pyrazolo[3,4-d]pyrimidine-4-yl]pyridine-2-carbonitrile (200 mg, 504.92 μmol, 31% yield, 94% purity) was obtained as a white solid. ¹H NMR (400 MHz, DMSO-d₆) δ=8.66 (dd, Example 1.17: Production of 6-[6-amino-1-[(4-amino-2-fluoro-phenyl)methyl]pyrazolo[3,4-d]pyrimidine-4-yl]pyridine-2-carbonitrile (Compound 219)

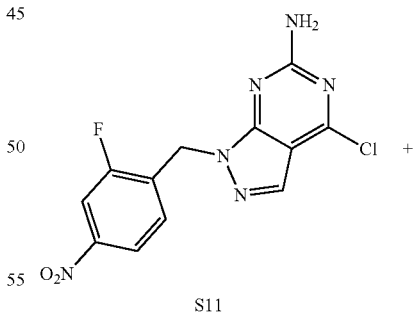

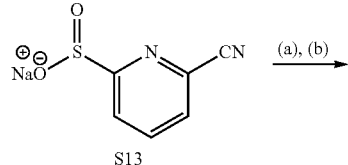

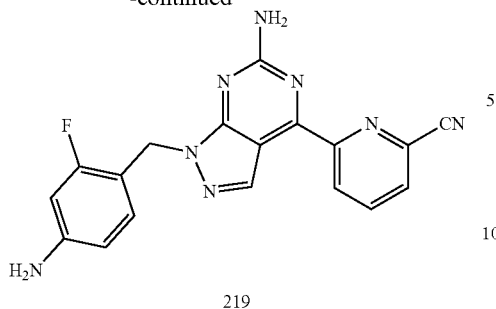

219

Reagents and condition: (a) Pd(OAc)$_2$, K$_2$CO$_3$, Cy$_3$P, dioxane, 120° C., 16h; (c) Fe, NH$_4$Cl, THF/H$_2$O, 80° C., 4h.

Stage 1: Production of 6-[6-amino-1-[(2-fluoro-4-nitro-phenyl)methyl]pyrazolo[3,4-d]pyrimidine-4-yl]pyridine-2-carbonitrile A mixture of intermediate compound S13 or (6-cyano-2-pyridyl)sulfinyloxy sodium (495.01 mg, 2.60 mmol, 1.2 eq), intermediate compound S11 or 4-chloro-1-[(2-fluoro-4-nitro-phenyl)methyl]pyrazolo[3,4-d]pyrimidine-6-amine (700 mg, 2.17 mmol, 1 eq), palladium acetate (48.70 mg, 216.93 μmol, 0.1 eq), Cy$_3$P (121.67 mg, 433.86 μmol, 140.66 μL, 0.2 eq) and K$_2$CO$_3$ (599.64 mg, 4.34 mmol, 2 eq) in dioxane (5 mL) was degassed and purged with nitrogen for three times, and then the mixture was stirred at 120° C. for 16 hr under nitrogen atmosphere. The mixture was concentrated in vacuum to give a residue. The residue was purified by flash silica gel chromatography (12 g SEPAFLASH® Silica Flash Column, Eluent of 10~50% Ethyl acetate/Petroleum ether gradient @ 40 mL/min). Compound 6-[6-amino-1-[(2-fluoro-4-nitro-phenyl)methyl]pyrazolo[3,4-d]pyrimidine-4-yl]pyridine-2-carbonitrile (220 mg, 503.88 μmol, 26% yield, 89.4% purity) was obtained as a yellow solid. $^1$H NMR (400 MHz, DMSO-d$_6$) δ=8.66 (dd, J=1.1, 7.9 Hz, 1H), 8.49 (s, 1H), 8.36-8.29 (m, 1H), 8.28-8.23 (m, 1H), 8.16 (dd, J=2.3, 9.8 Hz, 1H), 8.04 (dd, J=1.8, 8.6 Hz, 1H), 7.29 (t, J=8.0 Hz, 1H), 7.22 (s, 2H), 5.64 (s, 2H).

Stage 2: Production of 6-[6-amino-1-[(4-amino-2-fluorophenyl)methyl]pyrazolo[3,4-d]pyrimidine-4-yl]pyridine-2-carbonitrile (Compound 219)

To the mixture of 6-[6-amino-1-[(2-fluoro-4-nitro-phenyl)methyl]pyrazolo[3,4-d]pyrimidine-4-yl]pyridine-2-carbonitrile (200 mg, 512.39 μmol, 1 eq) in THF (10 mL) and water (2 mL) was added iron dust (143 mg, 2.56 mmol, 5 eq) and NH$_4$Cl (219.27 mg, 4.10 mmol, 8 eq). Then the mixture was stirred at 80° C. for 4 h. The reaction mixture was filtered and the filtrate was added 50 mL saturated NaHCO$_3$ aqueous solution and extracted with ethyl acetate (50 mL×3). Combined the organic layers to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% NH$_3$·H$_2$O)]; B %: 35%-75%, 15 min). Compound 219 or 6-[6-amino-1-[(4-amino-2-fluoro-phenyl)methyl]pyrazolo[3,4-d]pyrimidine-4-yl]pyridine-2-carbonitrile (56.69 mg, 151.63 μmol, 30% yield, 96.38% purity) was obtained as a yellow solid. $^1$H NMR (400 MHz, DMSO-d$_6$) δ=8.65 (dd, J=1.2, 8.0 Hz, 1H), 8.39 (s, 1H), 8.34-8.29 (m, 1H), 8.26-8.22 (m, 1H), 7.13 (s, 2H), 6.95-6.79 (m, 1H), 6.31 (dd, J=1.8, 5.4 Hz, 1H), 6.28 (s, 1H), 5.40 (s, 2H), 5.29 (s, 2H).

Example 1.18: Production of 6-[6-amino-1-[(4-amino-2,6-difluoro-phenyl)methyl]pyrazolo[3,4-d]pyrimidine-4-yl]pyridine-2-carbonitrile (Compound 223)

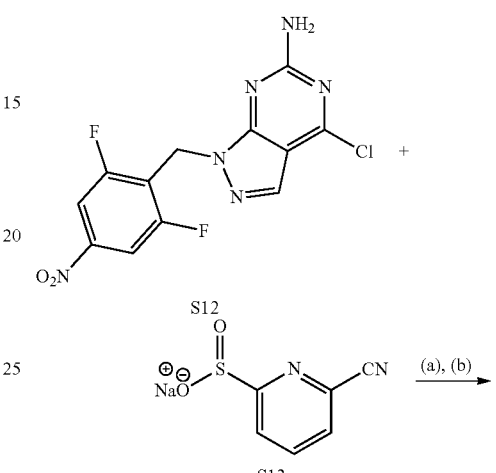

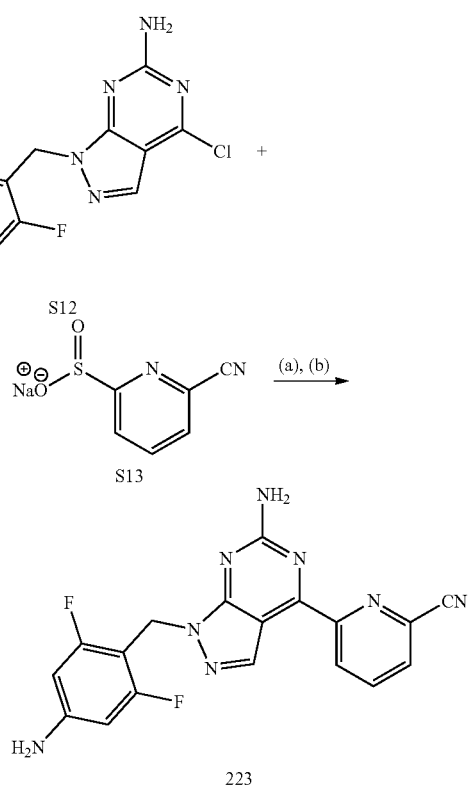

223

Reagents and condition: (a) Pd(OAc)$_2$, K$_2$CO$_3$, Cy$_3$P, dioxane, 120° C., 16h; (c) Fe, NH$_4$Cl, THF/H$_2$O, 80° C., 5 h.

Stage 1: Production of 6-[6-amino-1-[(2,6-difluoro-4-nitro-phenyl)methyl]pyrazolo[3,4-d]pyrimidine-4-yl]pyridine-2-carbonitrile A mixture of intermediate compound S13 or sodium 6-cyanopyridine-2-sulfinate (530 mg, 2.79 mmol, 2 eq), intermediate compound S12 or 4-chloro-1-[(2,6-difluoro-4-nitro-phenyl)methyl]pyrazolo[3,4-d]pyrimidine-6-amine (470 mg, 1.38 mmol, 0.99 eq), palladium acetate (31 mg, 139.36 μmol, 0.1 eq), Cy$_3$P (78 mg, 278.72 μmol, 0.2 eq) and K$_2$CO$_3$ (385 mg, 2.79 mmol, 2 eq) in dioxane (15 mL) was degassed and purged with nitrogen for three times, and then the mixture was stirred at 120° C. for 16 hr under nitrogen atmosphere. The mixture was concentrated in vacuum to give a residue. The residue was purified by flash silica gel chromatography (20 g SEPAFLASH® Silica Flash Column, Eluent of 30~60% Ethyl acetate/Petroleum ether gradient @ 50 mL/min). Compound 6-[6-amino-1-[(2,6-difluoro-4-nitro-phenyl)methyl]pyrazolo[3,4-d]pyrimidine-4-yl]pyridine-2-carbonitrile (180 mg, 290.95 μmol, 21% yield, 66% purity) was obtained as a yellow solid. $^1$H NMR (400 MHz, DMSO-$d_6$) δ=8.65 (dd, J=1.1, 8.0 Hz, 1H), 8.38 (s, 1H), 8.35-8.33 (m, 1H), 8.26-8.21 (m, 1H), 8.12-8.06 (m, 2H), 7.22 (s, 2H), 5.57 (s, 2H). MS: m/z=409.0 (M+1, ESI+).

Stage 2: Production of 6-[6-amino-1-[(4-amino-2,6-difluoro-phenyl)methyl]pyrazolo[3,4-d]pyrimidine-4-yl]pyridine-2-carbonitrile (Compound 223)

To the mixture of 6-[6-amino-1-[(2,6-difluoro-4-nitro-phenyl)methyl]pyrazolo[3,4-d]pyrimidine-4-yl]pyridine-2-carbonitrile (180 mg, 290.95 μmol, 66% purity, 1 eq) in THF (10 mL) and water (3 mL) was added iron dust (81 mg, 1.45 mmol, 5 eq) and NH$_4$Cl (124 mg, 2.33 mmol, 8 eq). Then the mixture was stirred at 80° C. for 5 hr. The reaction mixture was filtered and the filtrate was added saturated NaHCO$_3$ aqueous solution (50 mL) and extracted with ethyl acetate (80 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-EtOH (0.1% ammonia hydroxide)]; B %: 40%-80%, 10 min). Compound 223 or 6-[6-amino-1-[(4-amino-2,6-difluoro-phenyl)methyl]pyrazolo[3,4-d]pyrimidine-4-yl]pyridine-2-carbonitrile (24.24 mg, 60.94 μmol, 21% yield, 95.11% purity) was obtained as a yellow solid. $^1$H NMR (400 MHz, DMSO-$d_6$) δ=8.65 (dd, J=0.9, 8.0 Hz, 1H), 8.35 (s, 1H), 8.34-8.29 (m, 1H), 8.27-8.21 (m, 1H), 7.13 (s, 2H), 6.18 (d, J=10.3 Hz, 2H), 5.80 (s, 2H), 5.27 (s, 2H).

Example 1.19: Production of 6-(6-amino-1-(2,6-difluorobenzyl)-1H-pyrazolo[3,4-d]pyrimidine-4-yl)picolinonitrile (Compound 231)

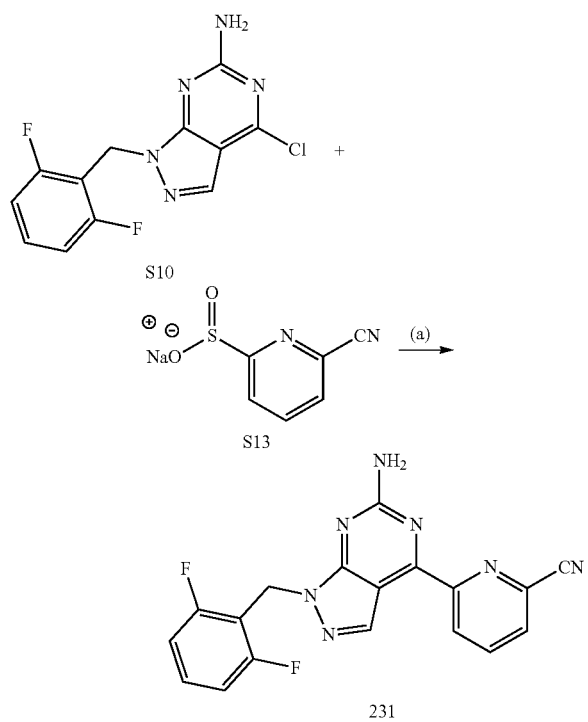

Reagents and condition: (a) Pd(OAc)$_2$, K$_2$CO$_3$, Cy$_3$P, dioxane, 120° C., 10h, MW.

A mixture of (6-cyano-2-pyridyl)sulfinyloxysodium (231 mg, 1.2 eq), intermediate compound S10 or 4-chloro-1-[(2,6-difluorophenyl) methyl]pyrazolo[3,4-d]pyrimidine-6-amine (300 mg, 1 eq), palladium acetate (23 mg, 0.1 eq), Cy$_3$P (57 mg, 0.2 eq) and K$_2$CO$_3$ (280 mg, 2 eq) in dioxane (2 mL) was degassed and purged with nitrogen for three times, and then the mixture was stirred at 120° C. for 10 hr under microwave condition. The reaction mixture was filtered and concentrated under reduced pressure to give a residue. The residue was purified by prep-HPLC (column: Phenomenex Luna C18 150*25 mm*10 μm; mobile phase: [water (0.225% FA)-ACN]; B %: 37%-67%, 11 min). Compound 231 or 6-[6-amino-1-[(2,6-difluorophenyl)methyl]pyrazolo[3,4-d]pyrimidine-4-yl]pyridine-2-carbonitrile (70.52 mg, 18% yield, 95.65% purity) was obtained as a yellow solid. $^1$H NMR (400 MHz, DMSO-$d_6$) δ=8.65 (dd, J=1.0, 8.0 Hz, 1H), 8.36 (s, 1H), 8.33-8.27 (m, 1H), 8.26-8.20 (m, 1H), 7.51-7.41 (m, 1H), 7.18 (s, 2H), 7.12 (t, J=8.0 Hz, 2H), 5.48 (s, 2H).

Example 1.20: Production of 6-(6-amino-1-(4-amino-3-methylbenzyl)-1H-pyrazolo[3,4-d]pyrimidine-4-yl)picolinonitrile (Compound 227)

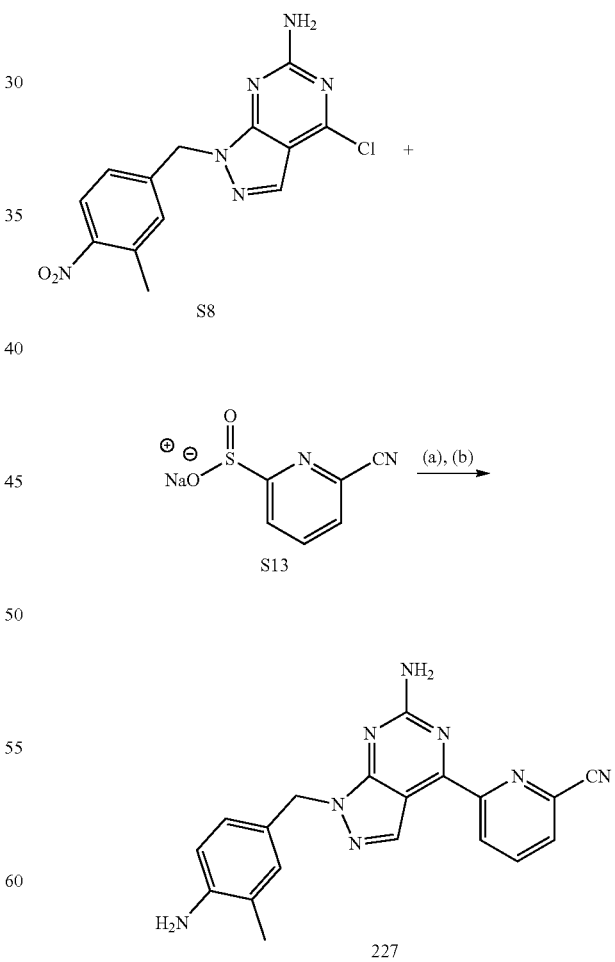

Reagents and condition: (a) Pd(OAc)$_2$, K$_2$CO$_3$, Cy$_3$P, dioxane, 120° C., 16 h; (b) Fe, NH$_4$Cl, EtOH/H$_2$O, 60° C., 2 h.

Stage 1: Production of 6-[6-amino-1-[(3-methyl-4-nitro-phenyl)methyl]pyrazolo[3,4-d]pyrimidine-4-yl]pyridine-2-carbonitrile A mixture of intermediate compound S13 or (6-cyano-2-pyridyl)sulfinyloxy sodium (356 mg, 1.2 eq), intermediate compound S8 or 4-chloro-1-[(3-methyl-4-nitro-phenyl)methyl]pyrazolo[3,4-d]pyrimidine-6-amine (500 mg, 1 eq), palladium acetate (35 mg, 0.1 eq), Cy$_3$P (88 mg, 0.2 eq) and K$_2$CO$_3$ (433 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 24 g SEPA-FLASH® Silica Flash Column, Eluent of 5080% Ethyl acetate/Petroleum ether gradient @ 35 mL/min). Compound 6-[6-amino-1-[(3-methyl-4-nitro-phenyl)methyl]pyrazolo[3,4-d]pyrimidine-4-yl]pyridine-2-carbonitrile (300 mg, 40% yield, 81% purity) was obtained as a yellow solid. $^1$H NMR (400 MHz, DMSO-d$_6$) δ=8.66 (dd, J=1.1, 7.9 Hz, 1H), 8.48 (s, 1H), 8.37-8.29 (m, 1H), 8.28-8.22 (m, 1H), 7.95 (d, J=8.5 Hz, 1H), 7.32 (s, 1H), 7.24-7.14 (m, 3H), 5.55 (s, 2H), 2.47 (s, 3H). MS: m/z=387.1 (M+1, ESI+).

Stage 2: Production of 6-(6-amino-1-(4-amino-3-methylbenzyl)-1H-pyrazolo[3,4-d]pyrimidine-4-yl)picolinonitrile (Compound 227)

To a solution of 6-[6-amino-1-[(3-methyl-4-nitro-phenyl)methyl]pyrazolo[3,4-d]pyrimidine-4-yl]pyridine-2-carbonitrile (311 mg, 1 eq) in water (5 mL) and ethanol (15 mL) were added iron dust (225 mg, 5 eq) and NH$_4$Cl (344 mg, 8 eq). The mixture was stirred at 60° C. for 2 hr. The reaction mixture was concentrated under reduced pressure to remove ethanol and water to give a residue. The residue was purified by prep-HPLC (column: Phenomenex Gemini-NX C18 75*30 mm*3 μm; mobile phase: [water (0.05% ammonia hydroxide v/v)-ACN]; B %: 10%-40%, 11.5 min), the 88% purity desired compound was obtained, the residue was re-purified by prep-HPLC (column: Welch Ultimate XB-SiOH 250*50*10 μm; mobile phase: [Hexane-EtOH (0.1% NH$_3$+120)]; B %: 15%-55%, 15 min), the 90% purity desired compound was obtained. Then the residue was purified by prep-HPLC (column: Welch Ultimate XB-SiOH 250*50*10 μm; mobile phase: [Hexane-EtOH (0.1% NH$_3$·H$_2$O)]; B %: 15%-55%, 15 min), 91% purity desired compound was obtained. Finally the residue was purified by prep-HPLC (column: Phenomenex Luna C18 150*25 mm*10 μm; mobile phase: [water (0.225% FA)-ACN]; B %: 21%-51%, 10 min). Compound 227 or 6-[6-amino-1-[(4-amino-3-methyl-phenyl)methyl]pyrazolo[3,4-d]pyrimidine-4-yl]pyridine-2-carbonitrile (30.69 mg, 10% yield, 98.87% purity) was obtained as a yellow solid. $^1$H NMR (400 MHz, DMSO-d$_6$) δ=8.65 (dd, J=1.1, 8.0 Hz, 1H), 8.39 (s, 1H), 8.34-8.27 (m, 1H), 8.26-8.20 (m, 1H), 7.11 (s, 2H), 6.86 (s, 1H), 6.82 (dd, J=1.9, 8.1 Hz, 1H), 6.52 (d, J=8.0 Hz, 1H), 5.24 (s, 2H), 4.80 (s, 2H), 1.99 (s, 3H).

Example 1.21: Production of 2-(6-amino-1-(4-aminobenzyl)-1H-pyrazolo[3,4-d]pyrimidine-4-yl)isonicotinonitrile (Compound 216)

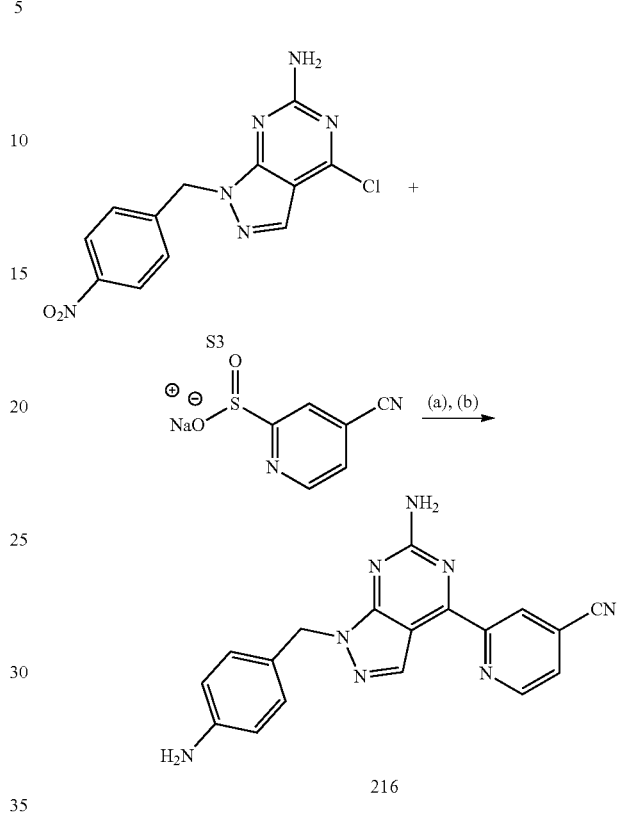

216

Reagents and condition: (a) Pd(OAc)$_2$, K$_2$CO$_3$, Cy$_3$P, dioxane, 120° C., 16 h; (b) Fe, NH$_4$Cl, EtOH/H$_2$O, 60° C., 2h.

Stage 1: Production of 2-(6-amino-1-(4-nitrobenzyl)-1H-pyrazolo[3,4-d]pyrimidine-4-yl)isonicotinonitrile A mixture of sodium 4-cyanopyridine-2-sulfinate (298 mg, 1.2 eq), intermediate compound S3 or 4-chloro-1-[(4-nitrophenyl)methyl]pyrazolo[3,4-d]pyrimidine-6-amine (400 mg, 1 eq), palladium acetate (29 mg, 0.1 eq), Cy$_3$P (73 mg, 0.2 eq) and K$_2$CO$_3$ (362 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 12 g SEPAFLASH® Silica Flash Column, Eluent of 70-90% Ethyl acetate/Petroleum ether gradient @ 30 mL/min). Compound 2-[6-amino-1-[(4-nitrophenyl)methyl]pyrazolo[3,4-d]pyrimidine-4-yl]pyridine-4-carbonitrile (300 mg, 55% yield, 89% purity) was obtained as a yellow solid. MS: m/z=373.1 (M+1, ESI+).

Stage 2: Production of 2-(6-amino-1-(4-aminobenzyl)-1H-pyrazolo[3,4-d]pyrimidine-4-yl)isonicotinonitrile (Compound 216)

To a solution of 2-[6-amino-1-[(4-nitrophenyl)methyl]pyrazolo[3,4-d]pyrimidine-4-yl]pyridine-4-carbonitrile (300 mg, 1 eq) in water (5 mL) and ethanol (15 mL) was added iron dust (225 mg, 5 eq) and NH$_4$Cl (345 mg, 8 eq). The mixture was stirred at 60° C. for 2 hr. The reaction mixture was concentrated under reduced pressure to remove ethanol and water to give a residue. The residue was purified by prep-HPLC (column: Phenomenex Gemini-NX C18 75*30 mm*3 µm; mobile phase: [water (10 mM NH$_4$HCO$_3$)-ACN]; B %: 18%-48%, 8 min), 80% purity desired compound was obtained. Then the residue was purified by the 2nd prep-HPLC (column: Welch Ultimate XB-SiOH 250*50*10 µm; mobile phase: [Hexane-EtOH (0.1% NH$_3$·H$_2$O)]; B %: 15%-55%, 15 min), 80% purity desired compound was obtained.

Finally the residue was purified by the 3rd prep-HPLC (column: Phenomenex Luna C18 150*25 mm*10 µm; mobile phase: [water (0.225% FA)-ACN]; B %: 17%-47%, 10 min). Compound 216 or 2-[6-amino-1-[(4-aminophenyl) methyl]pyrazolo[3,4-d]pyrimidine-4-yl]pyridine-4-carbonitrile (23.18 mg, 8% yield, 95.02% purity) was obtained as a yellow solid. $^1$H NMR (400 MHz, DMSO-d$_6$) δ=9.54 (d, J=2.1 Hz, 1H), 9.22 (d, J=2.0 Hz, 1H), 8.92 (t, J=2.1 Hz, 1H), 8.45 (s, 1H), 7.13 (s, 2H), 6.96 (d, J=8.4 Hz, 2H), 6.63-6.37 (m, 2H), 5.25 (s, 2H), 5.04 (s, 2H). HRMS-TOF: 343.1408.

Example 1.22: Production of 2-(6-amino-1-(4-amino-2-fluorobenzyl)-1H-pyrazolo[3,4-d]pyrimidine-4-yl)isonicotinonitrile (Compound 220)

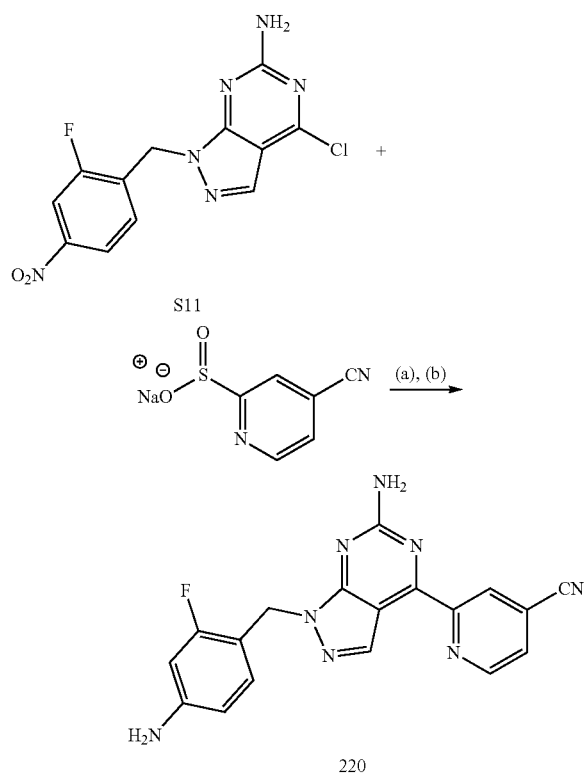

Reagents and condition: (a) Pd(OAc)$_2$, K$_2$CO$_3$, Cy$_3$P, dioxane, 120° C., 16h; (b) Fe, NH$_4$Cl, EtOH/H$_2$O, 60° C., 1 h.

Stage 1: Production of 2-(6-amino-1-(2-fluoro-4-nitrobenzyl)-1H-pyrazolo[3,4-d]pyrimidine-4-yl) isonicotinonitrile A mixture of sodium 4-cyanopyridine-2-sulfinate (424 mg, 1.2 eq), intermediate compound S11 or 4-chloro-1-[(2-fluoro-4-nitro-phenyl)methyl]pyrazolo[3,4-d]pyrimidine-6-amine (600 mg, 1 eq), palladium acetate (41 mg, 0.1 eq), Cy$_3$P (104 mg, 0.2 eq) and K$_2$CO$_3$ (513 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 12 g SEPAFLASH® Silica flash column, eluent of 70-90% ethyl acetate/petroleum ether gradient @ 30 mL/min). Compound 2-[6-amino-1-[(2-fluoro-4-nitro-phenyl)methyl]pyrazolo[3,4-d]pyrimidine-4-yl] pyridine-4-carbonitrile (300 mg, 41% yield, 99% purity) was obtained as a yellow solid. $^1$H NMR (400 MHz, DMSO-d$_6$) δ=9.13-9.06 (m, 1H), 8.68 (dd, J=0.9, 1.5 Hz, 1H), 8.55 (s, 1H), 8.16 (dd, J=2.3, 9.9 Hz, 1H), 8.09 (dd, J=1.6, 4.9 Hz, 1H), 8.03 (dd, J=2.1, 8.5 Hz, 1H), 7.30 (t, J=8.0 Hz, 1H), 7.21 (s, 2H), 5.63 (s, 2H).

Stage 2: Production of 2-(6-amino-1-(4-amino-2-fluorobenzyl)-1H-pyrazolo[3,4-d]pyrimidine-4-yl) isonicotinonitrile (Compound 220)

To a solution of 2-[6-amino-[4(2-fluoro-4-nitro-phenyl) methyl]pyrazolo[3, d]pyrimidine-4-yl]pyridine-4-carbonitrile (300 mg, 1 eq) in water (5 mL) and ethanol (15 mL) was added iron dust (214 mg, 5 eq) and NH$_4$Cl (328 mg, 8 eq). The mixture was stirred at 60° C. for 1 hr. The reaction mixture was concentrated under reduced pressure to remove ethanol and water to give a residue. The residue was purified by prep-HPLC (column: Welch Ultimate XB-CN 250*70*10 µm; mobile phase: [Hexane-EtOH column: Welch Ultimate XB-SiOH 250*50*10 µm; mobile phase: [Hexane-EtOH (0.1% NH$_3$·H$_2$O)]; B %: 15%-55%, 15 min (0.1% NH$_3$·H$_2$O); B %: 30%-70%, 15 min), 90% purity desired compound was obtained after prep-HPLC, the residue was purified by 2$^{nd}$ prep-HPLC (column: Welch Ultimate XB-CN 250*70*10 µm; mobile phase: [Hexane-EtOH (0.1% ammonia hydroxide)]; B %: 30%-70%, 15 min). Compound 220 or 2-[6-amino-[4(4-amino-2-fluoro-phenyl) methyl]pyrazolo[3,4-d]pyrimidine-4-yl]pyridine-4-carbonitrile (33.67 mg, 89.81 µma 96.12% purity) was obtained as a yellow solid. $^1$H NMR (400 MHz, DMSO-d$_6$) δ=9.08 (dd, J=0.7, 5.0 Hz, 1H), 8.68 (d, J=1.3 Hz, 1H), 8.46 (s, 1H), 8.08 (dd, J=1.6, 5.0 Hz, 1H), 7.13 (s, 2H), 6.88 (t, J=8.4 Hz, 1H), 6.33-6.30 (m, 1H), 6.29 (s, 1H), 5.40 (s, 2H), 5.29 (s, 2H).

Example 1.23: Production of 2-[6-amino-1-[(4-amino-2,6-difluoro-phenyl)methyl]pyrazolo[3,4-d]pyrimidine-4-yl]pyridine-4-carbonitrile (Compound 224)

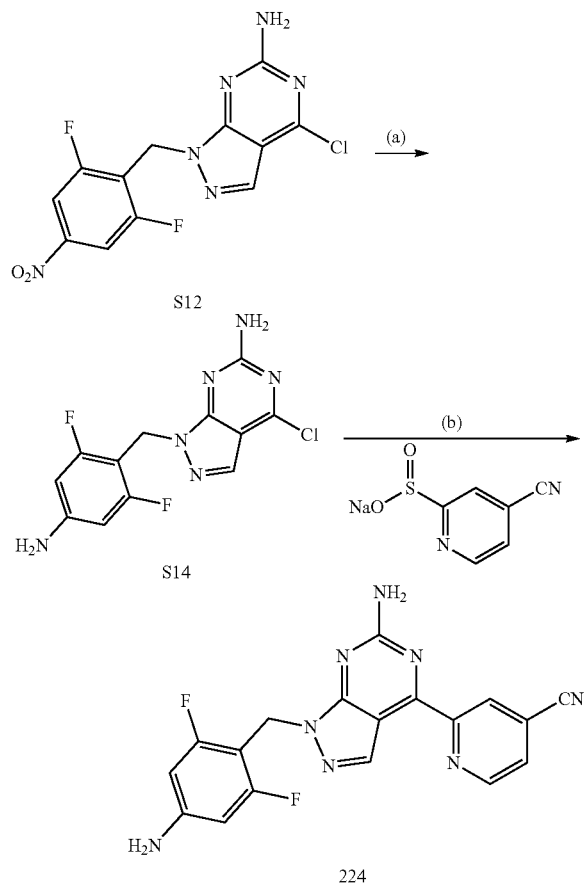

Reagents and condition: (a) Fe, NH$_4$Cl, EtOH/H$_2$O, 80° C., 3h; (b) Pd(OAc)$_2$, K$_2$CO$_3$, PCy$_3$, dioxane, 120° C., 16h.

Stage 1: Production of 1-(4-amino-2,6-difluorobenzyl)-4-chloro-1H-pyrazolo[3,4-d]pyrimidine-6-amine (Intermediate Compound S14)

To the mixture of intermediate compound S12 or 4-chloro-1-[(2,6-difluoro-4-nitro-phenyl)methyl]pyrazolo[3,4-d]pyrimidine-6-amine (700 mg, 1.38 mmol, 67% purity, 1 eq) in water (3 mL) and ethanol (10 mL) were added iron dust (385 mg, 6.88 mmol, 5 eq) and NH$_4$Cl (590 mg, 11.01 mmol, 8 eq). Then the mixture was stirred at 80° C. for 3 h. The reaction mixture was filtered and the filtrate was concentrated in vacuum. The mixture was added water (30 mL) and extracted with ethyl acetate (30 mL×3). Combined the organic layers to dry over anhydrous sodium sulfate, filter and concentrate in vacuum. The residue was purified by prep-HPLC (column: Welch Ultimate XB-CN 250*70*10 μm; mobile phase: [Hexane-EtOH (0.1% NH$_3$·H$_2$O)]; B %: 20%-60%, 15 min). Intermediate compound S14 or 1-(4-amino-2,6-difluorobenzyl)-4-chloro-1H-pyrazolo[3,4-d]pyrimidine-6-amine (400 mg, 1.03 mmol, 75% yield, 88% purity) was obtained as a yellow solid. $^1$H NMR (400 MHz, DMSO-d$_6$) δ=7.92 (s, 1H), 7.32 (s, 2H), 6.25-6.09 (m, 2H), 5.80 (s, 2H), 5.18 (s, 2H).

Stage 2: Production of 2-[6-amino-1-[(4-amino-2,6-difluoro-phenyl)methyl]pyrazolo[3,4-d]pyrimidine-4-yl]pyridine-4-carbonitrile (Compound 224)

A mixture of (4-cyano-2-pyridyl)sulfinyloxy sodium (550 mg, 2.89 mmol, 2.55 eq), intermediate compounds S14 or 1-[(4-amino-2,6-difluoro-phenyl)methyl]-4-chloro-pyrazolo[3,4-d]pyrimidine-6-amine (400 mg, 1.13 mmol, 88% purity, 1 eq), palladium acetate (25 mg, 113.30 μmol, 0.1 eq), Cy$_3$P (63 mg, 226.59 μmol, 73.46 μL, 0.2 eq) and K$_2$CO$_3$ (313 mg, 2.27 mmol, 2 eq) in dioxane (10 mL) was degassed and purged with nitrogen for three times, and then the mixture was stirred at 120° C. for 16 hr under nitrogen atmosphere. The reaction mixture was filtered and the filtrate was concentrated in vacuum. The residue was purified by flash silica gel chromatography (20 g SEPAFLASH® Silica Flash Column, Eluent of 20~40% Ethyl acetate/Petroleum ether gradient @ 40 mL/min). Compound 224 or 2-[6-amino-1-[(4-amino-2,6-difluoro-phenyl)methyl]pyrazolo[3,4-d]pyrimidine-4-yl]pyridine-4-carbonitrile (70 mg, 181.87 μmol, 16% yield, 98.30% purity) was obtained as a yellow solid. $^1$H NMR (400 MHz, DMSO-d$_6$) δ=9.07 (dd, J=0.8, 5.0 Hz, 1H), 8.67 (dd, J=0.9, 1.5 Hz, 1H), 8.41 (s, 1H), 8.06 (dd, J=1.7, 5.0 Hz, 1H), 7.11 (s, 2H), 6.27-6.11 (m, 2H), 5.79 (s, 2H), 5.26 (s, 2H).

Example 1.24: Production of 2-(6-amino-1-(2,6-difluorobenzyl)-1H-pyrazolo[3,4-d]pyrimidine-4-yl)isonicotinonitrile (Compound 232)

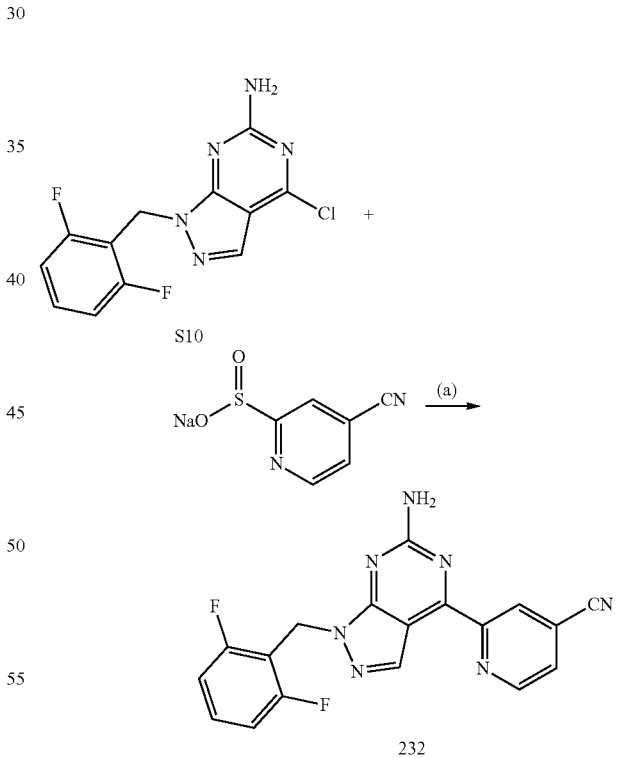

Reagents and condition: (a) Pd(OAc)$_2$, K$_2$CO$_3$, Cy$_3$P, dioxane, 120° C., 16h.

A mixture of (4-cyano-2-pyridyl)sulfinyloxy sodium (232 mg, 1.2 eq), intermediate compound S10 or 4-chloro-1-[(2,6-difluorophenyl)methyl]pyrazolo[3,4-d]pyrimidine-6-amine (300 mg, 1 eq), palladium acetate (23 mg, 0.1 eq), Cy$_3$P (57 mg, 0.2 eq) and K$_2$CO$_3$ (281 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by prep-HPLC (column: Unisil 3-100 C18 Ultra 150*50 mm*3 µm; mobile phase: [water (0.225% FA)-ACN]; B %: 43%-63%, 10 min). Compound 232 or 2-[6-amino-1-[(2,6-difluorophenyl)methyl]pyrazolo[3,4-d]pyrimidine-4-yl]pyridine-4-carbonitrile (66.33 mg, 18% yield, 99.34% purity) was obtained as a white solid. $^1$H NMR (400 MHz, DMSO-d$_6$) δ=9.06 (d, J=5.0 Hz, 1H), 8.67 (s, 1H), 8.44-8.38 (m, 1H), 8.09-8.03 (m, 1H), 7.51-7.39 (m, 1H), 7.22-7.15 (m, 2H), 7.14-7.09 (m, 2H), 5.47 (s, 2H).

Example 1.25: 2-(6-amino-1-(4-amino-3-methylbenzyl)-1H-pyrazolo[3,4-d]pyrimidine-4-yl)isonicotinonitrile (Compound 228)

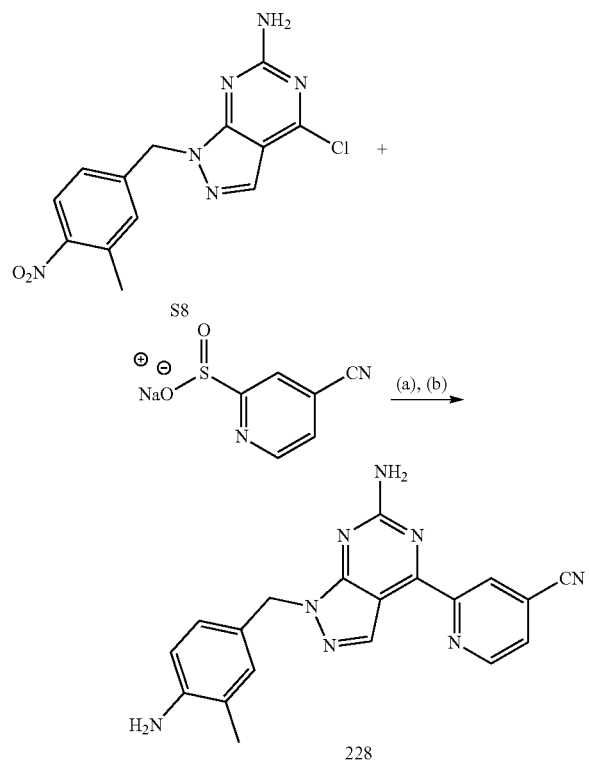

Reagents and condition: (a) Pd(OAc)$_2$, K$_2$CO$_3$, Cy$_3$P, dioxane, 120° C., 16h; (b) Fe, NH$_4$Cl, EtOH/H$_2$O, 60° C., 2h.

Stage 1: Production of 2-(6-amino-1-(3-methyl-4-nitrobenzyl)-1H-pyrazolo[3,4-d]pyrimidine-4-yl)isonicotinonitrile A mixture of (4-cyano-2-pyridyl)sulfinyloxy sodium (215 mg, 1.2 eq), intermediate compound S8 or 4-chloro-1-[(3-methyl-4-nitro-phenyl)methyl]pyrazolo[3,4-d]pyrimidine-6-amine (300 mg, 1 eq), palladium acetate (21 mg, 0.1 eq), Cy$_3$P (52 mg, 0.2 eq) and K$_2$CO$_3$ (260 mg, 2 eq) in dioxane (5 mL) was degassed and purged with nitrogen for three times, and then the mixture was stirred at 120° C. for 16 hr under nitrogen atmosphere. The reaction mixture was filtered and concentrated under reduced pressure to give a residue. The residue was purified by flash silica gel chromatography (ISCO®; 24 g SEPAFLASH® Silica Flash Column, Eluent of 50~80% Ethyl acetate/Petroleum ether gradient @ 35 mL/min). Compound 2-[6-amino-1-[(3-methyl-4-nitro-phenyl)methyl]pyrazolo[3,4-d]pyrimidine-4-yl]pyridine-4-carbonitrile (200 mg, 55% yield) was obtained as a yellow solid. MS: m/z=387.1 (M+1, ESI+).

Stage 2: Production of 2-(6-amino-1-(4-amino-3-methylbenzyl)-1H-pyrazolo[3,4-d]pyrimidine-4-yl)isonicotinonitrile (Compound 228)

To a solution of 2-[6-amino-1-[(3-methyl-4-nitro-phenyl)methyl]pyrazolo[3,4-d]pyrimidine-4-yl]pyridine-4-carbonitrile (200 mg, 1 eq) in ethanol (15 mL) and water (5 mL) was added iron dust (145 mg, 5 eq) and NH$_4$Cl (221 mg, 8 eq). The mixture was stirred at 60° C. for 2 hr. The reaction mixture was filtered and concentrated under reduced pressure to give a residue. The residue was purified by prep-HPLC (column: Phenomenex Gemini-NX C18 75*30 mm*3 µm; mobile phase: [water (10 mM NH$_4$HCO$_3$)-ACN]; B %: 20%-50%, 8 min), 80% purity desired compound was obtained after prep-HPLC, the residue was purified by $2^{nd}$ prep-HPLC (column: Shim-pack C18 150*25*10 µm; mobile phase: [water (0.225% FA)-ACN]; B %: 16%-46%, 10 min). Compound 228 or 2-[6-amino-1-[(4-amino-3-methyl-phenyl)methyl]pyrazolo[3,4-d]pyrimidine-4-yl]pyridine-4-carbonitrile (19.65 mg, 10% yield, 96.15% purity) was obtained as a yellow solid. $^1$H NMR (400 MHz, DMSO-d$_6$) δ=9.08 (dd, J=0.8, 4.9 Hz, 1H), 8.67 (dd, J=0.9, 1.6 Hz, 1H), 8.45 (s, 1H), 8.07 (dd, J=1.6, 5.0 Hz, 1H), 7.10 (s, 2H), 6.86 (s, 1H), 6.82 (dd, J=1.9, 8.1 Hz, 1H), 6.51 (d, J=8.0 Hz, 1H), 5.23 (s, 2H), 4.80 (s, 2H), 1.98 (s, 3H).

Example 1.26: Production of 5-(6-amino-1-(4-aminobenzyl)-1H-pyrazolo[3,4-d]pyrimidine-4-yl)nicotinonitrile (Compound 217)

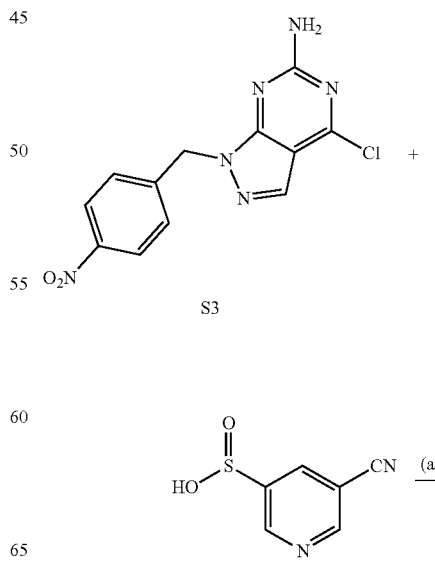

89

-continued

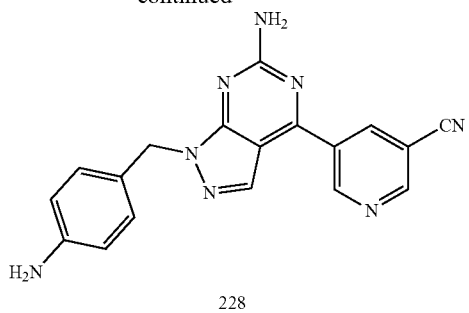

228

Reagents and condition: (a) Pd(dppf)Cl$_2$, K$_2$CO$_3$, dioxane/H$_2$O, 110° C., 16h; (b) Fe, NH$_4$Cl, THF/H$_2$O, 60° C., 3h.

Stage 1: Production of 5-(6-amino-1-(4-nitrobenzyl)-1H-pyrazolo[3,4-d]pyrimidine-4-yl)nicotinonitrile A mixture of (5-cyano-3-pyridyl)boronic acid (583 mg, 1.5 eq), intermediate compound S3 or 4-chloro-1-[(4-nitrophenyl)methyl]pyrazolo[3,4-d]pyrimidine-6-amine (800 mg, 1 eq), K$_2$CO$_3$ (726 mg, 2 eq), Pd(dppf)Cl$_2$ (192 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 24 g SEPAFLASH® Silica Flash Column, Eluent of 0~100% Ethyl acetate/Petroleum ether gradient @ 30 mL/min). Compound 5-[6-amino-1-[(4-nitrophenyl)methyl]pyrazolo[3,4-d]pyrimidine-4-yl]pyridine-3-carbonitrile (800 mg, 82% yield) was obtained as a yellow solid. $^1$H NMR (400 MHz, DMSO-d$_6$) δ=9.63-9.52 (m, 1H), 9.37-9.31 (m, 2H), 9.25-9.23 (m, 1H), 9.15-9.12 (m, 2H), 7.46-7.42 (m, 2H), 5.65-5.60 (m, 2H). MS: m/z=373.1 (M+1, ESI+).

Stage 2: Production of 5-(6-amino-1-(4-aminobenzyl)-1H-pyrazolo[3,4-d]pyrimidine-4-yl)nicotinonitrile (Compound 217)

To a solution of 5-[6-amino-1-[(4-nitrophenyl)methyl]pyrazolo[3,4-d]pyrimidine-4-yl]pyridine-3-carbonitrile (300 mg, 1 eq) in THF (15 mL) and water (5 mL) was added iron dust (224 mg, 5 eq) and NH$_4$Cl (344 mg, 8 eq). The mixture was stirred at 60° C. for 3 hr. The reaction mixture was concentrated under reduced pressure to remove THF and water to give a residue. The residue was purified by prep-HPLC (column: Phenomenex Gemini-NX C18 75*30 mm*3 μm; mobile phase: [water (0.05% ammonia hydroxide v/v)-ACN]; B %: 10%-40%, 11.5 min). Compound 217 or 5-[6-amino-1-[(4-aminophenyl)methyl]pyrazolo[3,4-d]pyrimidine-4-yl]pyridine-3-carbonitrile (27.63 mg, 7% yield, 98.17% purity) was obtained as a yellow solid. $^1$H NMR (400 MHz, DMSO-d$_6$) δ=9.54 (d, J=2.1 Hz, 1H), 9.22 (d, J=2.0 Hz, 1H), 8.92 (t, J=2.1 Hz, 1H), 8.45 (s, 1H), 7.13 (s, 2H), 6.96 (d, J=8.4 Hz, 2H), 6.63-6.37 (m, 2H), 5.25 (s, 2H), 5.04 (s, 2H).

90

Example 1.27: Production of 5-[6-amino-1-[(4-amino-2-fluoro-phenyl)methyl]pyrazolo[3,4-d]pyrimidine-4-yl]pyridine-3-carbonitrile (Compound 221)

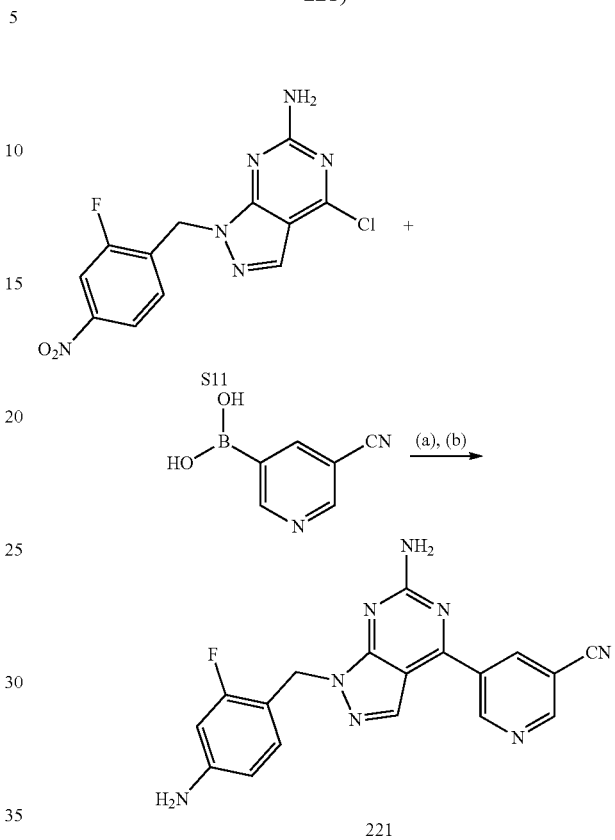

221

Reagents and condition: (a) Pd(dppf)Cl$_2$, K$_2$CO$_3$, dioxane/H$_2$O, 110° C., 16h; (b) Fe, NH$_4$Cl, EtOH/H$_2$O, 60° C., 2h.

Stage 1: Production of 5-(6-amino-1-(2-fluoro-4-nitrobenzyl)-1H-pyrazolo[3,4-d]pyrimidine-4-yl)nicotinonitrile A mixture of (5-cyano-3-pyridyl)boronic acid (343 mg, 1.5 eq), intermediate compound S11 or 4-chloro-1-[(2-fluoro-4-nitro-phenyl)methyl]pyrazolo[3,4-d]pyrimidine-6-amine (500 mg, 1 eq), K$_2$CO$_3$ (428 mg, 2 eq), Pd(dppf)Cl$_2$ (113 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was concentrated under reduced pressure to remove dioxane to give a residue. The residue was purified by flash silica gel chromatography (ISCO®; 12 g SEPAFLASH® Silica Flash Column, Eluent of 0~80% Ethyl acetate/Petroleum ether gradient @ 30 mL/min). Compound 5-[6-amino-1-[(2-fluoro-4-nitro-phenyl)methyl]pyrazolo[3,4-d]pyrimidine-4-yl]pyridine-3-carbonitrile (300 mg, 50% yield) was obtained as a yellow solid. MS: m/z=390.9 (M+1, ESI+).

Stage 2: Production of 5-(6-amino-1-(4-amino-2-fluorobenzyl)-1H-pyrazolo[3,4-d]pyrimidine-4-yl)nicotinonitrile (Compound 221)

To a solution of 5-[6-amino-1-[(2-fluoro-4-nitro-phenyl)methyl]pyrazolo[3,4-d]pyrimidine-4-yl]pyridine-3-carbonitrile (300 mg, 1 eq) in ethanol (15 mL) and water (5 mL) was added iron dust (214 mg, 5 eq) and NH$_4$Cl (328 mg, 8 eq). The mixture was stirred at 60° C. for 2 hr. The reaction mixture was filtered and concentrated under reduced pressure to give a residue. The residue was purified by prep-HPLC (column: Phenomenex Gemini-NX C18 75*30 mm*3 μm; mobile phase: [water (0.05% ammonia hydroxide v/v)-ACN]; B %: 13%-43%, 11.5 min). Compound 221 or 5-[6-amino-1-[(4-amino-2-fluoro-phenyl)methyl]pyrazolo[3,4-d]pyrimidine-4-yl]pyridine-3-carbonitrile (37.61 mg, 13% yield, 94.57% purity) was obtained as a yellow solid. $^1$H NMR (400 MHz, DMSO-d$_6$) δ=9.54 (d, J=2.1 Hz, 1H), 9.23 (d, J=2.0 Hz, 1H), 8.91 (t, J=2.0 Hz, 1H), 8.45 (s, 1H), 7.14 (s, 2H), 6.90 (t, J=8.4 Hz, 1H), 6.31 (d, J=10.8 Hz, 2H), 5.41 (s, 2H), 5.29 (s, 2H).

Example 1.28: Production of 5-[6-amino-1-[(4-amino-2,6-difluoro-phenyl)methyl]pyrazolo[3,4-d]pyrimidine-4-yl]pyridine-3-carbonitrile (Compound 225)

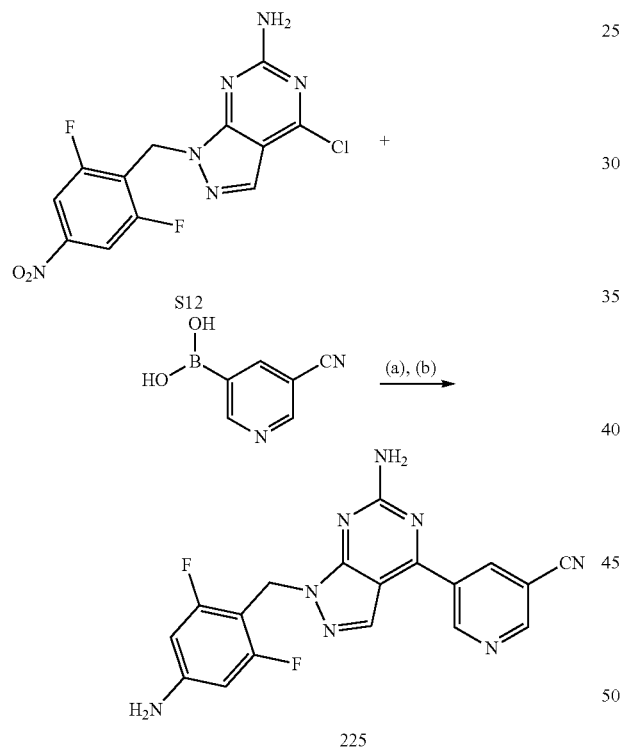

Reagents and conditions: (a) Pd(dppf)Cl$_2$, K$_2$CO$_3$, dioxane/H$_2$O, 100° C., 15h; (b) Fe, NH$_4$Cl, EtOH/H$_2$O, 80° C., 2h.

Stage 1: Production of 5-[6-amino-1-[(2,6-difluoro-4-nitro-phenyl)methyl]pyrazolo[3,4-d]pyrimidine-4-yl]pyridine-3-carbonitrile To the solution of intermediate compound S12 or 4-chloro-1-[(2,6-difluoro-4-nitro-phenyl)methyl]pyrazolo[3,4-d]pyrimidine-6-amine (400 mg, 1.17 mmol, 1 eq) in dioxane (10 mL) and water (2 mL) were added (5-cyano-3-pyridyl)boronic acid (346 mg, 2.34 mmol, 2 eq), Pd(dppf)Cl$_2$ (86 mg, 117.00 μmol, 0.1 eq) and K$_2$CO$_3$ (323 mg, 2.34 mmol, 2 eq). Then the mixture was stirred at 100° C. for 15 h. The mixture was concentrated in vacuum to give a residue. The residue was purified by flash silica gel chromatography (20 g SEPAFLASH® Silica Flash Column, Eluent of 0~60% Ethyl acetate/Petroleum ether gradient @ 50 mL/min). Compound 225 or Compound 5-[6-amino-1-[(2,6-difluoro-4-nitro-phenyl)methyl]pyrazolo[3,4-d]pyrimidine-4-yl]pyridine-3-carbonitrile (400 mg, 852.27 μmol, 73% yield, 87% purity) was obtained as a yellow solid. $^1$H NMR (400 MHz, DMSO-d$_6$) δ=9.51 (d, J=2.0 Hz, 1H), 9.21 (d, J=1.9 Hz, 1H), 8.89 (t, J=2.1 Hz, 1H), 8.44 (s, 1H), 8.09 (d, J=7.3 Hz, 2H), 7.23 (s, 2H), 5.55 (s, 2H). MS: m/z=409.0 (M+1, ESI+).

Stage 2: Production of 5-[6-amino-1-[(4-amino-2,6-difluoro-phenyl) methyl]pyrazolo[3,4-d]pyrimidine-4-yl]pyridine-3-carbonitrile (Compound 225)

To the mixture of 5-[6-amino-1-[(2,6-difluoro-4-nitro-phenyl)methyl]pyrazolo[3,4-d]pyrimidine-4-yl]pyridine-3-carbonitrile (400 mg, 979.62 μmol, 1 eq) in water (3 mL) and ethanol (9 mL) were added iron dust (274 mg, 4.90 mmol, 5 eq) and NH$_4$Cl (420 mg, 7.84 mmol, 8 eq). Then the mixture was stirred at 80° C. for 2 h. The reaction mixture was filtered and the filtrate was concentrated in vacuum. Then the mixture was added water (30 mL) and then extracted with ethyl acetate (30 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase:

[Hexane-EtOH (0.1% NH$_3$·H$_2$O)]; B %: 30%-70%, 15 min) to give a impure product. The impure product was re-purified by prep-HPLC (column: Welch Ultimate XB-CN 250*50*10 μm; mobile phase: [Hexane-EtOH (0.1% NH$_3$·H$_2$O)]; B %: 25%-65%, 15 min). Compound 225 or 5-[6-amino-1-[(4-amino-2,6-difluoro-phenyl)methyl]pyrazolo[3,4-d]pyrimidine-4-yl]pyridine-3-carbonitrile (113.05 mg, 297.07 μmol, 30% yield, 99.42% purity) was obtained as a yellow solid. $^1$H NMR (400 MHz, DMSO-d$_6$) δ=9.52 (d, J=2.1 Hz, 1H), 9.21 (d, J=1.8 Hz, 1H), 8.89 (t, J=2.1 Hz, 1H), 8.38 (s, 1H), 7.13 (s, 2H), 6.18 (d, J=10.1 Hz, 2H), 5.25 (s, 2H).

Example 1.29: Production of 5-(6-amino-1-(2,6-difluorobenzyl)-1H-pyrazolo[3,4-d]pyrimidine-4-yl)nicotinonitrile (Compound 233)

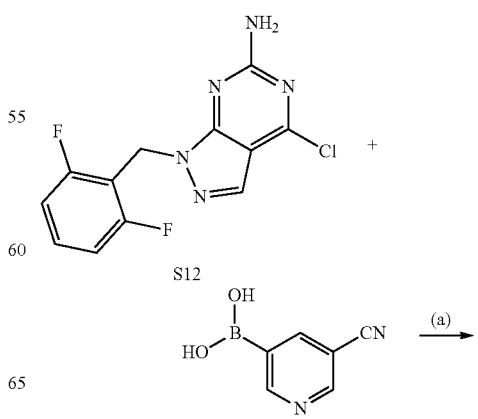

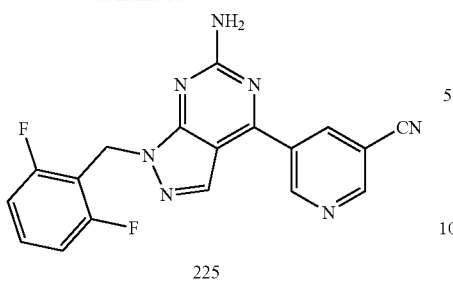

225

Reagents and condition: (a) Pd(dppf)Cl$_2$, K$_2$CO$_3$, dioxane/H$_2$O, 110° C., 16 h.

A mixture of intermediate compound S10 or 4-chloro-1-[(2,6-difluorophenyl)methyl]pyrazolo[3,4-d]pyrimidine-6-amine (400 mg, 1 eq), (5-cyano-3-pyridyl)boronic acid (300 mg, 1.5 eq), K$_2$CO$_3$ (373 mg, 2 eq), Pd(dppf)Cl$_2$ (99 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was concentrated under reduced pressure to remove dioxane to give a residue. The residue was purified by prep-HPLC (column: Unisil 3-100 C18 Ultra 150*50 mm*3 μm; mobile phase: [water (0.225% FA)-ACN]; B %: 45%-65%, 10 min), 80% purity desired compound was obtained, then it was purified by second prep-HPLC (column: Phenomenex Luna C18 150*25 mm*10 μm; mobile phase: [water (0.225% FA)-ACN]; B %: 31%-61%, 10 min). Compound 233 or 5-[(6-amino-1-[(2,6-difluorophenyl)methyl]pyrazolo[3,4-d]pyrimidine-4-yl]pyridine-3-carbonitrile (69.15 mg, 14% yield, 97.76% purity) was obtained as a yellow solid. $^1$H NMR (400 MHz, DMSO-d$_6$) δ=8.96 (d, J=5.1 Hz, 1H), 8.58 (d, J=0.6 Hz, 1H), 8.41-8.39 (m, 1H), 8.39-8.36 (m, 1H), 7.51-7.41 (m, 1H), 7.25 (s, 2H), 7.17-7.08 (m, 2H), 5.47 (s, 2H).

Example 1.30: Production of 5-(6-amino-1-(4-amino-3-methylbenzyl)-1H-pyrazolo[3,4-d]pyrimidine-4-yl)nicotinonitrile (Compound 229)

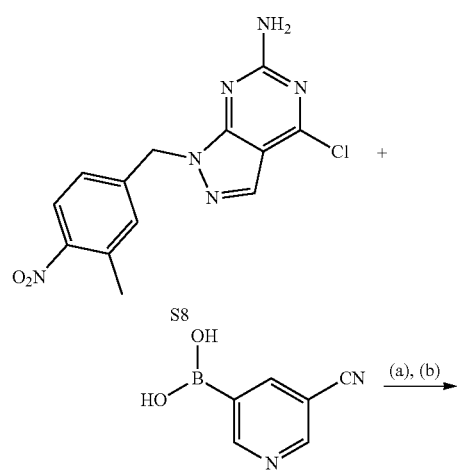

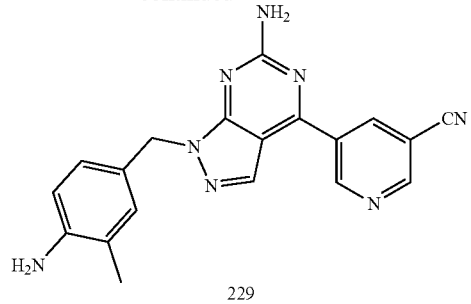

229

Reagents and condition: (a) Pd(dppf)Cl$_2$, K$_2$CO$_3$, dioxane, 110° C., 16h; (b) Fe, NH$_4$Cl, EtOH/H$_2$O, 60° C., 2h.

Stage 1: Production of 5-(6-amino-1-(3-methyl-4-nitrobenzyl)-1H-pyrazolo[3,4-d]pyrimidine-4-yl)nicotinonitrile A mixture of (5-cyano-3-pyridyl)boronic acid (208 mg, 1.5 eq), intermediate compound S8 or 4-chloro-1-[(3-methyl-4-nitro-phenyl)methyl]pyrazolo[3,4-d]pyrimidine-6-amine (300 mg, 1 eq), K$_2$CO$_3$ (260 mg, 2 eq), Pd(dppf)Cl$_2$ (68.87 mg, 0.1 eq) in dioxane (10 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 24 g SEPA-FLASH® Silica Flash Column, Eluent of 0~100% Ethyl acetate/Petroleum ether gradient @ 35 mL/min). Compound 5-[6-amino-1-[(3-methyl-4-nitro-phenyl)methyl]pyrazolo[3,4-d]pyrimidine-4-yl]pyridine-3-carbonitrile (300 mg, 82% yield) was obtained as a yellow solid. MS: m/z=386.9 (M+1, ESI+).

Stage 2: Production of 5-(6-amino-1-(4-amino-3-methylbenzyl)-1H-pyrazolo[3,4-d]pyrimidine-4-yl)nicotinonitrile (Compound 229)

To a solution of 5-[6-amino-1-[(3-methyl-4-nitro-phenyl)methyl]pyrazolo[3,4-d]pyrimidine-4-yl]pyridine-3-carbonitrile (400 mg, 1 eq) in ethanol (15 mL) and water (5 mL) was added iron dust (289 mg, 5 eq) and NH$_4$Cl (443 mg, 8 eq). The mixture was stirred at 60° C. for 2 hr. The reaction mixture was filtered and concentrated under reduced pressure to give a residue. The residue was purified by prep-HPLC (column: Shim-pack C18 150*25*10 μm; mobile phase: [water (0.225% FA)-ACN]; B %: 12%-42%, 10 min), 92% purity desired compound was obtained, then the mixture was purified by 2nd prep-HPLC (column: Phenomenex Gemini-NX C18 75*30 mm*3 μm; mobile phase: [water (0.05% ammonia hydroxide v/v)-ACN]; B %: 14%-44%, 11.5 min). Compound 229 or 5-[6-amino-1-[(4-amino-3-methyl-phenyl)methyl]pyrazolo[3,4-d]pyrimidine-4-yl]pyridine-3-carbonitrile (58.12 mg, 15% yield, 97.57% purity) was obtained as a yellow solid. $^1$H NMR (400 MHz, DMSO-d$_6$) δ=9.53 (d, J=2.1 Hz, 1H), 9.22 (d, J=2.1 Hz, 1H), 8.91 (t, J=2.1 Hz, 1H), 8.43 (s, 1H), 7.12 (s, 2H), 6.91-6.77 (m, 2H), 6.52 (d, J=8.1 Hz, 1H), 5.23 (s, 2H), 4.80 (s, 2H), 1.99 (s, 3H).

Example 1.31: Production of 4-(6-amino-1-(4-aminobenzyl)-1H-pyrazolo[3,4-d]pyrimidine-4-yl)picolinonitrile (Compound 218)

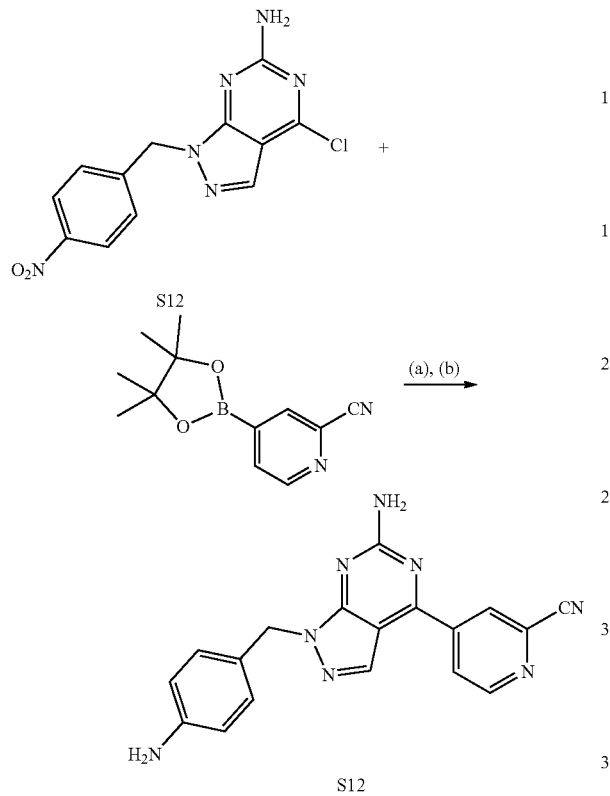

Reagents and condition: (a) Pd(dppf)Cl$_2$, K$_2$CO$_3$, dioxane/H$_2$O, 110° C., 16h; (b) Fe, NH$_4$Cl, EtOH/H$_2$O, 60° C., 2h.

Stage 1: Production of 4-(6-amino-1-(4-nitrobenzyl)-1H-pyrazolo[3,4-d]pyrimidine-4-yl)picolinonitrile A mixture of intermediate compound S3 or 4-chloro-[4 (4-nitrophenyl)methyl]pyrazolo[3,4-d]pyrimidine-6-amine (800 mg, 1 eq), 4-(4,4,5,5-tetramethyl-1,3,2-dioxaborolan-2-yl)pyridine-2-carbonitrile (906 mg, 1.5 eq), K$_2$CO$_3$ (725 mg, 2 eq), Pd(dppf)Cl$_2$ (192 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was filtered and concentrated under reduced pressure to give a residue. The residue was purified by flash silica gel chromatography (ISCO®; 12 g SEPAFLASH® Silica Flash Column, Eluent of 30~80% Ethyl acetate/Petroleum ether gradient @ 35 mL/min). Compound 4-[6-amino-1-[(4-nitrophenyl)methyl]pyrazolo[3,4-d]pyrimidine-4-yl]pyridine-2-carbonitrile (500 mg, 51% yield) was obtained as a yellow solid.

$^1$H NMR (400 MHz, DMSO-d$_6$) δ=9.05-8.94 (m, 1H), 8.84-8.71 (m, 2H), 8.58 (s, 1H), 8.43 (dd, J=1.8, 5.1 Hz, 1H), 8.09-8.07 (m, 1H), 7.46-7.41 (m, 2H), 7.31-7.24 (m, 2H), 5.67-5.61 (m, 2H). MS: m/z=372.9 (M+1, ESI+).

Stage 2: Production of 4-(6-amino-1-(4-aminobenzyl)-1H-pyrazolo[3,4-d]pyrimidine-4-yl)picolinonitrile (Compound 218)

To a solution of 4-[6-amino-1-[(4-nitrophenyl)methyl]pyrazolo[3,4-d]pyrimidine-4-yl]pyridine-2-carbonitrile (300 mg, 1 eq) in water (5 mL) and ethanol (15 mL) was added iron dust (224 mg, 5 eq) and NH$_4$Cl (344 mg, 8 eq). The mixture was stirred at 60° C. for 2 hr. After that, the reaction mixture was concentrated under reduced pressure to remove ethanol and water to give a residue. The residue was purified by prep-HPLC (column: Phenomenex Gemini-NX C18 75*30 mm*3 μm; mobile phase: [water (0.05% ammonia hydroxide v/v)-ACN]; B %: 12%-42%, 11.5 min), 80% purity desired compound was obtained, then the residue was purified by the 2$^{nd}$ prep-HPLC (column: Phenomenex Gemini-NX C18 75*30 mm*3 μm; mobile phase: [water (10 mM NH$_4$HCO$_3$)-ACN]; B %: 16%-46%, 8 min). Compound 218 or 4-[6-amino-1-[(4-aminophenyl)methyl]pyrazolo[3,4-d]pyrimidine-4-yl]pyridine-2-carbonitrile (52.04 mg, 18% yield, 95.28% purity) was obtained as a white solid. $^1$H NMR (400 MHz, DMSO-d$_6$) δ=8.97 (d, J=5.1 Hz, 1H), 8.60 (d, J=0.7 Hz, 1H), 8.44 (s, 1H), 8.40 (dd, J=1.6, 5.1 Hz, 1H), 7.18 (s, 2H), 6.96 (d, J=8.3 Hz, 2H), 6.48 (d, J=8.4 Hz, 2H), 5.25 (s, 2H), 5.04 (s, 2H).

Example 1.32: Production of 4-(6-amino-1-(4-amino-2-fluorobenzyl)-1H-pyrazolo[3,4-d]pyrimidine-4-yl)picolinonitrile (Compound 222)

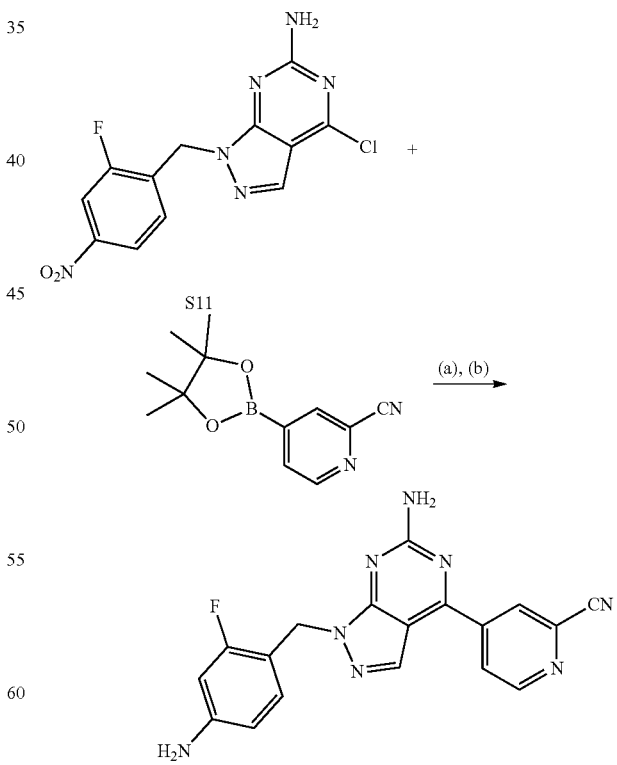

Reagents and condition: (a) Pd(dppf)Cl$_2$, K$_2$CO$_3$, dioxane/H$_2$O, 110° C., 16h; (b) Fe, NH$_4$Cl, EtOH/H$_2$O, 60° C., 2h.

Stage 1: Production of 4-(6-amino-1-(2-fluoro-4-nitrobenzyl)-1H-pyrazolo[3,4-d]pyrimidine-4-yl)picolinonitrile A mixture of intermediate compound S11 or 4-chloro-1-[(2-fluoro-4-nitro-phenyl)methyl]pyrazolo[3,4-d]pyrimidine-6-amine (1 g, 1 eq), 4-(4,4,5,5-tetramethyl-1,3,2-dioxaborolan-2-yl)pyridine-2-carbonitrile (784 mg, 1.1 eq), K$_2$CO$_3$ (856 mg, 2 eq), Pd(dppf)Cl$_2$ (226 mg, 0.1 eq) in dioxane (10 mL) and water (2 mL) was degassed and purged with nitrogen for three times, and then the mixture was stirred at 110° C. for 16 hr under nitrogen atmosphere. The reaction mixture was concentrated under reduced pressure to remove dioxane to give a residue. The residue was purified by flash silica gel chromatography (ISCO®; 12 g SEPAFLASH® Silica Flash Column, Eluent of 0~80% Ethyl acetate/Petroleum ether gradient @ 35 mL/min). Compound 4-[6-amino-1-[(2-fluoro-4-nitro-phenyl) methyl]pyrazolo[3,4-d]pyrimidine-4-yl]pyridine-2-carbonitrile (1 g, 83% yield) was obtained as a yellow solid. $^1$H NMR (400 MHz, DMSO-d$_6$) δ=8.98 (dd, J=0.7, 5.1 Hz, 1H), 8.65-8.59 (m, 2H), 8.56 (s, 1H), 8.41 (dd, J=1.7, 5.1 Hz, 1H), 7.61-7.54 (m, 1H), 7.34 (t, J=8.0 Hz, 1H), 7.31-7.23 (m, 2H), 5.63 (s, 2H). MS: m/z=391.1 (M+1, ESI+).

Stage 2: Production of 4-(6-amino-1-(4-amino-2-fluorobenzyl)-1H-pyrazolo[3,4-d]pyrimidine-4-yl)picolinonitrile (Compound 222)

To a solution of 4-[6-amino-1-[(2-fluoro-4-nitro-phenyl)methyl]pyrazolo[3,4-d]pyrimidine-4-yl]pyridine-2-carbonitrile (500 mg, 1 eq) in ethanol (15 mL) and water (5 mL) was added iron dust (357 mg, 5 eq) and NH$_4$Cl (548 mg, 8 eq). The mixture was stirred at 60° C. for 2 hr. The reaction mixture was filtered and concentrated under reduced pressure to give a residue. The residue was purified by prep-HPLC (column: Phenomenex Gemini-NX C18 75*30 mm*3 µm; mobile phase: [water (0.05% ammonia hydroxide v/v)-ACN]; B %: 15%-45%, 11.5 min), 79% purity desired compound obtained, the residue was purified by the 2nd prep-HPLC (column: Phenomenex Gemini-NX C18 75*30 mm*3 µm; mobile phase: [water (10 mM NH$_4$HCO$_3$)-ACN]; B %: 18%-48%, 8 min), 81% purity desired compound obtained. Finally the residue was purified by the 3rd prep-HPLC (column: Phenomenex Gemini-NX C18 75*30 mm*3 µm; mobile phase: [water (0.05% ammonia hydroxide v/v)-ACN]; B %: 16%-46%, 11.5 min). Compound 222 or 4-[6-amino-1-[(4-amino-2-fluoro-phenyl)methyl]pyrazolo[3,4-d]pyrimidine-4-yl]pyridine-2-carbonitrile (31.41 mg, 95.76% purity) was obtained as a yellow solid. $^1$H NMR (400 MHz, DMSO-d$_6$) δ=8.97 (dd, J=0.8, 5.1 Hz, 1H), 8.60 (dd, J=0.8, 1.7 Hz, 1H), 8.44 (s, 1H), 8.40 (dd, J=1.8, 5.1 Hz, 1H), 7.19 (s, 2H), 6.89 (t, J=8.4 Hz, 1H), 6.37-6.24 (m, 2H), 5.46-5.37 (m, 2H), 5.32-5.22 (m, 2H).

Example 1.33: Production of 2-[6-amino-1-[[4-amino-3-(trifluoromethyl)phenyl]methyl]pyrazolo[3,4-d]pyrimidine-4-yl]pyridine-4-carbonitrile (Compound 235)

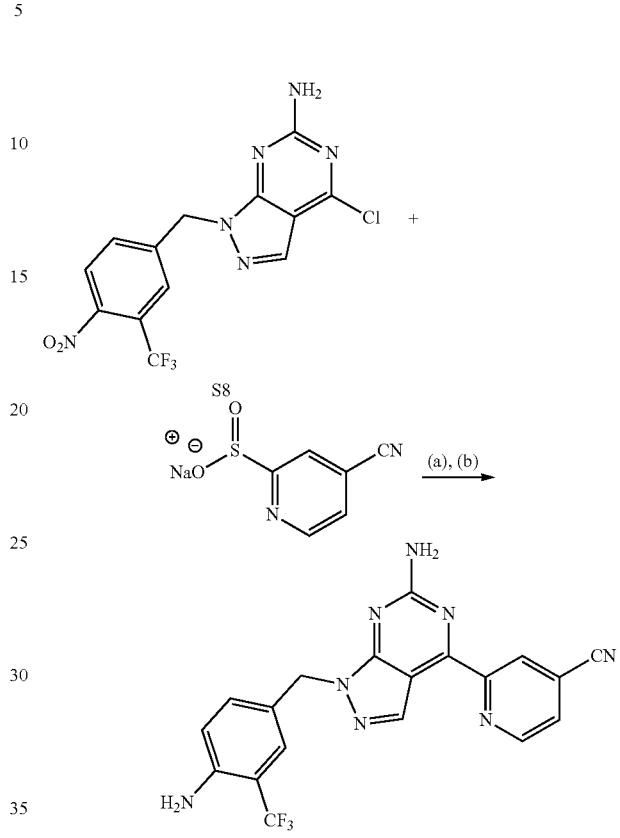

Reagents and condition: (a) Pd(OAc)$_2$, Cy$_3$P, K$_2$CO$_3$, dioxane, 120° C., 16h; (b) Fe, NH$_4$Cl, EtOH/H$_2$O, 60° C., 8h.

Stage 1: Production of 2-[6-amino-1-[[4-nitro-3-(trifluoromethyl)phenyl]methyl]pyrazolo[3,4-d]pyrimidine-4-yl]pyridine-4-carbonitrile A mixture of sodium 4-cyanopyridine-2-sulfinate (420 mg, 2.21 mmol, 2 eq), intermediate compound S9 or 4-chloro-1-[[4-nitro-3-(trifluoromethyl)phenyl]methyl]pyrazolo[3,4-d]pyrimidine-6-amine (435 mg, 1.10 mmol, 94.74% purity, 1 eq), palladium acetate (25 mg, 110.49 µmol, 0.1 eq), Cy$_3$P (62 mg, 220.98 µmol, 71.64 µL, 0.2 eq) and K$_2$CO$_3$ (305 mg, 2.21 mmol, 2 eq) in dioxane (10 mL) was degassed and purged with nitrogen for three times, and then the mixture was stirred at 120° C. for 16 hr under nitrogen atmosphere. The mixture was concentrated in vacuum to give a residue. The residue was purified by flash silica gel chromatography (12 g SEPAFLASH® Silica Flash Column, Eluent of 30~60% Ethyl acetate/Petroleum ether gradient @ 40 mL/min). Compound 2-[6-amino-1-[[4-nitro-3-(trifluoromethyl)phenyl]methyl]pyrazolo[3,4-d]pyrimidine-4-yl]pyridine-4-carbonitrile (160 mg, 354.13 µma 32% yield, 97.46% purity) was obtained as a yellow solid. $^1$H NMR (400 MHz, DMSO-d$_6$) δ=9.09 (d, J=4.9 Hz, 1H), 8.68 (s, 1H), 8.57 (d, J=1.0 Hz, 1H), 8.17-8.04 (m, 2H), 7.96 (s, 1H), 7.60 (dd, J=1.2, 8.4 Hz, 1H), 7.20 (s, 2H), 5.69 (s, 2H). MS: m/z=441.1 (M+1, ESI+).

Stage 2: Production of 2-[6-amino-1-[[4-amino-3-(trifluoromethyl)phenyl]methyl]pyrazolo[3,4-d]pyrimidine-4-yl]pyridine-4-carbonitrile (Compound 235)

To the solution of 2-[6-amino-1-[[4-nitro-3-(trifluoromethyl)phenyl]methyl]pyrazolo[3,4-d]pyrimidine-4-yl]pyridine-4-carbonitrile (150 mg, 340.65 μma 1 eq) in ethanol (10 mL) and water (3 mL) was added iron dust (95 mg, 1.70 mmol, 5 eq) and NH$_4$Cl (146 mg, 2.73 mmol, 8 eq). Then the mixture was stirred at 60° C. for 8 h. The reaction mixture was filtered, to the filtrate was added saturated NaHCO$_3$ solution (50 mL) and extracted with ethyl acetate (80 mL×3). Combined the organic phase to dry over anhydrous sodium sulfate, filter and concentrate in vacuum to give a residue. The residue was purified by prep-HPLC (column: Welch Ultimate XB-CN 250*70*10 μm; mobile phase: [Hexane-ethanol (0.1% ammonia hydroxide)]; B %: 20%-60%, 15 min). Compound 235 or 2-[6-amino-1-[[4-amino-3-(trifluoromethyl)phenyl]methyl]pyrazolo[3,4-d]pyrimidine-4-yl]pyridine-4-carbonitrile (76.29 mg, 180.52 μma 53% yield, 97.10% purity) was obtained as a yellow solid. $^1$H NMR (400 MHz, DMSO-d$_6$) δ=9.08 (dd, J=0.7, 5.0 Hz, 1H), 8.67 (d, J=0.9 Hz, 1H), 8.47 (s, 1H), 8.07 (dd, J=1.6, 5.0 Hz, 1H), 7.28 (d, J=1.6 Hz, 1H), 7.18 (dd, J=1.3, 8.6 Hz, 1H), 7.14 (s, 2H), 6.77 (d, J=8.4 Hz, 1H), 5.59 (s, 2H), 5.31 (s, 2H).

Example 2: Assessment of activity of pyrazolo-pyrimidine compounds

2.1 Human Adenosine A1 Receptor Binding Assay

General Method

Test compound is weighed, dissolved in DMSO to make a stock solution of 10 mM, diluted with DMSO to prepare working solutions, then 100-fold diluted to the indicated concentrations. Human recombinant adenosine A1 receptors expressed in CHO-K1 cells were used to prepare membranes in incubation buffer (20 mM HEPES (4-(2-hydroxyethyl)-1-piperazineethanesulfonic acid) pH 7.4, 10 mM MgCl$_2$, 100 mM NaCl). Test compound or vehicle (2.2 μL) was added in 200 μL of membranes and incubated with 20 μL of 1 nM [$^3$H] DPCPX (8-cyclopentyl-1,3-dipropylxanthine) for 90 minutes at 25° C. Non-specific binding was estimated in the presence of 100 μM R(−)-PIA ((R)—N-(1-methyl-2-phenylethyl)adenosine). The incubation was stopped by vacuum filtration onto 0.3% PEI (polyethylenimine) presoaked GF/B filters using a harvester followed by four washes with ice-cold 50 mM Tris-HCl, pH 7.4, and the radioactivity on GF/B filtermats counted in a scintillation counter (PerkinElmer Topcount™) to determine [$^3$H] DPCPX specifically bound. Final concentration of vehicle DMSO is 1%.

Data is fitted using the non-linear curve fitting routines in Meth-IQ software (ID Business Solutions Ltd., UK). IC$_{50}$ is converted to K$_i$ by Cheng-Prusoff equation: K$_i$=IC$_{50}$/(1+[L]/K$_D$) where [L] is concentration of radiolabeled ligand used in the assay.

2.2 Human Adenosine A2A Receptor Binding Assay

General Method

Test compound is weighed, dissolved in DMSO to make a stock solution of 10 mM, diluted with DMSO to prepare working solutions, then 100-fold diluted to the indicated concentrations. Human recombinant adenosine A$_{2A}$ receptors expressed in HEK-293 cells were used to prepare membranes in incubation buffer (50 mM Tris-HCl, pH 7.4, 10 mM MgCl$_2$, 1 mM EDTA, 2 U/ml Adenosine Deaminase). Test compound or vehicle (2.2 μL) was added in 200 μL of membranes and incubated with 20 μL of 50 nM [$^3$H] CGS-21680 for 90 minutes at 25° C. Non-specific binding was estimated in the presence of 50 μM NECA (5'-N-ethylcarboxamidoadenosine). The incubation was stopped by vacuum filtration onto 0.3% PEI (polyethylenimine) presoaked GF/B filters using a harvester followed by four washes with ice-cold 50 mM Tris-HCl, pH 7.4, and the radioactivity on GF/B filtermats counted in a scintillation counter (PerkinElmer TOPCOUNT™) to determine [$^3$H] CGS-21680 specifically bound. Final concentration of vehicle DMSO is 1%.

Data is fitted using the non-linear curve fitting routines in Meth-IQ software (ID Business Solutions Ltd., UK). IC$_{50}$ is converted to K$_i$ by Cheng-Prusoff equation: K$_i$=IC$_{50}$/(1+[L]/K$_D$) where [L] is concentration of radiolabeled ligand used in the assay.

2.3 Results

The A2A and A1 receptor binding affinity of select compounds was assessed using the binding assay described above in Examples 2.1 and 2.2. The binding affinity of reference adenosine receptor an antagonist compound Istradefylline (CAS No. 155270-99-8) was also measured in this assay.

Table 2: A2A and A1 receptor binding affinity of exemplary compounds.

For A2A receptor binding affinity:
A: K$_i$≤20 nM,
B: 20 nM<K$_i$≤200 nM,
C: 200 nM<K$_i$≤1000 nM,
D: 1000 nM<K$_i$≤5000 nM.

For A1 receptor binding affinity:
A: K$_i$≤0.1 μM,
B: 0.1 μM<K$_i$≤1 μM,
C: 1 μM<K$_i$≤10 μM,
D: K$_i$>10 μM.

TABLE 2

| Cmpd No. | hA1 K$_i$ (μM) | hA2A K$_i$ (nM) |
|---|---|---|
| 203 | A | A |
| 204 | B | A |
| 206 | A | A |
| 207 | A | A |
| 208 | A | A |
| 209 | B | A |
| 210 | A | A |
| 211 | A | A |
| 213 | A | A |
| 215 | B | B |
| 216 | C | C |
| 217 | D | D |
| 218 | C | D |
| 219 | B | A |
| 220 | B | B |
| 221 | D | D |
| 222 | D | D |
| 223 | B | A |
| 224 | B | B |
| 225 | C | D |
| 226 | D | D |
| 227 | B | A |
| 228 | B | B |
| 229 | D | D |

TABLE 2-continued

| Cmpd No. | hA1 $K_i$ (μM) | hA2A $K_i$ (nM) |
|---|---|---|
| 230 | D | D |
| 231 | B | A |
| 232 | B | B |
| 233 | C | C |
| 234 | C | C |
| 235 | B | A |
| Istradefylline | B | A |

The A2A receptor binding assay results of Table 2 indicate that the compounds of this disclosure can act as A2A receptor antagonists. Several compounds exhibited potent activity as dual antagonists of both A2A and A1 receptors. See e.g., compounds 203, 206, 207, 208, 211, and 213 in Table 2.

Biological Example 1: Assessment of In Vivo Neurodegenerative Disorder Treatment Activity in Animal Model 1.1 Method and Materials To generate animal model of Parkinson's Disease (PD), a number of 67 female Wistar Han rats of approximately 9 weeks of age received unilateral 6-hydroxydopamine (6-OHDA) lesion. To induce the 6-OHDA lesion, each of the animals received one injection with 2 μl (4 μg/μl) in the medial forebrain bundle (MFB). 6-OHDA is widely used to lesion the nigrostriatal dopaminergic system as a model of PD.

Three weeks after the injections, cylinder test for the evaluation of locomotor asymmetry was performed to determine the efficacy of the 6-OHDA lesion (4 animals died before testing). Based on the results of the cylinder test, 6-OHDA lesioned animals were further included in the study. In compound standalone testing groups (B+C), animals (n=52) were received L-DOPA (Levodopa or L-3,4-dihydroxyphenylalanine) priming (2 animals died before group allocation). Animals (n=11) not showing symptoms were eliminated without any further administration of test compounds or tissue collection.

Following baseline assessments in the cylinder test, all animals were treated for 21 consecutive days with L-DOPA/Benserazide (10/15 mg/kg ip). Behavioral assessment was performed again with axial, limb and orolingual abnormal involuntary movement score (ALO AIMs) and L-DOPA induced rotation test. In the compound standalone testing groups animals displaying robust symptoms were allocated to the testing groups (n=12 for group B; and n=11 for group C). Animals (n=27) of Groups B and C, who did not show symptoms were eliminated without further administration of test compounds or tissue collection.

Remaining 23 animals were administered with one of vehicle, four different doses of the 3-(6-amino-1-(4-amino-3-(trifluoromethyl)benzyl)-1H-pyrazolo[3,4-d]pyrimidine-4-yl)benzonitrile (compound 210; also referred to as "TI"), or a reference compound L-DOPA (benserazide) as shown in Table 3 either orally (PO in Group B and Group C) or via intranasal route (IN in Group C) six times in total.

After each treatment time point all animals were tested for axial, limb and orolingual abnormal involuntary movement scores (ALO AIMs). Additionally, animals receiving standalone treatment were tested in the cylinder test.

All tests were performed in a time critical manner within a defined time period after the treatment.

1.2 Cylinder Test

Cylinder test was performed on treatment days (4 days after end of L-DOPA priming) with all animals used for testing. Animals were tested 1 h (+/−5 min) after the vehicle, L-DOPA/Benserazide, and IN administration of the compound 210 (TI), and 3h (+/−5 min) after PO administration of the test compound. Cylinder test aims to evaluate the asymmetry in forelimb use in vertical exploratory activity (Rearing). The animals were placed into a cylinder of 20 cm diameter and 40 cm high. Each animal was individually evaluated for 5 minutes. The number of contacts on the cylinder wall with the right paw, left and both paws simultaneously were counted. The results were given in percentage and calculating is done as follows: the test total sum of contacts on the cylinder wall with the right paw, left paw and both totaled 100%, based on this, a percentage value for each finding was calculated (Araujo, 2013).

1.3 Axial, Limb and Orolingual Abnormal Involuntary Movement Scores (ALO AIMs) Tests ALO test was performed on treatment days (4 days after end of L-DOPA priming) with all animals used for the compound stand alone testing. ALO AIMs were scored starting 5 min (+/−min) after the vehicle, L-DOPA/Benserazide and IN administration of the test compound, and 2h (+/−5 min) after PO administration of the test compound and every 20 min thereafter for 3 h. All animals were placed in empty cages without bedding material. Axial, limbs and or o-lingual (ALO) AIMS were rated by an observer blinded to treatment, according to a protocol described by Cency and Lundblad (2007), which encompasses both time-based, i.e., "duration" and severity-based, i.e., "amplitude", assessment of abnormal movements.

ALO AIMs were scored for 1 min, every 20 min for 180 min. ALO AIMs duration was rated according to the following scale: 0=no dyskinesia; 1=occasional signs of dyskinesia, present for less than 50% of the observation period; 2=frequent signs of dyskinesia, present for more than 50% of the observation period; 3=dyskinesia present during the entire observation period, but suppressible by external stimuli and 4=continuous dyskinesia not suppressible by external stimuli. Axial AIMS amplitude is rated according to the following scale: 1=sustained deviation of the head and neck at −30° angle; 2=sustained deviation of the head and neck at an angle between 30°~60°; 3=sustained twisting of the head, neck and upper trunk at an angle between 60°~90° and; 4=sustained twisting of the head, neck and trunk at an angle >=90°; causing the rat to lose balance from a bipedal position.

Limbs AIMs amplitude was rated according to the following scale; 1=tiny movements of the paw around a fixed position; 2=movements leading to a visible displacement of the whole limb; 3=large displacement of the whole limb with visible contraction of shoulder muscles and 4=vigorous limb displacement of maximal amplitude, with concomitant contraction of shoulder and extensor muscles.

Orolingual AIMs amplitude was rated according to the following scale: 1=twitching of facial muscles accompanied by small masticatory movements without jaw opening; 2=twitching of facial muscles accompanied by masticatory movements that result in jaw opening; 3=movements with broad involvement of facila and masticatory muscles, with frequent jaw opening and occasional tongue protrusions and 4=involvement of all of the above muscles to the maximal possible degree. Integrated ALO AIMs were defined as the product of ALO AIMs amplitude x ALO AIMs duration, as previously described (Ohlin et al., 2011), while cumulative ALO AIMs indicates the sum of ALO AIMs duration or of ALO AIMs amplitude over different consecutive measurement time points (Frouni et al., 2018).

1.4 Animal's Body Weight

Body weights were recorded on a weekly basis and results are given in FIG. 1, animals in both treatment group showed a typical weight gain. No statistically significant differences were detected between the groups throughout the whole in life phase (see FIG. 1).

1.5 Results

The results are shown in FIGS. 1-3B. The results (e.g., the ALO scores measured on the last L-DOPA priming day, when the animals were allocated into the groups for the testing period) indicate that, at the end of the priming, all animals showed dyskinesia (FIG. 2A). After 4 days L-DOPA priming wash out period no more L-DOPA/benserazide-induced dyskinesia examined by AIM scores were observed (see FIG. 2B), meaning that treating animals with the compound 210 (TI) did not induce L-DOPA/Benserazide induced dyskinesia-like side effects, neither in terms of application route (per oral or intranasal) nor in concentration (FIG. 2B). The Cylinder test results indicate that during the testing period of the stand-alone efficacy study all lesioned animals showed decreased forelimb use contralateral to the lesion. However, a concentration related trend towards increased contralateral limb usage was observed in the inventive compound (TI)-administered group (IN route and PO route), compared to the vehicle treated group. And the intranasal administration showed more pronounced concentration related trend compared to the PO administration group.

TABLE 3

| Group | Tested Compounds (t = 0 for IN, t = −2 h for PO) | Doses (mg/kg) | Administration Route* | Behavioral Assessment (t = 0) | Behavioral Assessment (t = 1 h) | # of Animals |
|---|---|---|---|---|---|---|
| 8 | Vehicle | — | PO | ALO AIMS | Cylinder | 20->12 |
|   | TI dose 1 | 1 |    |    |    |    |
|   | TI dose 2 | 3 |    |    |    |    |
|   | TI dose 3 | 10 |    |    |    |    |
|   | TI dose 4 | 30 |    |    |    |    |
|   | L-DOPA (Benserazide) | 3 (15) |    |    |    |    |
| C | Vehicle | — | IN | ALO AIMS | Cylinder | 20->12 |
|   | TI dose 1 | 0.3 |    |    |    |    |
|   | TI dose 2 | 1 |    |    |    |    |
|   | TI dose 3 | 3 |    |    |    |    |
|   | TI dose 4 | 10 |    |    |    |    |
|   | L-DOPA (Benserazide) | 3 (15) | PO |    |    |    |

*PO: per oral
IN: intranasal

EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention. Therefore, it must be understood that the embodiments described above are for illustrative purposes and do not limit the present invention.

All references, issued patents and patent applications cited within the body of the instant specification, are herein incorporated by reference in their entirety for all purposes.

The invention claimed is:

1. A method of treating a subject with a central nerve system (CNS) disorder or neurodegenerative disorder, comprising administering an effective amount of a compound of formula (II):

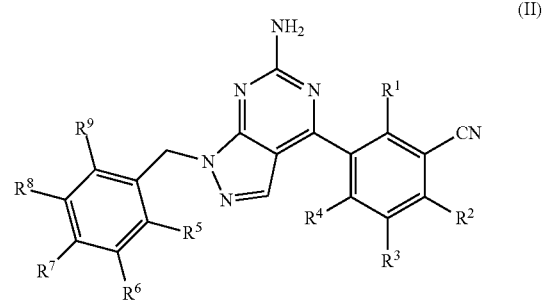

$R^1$ is selected from $(C_1-C_8)$alkyl, substituted $(C_1-C_8)$ alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

$R^2$ to $R^9$ are independently selected from H, $(C_1-C_8)$ alkyl, substituted $(C_1-C_8)$alkyl, $(C_2-C_8)$alkenyl, substituted $(C_2-C_8)$alkenyl, $(C_2-C_8)$alkynyl, substituted $(C_2-C_8)$alkynyl, $(C_1-C_3)$haloalkyl, $(C_1-C_8)$alkoxy, substituted $(C_1-C_8)$alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol, or a solvate, a hydrate, a prodrug, and/or a stereoisomer thereof, or a pharmaceutically acceptable salt thereof, to the subject.

2. The method of claim 1, wherein $R^1$ is $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl; and $R^2$ to $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, —$NH_2$, substituted amino, halogen, and hydroxyl.

3. The method of claim 2, wherein $R^1$ is selected from $NH_2$, F, $CH_3$, and $CF_3$; and $R^2$ to $R^9$ are independently selected from H, $NH_2$, F, $CH_3$, and $CF_3$.

4. The method of claim 1, wherein the compound is of formula (III):

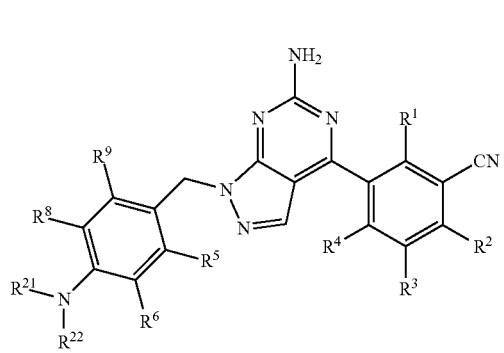

(III)

wherein:

$R^{21}$ and $R^{22}$ are independently selected from H, $(C_1\text{-}C_8)$alkyl, substituted $(C_1\text{-}C_8)$alkyl, $SO_2R^{30}$, and $COR^{30}$, wherein $R^{30}$ is $(C_1\text{-}C_8)$alkyl, or substituted $(C_1\text{-}C_8)$alkyl.

5. The method of claim 4, wherein $R^{21}$ and $R^{22}$ are each H;

$R^5$, $R^6$, $R^8$ and $R^9$ are independently selected from H, $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl;

$R^2$ to $R^4$ are each H; and $R^1$ is selected from $(C_1\text{-}C_5)$alkyl, substituted $(C_1\text{-}C_5)$alkyl, $(C_1\text{-}C_3)$haloalkyl, $(C_1\text{-}C_5)$alkoxy, substituted $(C_1\text{-}C_5)$alkoxy, halogen, and hydroxyl.

6. The method of claim 5, wherein $R^1$ is selected from H-F, $CH_3$, and $CF_3$.

7. The method of claim 1, wherein the compound of formula (II) is selected from:

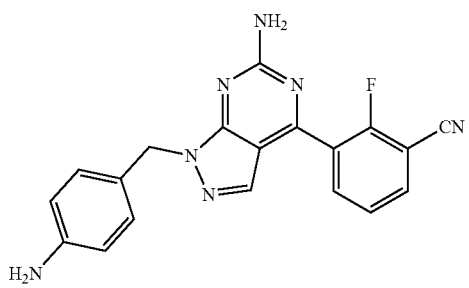

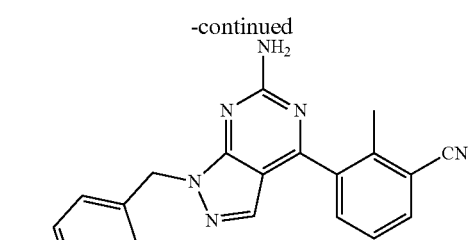

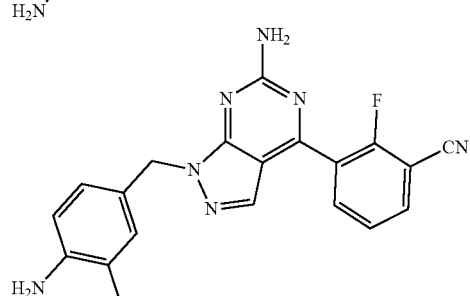

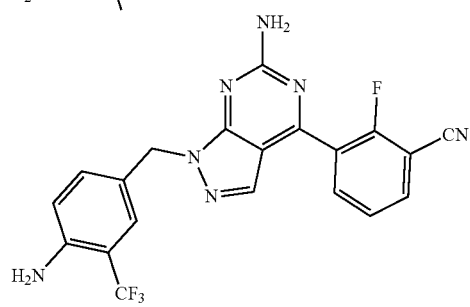

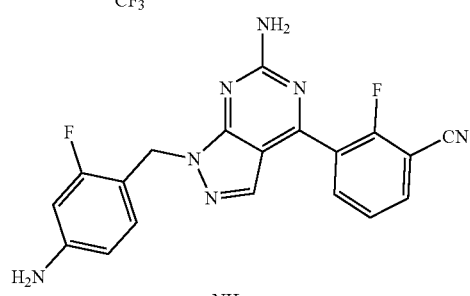

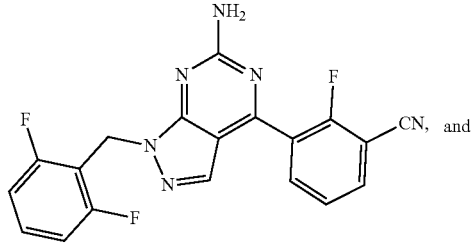

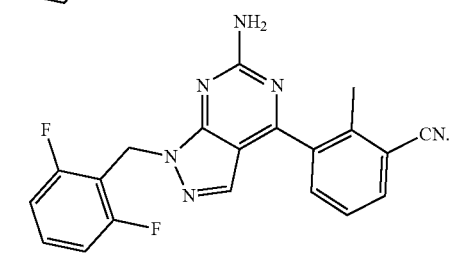

8. The method of claim 1, wherein the CNS disorder is selected from the group consisting of Huntington's disease, Parkinson's disease, Alzheimer's disease, schizophrenia, mild-cognitive impairment, attention deficit hyperactivity disorder (ADHD), multiple sclerosis, vascular dementia, and amyotrophic lateral sclerosis.

9. The method of claim 1, wherein the CNS disorder is associated with an adenosine receptor.

10. The method of claim 9, wherein the adenosine receptor is adenosine A2A and/or A1 receptor.

11. The method of claim 1, wherein the CNS disorder is Parkinson's disease.

12. A method of treating an injury or disease that results in neuronal degeneration selected from the group consisting of closed head injuries, blunt trauma, penetrating trauma, hemorrhagic stroke, ischemic stroke, glaucoma, cerebral ischemia, spinal cord injury, ageing, and neuronal damage caused by surgical procedures, comprising administering a therapeutically effective amount of a compound of formula (II):

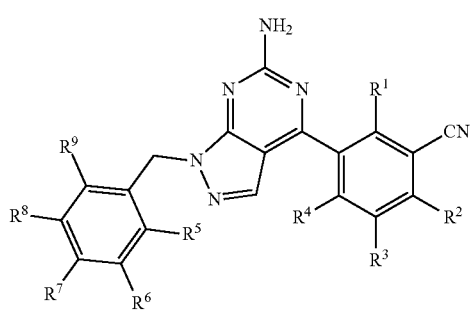

(II)

$R^1$ is selected from ($C_1$-$C_8$)alkyl, substituted ($C_1$-$C_8$) alkyl, ($C_2$-$C_8$)alkenyl, substituted ($C_2$-$C_8$)alkenyl, ($C_2$-$C_8$)alkynyl, substituted ($C_2$-$C_8$)alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

$R^2$ to $R^9$ are independently selected from H, ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$) alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol, or a solvate, a hydrate, a prodrug, and/or a stereoisomer thereof, or a pharmaceutically acceptable salt thereof, to the subject in need thereof, wherein the injury is a primary nervous system injury selected from the group comprising closed head injuries, blunt trauma, penetrating trauma, hemorrhagic stroke, ischemic stroke, glaucoma, cerebral ischemia, spinal cord injury, ageing, and neuronal damage caused by surgical procedures.

13. The method of claim 12, wherein the disease that results in neuronal degeneration is Parkinson's disease.

14. A method of treating a movement disorder in a subject, comprising administering to a subject in need thereof a therapeutically effective amount of a compound of formula (I):

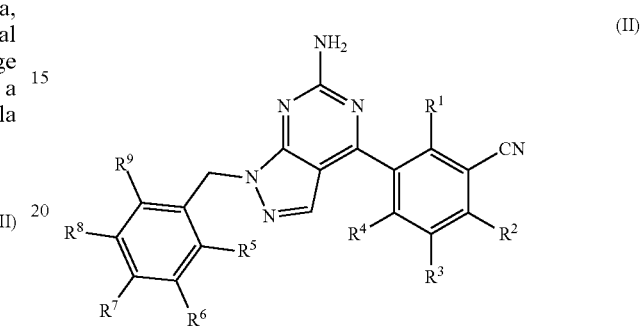

(II)

$R^1$ is selected from ($C_1$-$C_8$)alkyl, substituted ($C_1$-$C_8$) alkyl, ($C_2$-$C_8$)alkenyl, substituted ($C_2$-$C_8$)alkenyl, ($C_2$-$C_8$)alkynyl, substituted ($C_2$-$C_8$)alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol;

$R^2$ to $R^9$ are independently selected from H, ($C_1$-$C_8$)alkyl, substituted ($C_1$-$C_8$)alkyl, ($C_2$-$C_8$)alkenyl, substituted ($C_2$-$C_8$)alkenyl, ($C_2$-$C_8$)alkynyl, substituted ($C_2$-$C_8$) alkynyl, ($C_1$-$C_3$)haloalkyl, ($C_1$-$C_8$)alkoxy, substituted ($C_1$-$C_8$)alkoxy, —$CONH_2$, substituted amido, —$NH_2$, substituted amino, —$CO_2H$, cyano, halogen, hydroxyl, —$NO_2$, —$SO_3H$, —$SO_2NH_2$, substituted sulfonamide, and thiol, or a solvate, a hydrate, a prodrug, and/or a stereoisomer thereof, or a pharmaceutically acceptable salt thereof, to the subject.

15. The method of claim 14, wherein the subject suffers from an adenosine receptor associated disorder.

16. The method of claim 14, wherein the movement disorders is selected from the group consisting of bradykinesia, dystonia, chorea and Huntington's disease, ataxia, tremor, myoclonus and startle, tics and Tourette syndrome, Restless legs syndrome, stiff person syndrome, dyskinesia and gait disorders.

* * * * *